US012751453B2

(12) United States Patent
Hoeng et al.

(10) Patent No.: US 12,751,453 B2
(45) Date of Patent: Oct. 6, 2026

(54) COMPOSITIONS AND METHODS FOR PARASITE CONTROL

(71) Applicant: Philip Morris Products S.A., Neuchâtel (CH)

(72) Inventors: Julia Hoeng, Corcelles (CH); Nikolai Ivanov, Neuchâtel (CH); Kacper Kaminski, Neuchâtel (CH); Anatoly Mazurov, Greensboro, NC (US); Sandra Schorderet Weber, Neuchâtel (CH)

(73) Assignee: Philip Morris Products S.A., Neuchâtel (CH)

( * ) Notice: Subject to any disclaimer, the term of this patent is extended or adjusted under 35 U.S.C. 154(b) by 724 days.

(21) Appl. No.: 18/002,403

(22) PCT Filed: Jun. 23, 2021

(86) PCT No.: PCT/EP2021/067190
§ 371 (c)(1),
(2) Date: Dec. 19, 2022

(87) PCT Pub. No.: WO2021/260029
PCT Pub. Date: Dec. 30, 2021

(65) Prior Publication Data

US 2023/0225323 A1 Jul. 20, 2023

(30) Foreign Application Priority Data

Jun. 24, 2020 (EP) .................................... 20182044

(51) Int. Cl.

| | |
|---|---|
| ***A01N 43/90*** | (2006.01) |
| ***A01N 43/40*** | (2006.01) |
| ***A01P 17/00*** | (2006.01) |
| ***C07D 401/04*** | (2006.01) |
| ***C07D 401/12*** | (2006.01) |
| ***C07D 401/14*** | (2006.01) |
| ***C07D 453/06*** | (2006.01) |
| ***C07D 487/08*** | (2006.01) |

(52) U.S. Cl.
CPC ............. *A01N 43/90* (2013.01); *A01N 43/40* (2013.01); *A01P 17/00* (2021.08); *C07D 401/04* (2013.01); *C07D 401/12* (2013.01); *C07D 401/14* (2013.01); *C07D 453/06* (2013.01); *C07D 487/08* (2013.01)

(58) Field of Classification Search
CPC ......... A01N 43/90; A01N 43/40; A01P 17/00; C07D 401/04; C07D 401/12; C07D 453/06; C07D 487/08
See application file for complete search history.

(56) References Cited

U.S. PATENT DOCUMENTS

| | | | |
|---|---|---|---|
| 4,303,675 | A | 12/1981 | Di Pietro et al. |
| 4,900,834 | A | 2/1990 | Krüger et al. |
| 5,008,261 | A | 4/1991 | Krüger et al. |
| 5,175,175 | A | 12/1992 | Wilson et al. |
| 5,439,690 | A | 8/1995 | Knight |
| 5,441,988 | A | 8/1995 | Butler et al. |
| 5,665,781 | A | 9/1997 | Warren et al. |
| 5,693,344 | A | 12/1997 | Knight et al. |
| 6,114,384 | A | 9/2000 | Bessette et al. |
| 6,372,239 | B1 | 4/2002 | Wu et al. |
| 6,531,163 | B1 | 3/2003 | Bessette et al. |
| 6,570,036 | B1 | 5/2003 | Reuter |
| 8,841,343 | B2 | 9/2014 | Kwoen et al. |
| 2008/0280978 | A1 | 11/2008 | Zeelie et al. |
| 2019/0357529 | A1 | 11/2019 | Hansen et al. |

FOREIGN PATENT DOCUMENTS

| | | | |
|---|---|---|---|
| CN | 1133045 | A | 10/1996 |
| CN | 113891654 | A | 1/2022 |
| EP | 0 978 280 | A1 | 2/2000 |
| EP | 3 348 143 | A1 | 7/2018 |
| JP | 6-9397 | A | 1/1994 |
| JP | 8-502481 | A | 3/1996 |
| JP | 2022-537674 | A | 8/2022 |
| RU | 2 651 369 | C1 | 4/2018 |
| WO | WO 94/08992 | A1 | 4/1994 |

(Continued)

OTHER PUBLICATIONS

Â(-)-Anabasineâ Registry, Cas Reg. No. 494-52-0, 1984 (Year: 1984).*
Â(-)-Anatabineâ Registry, Cas Reg. No. 581-49-7, 1984 (Year: 1984).*
WO9848801A1, Nov. 5, 1998, translation (Year: 1998).*
"Pyridine, 3-(2-piperidinylmethoxy)" Registry, Cas Reg. No. 933759-31-0, 2007 (Year: 2007).*
Extended European Search Report issued Oct. 28, 2020, in corresponding European Patent Application No. 20182044.6, 7 pages.
Springuel G., et al., "Advances in Pharmaceutical Co-crystal Screening: Effective Cocrystal Screening through Structural Resemblance", Crystal Growth & Design, 2012, 12, pp. 475-484.
Johan Wouters, et al., "Chapter 15: Concluding Remarks using Piracetam as a Learning Model" RSC Drug Discovery, Pharmaceutical Salts and Co-crystals, published in 2012 by the Royal Society of Chemistry, 2012, pp. 330-338.

(Continued)

*Primary Examiner* — Brandon J Fetterolf
(74) *Attorney, Agent, or Firm* — Oblon, McClelland, Maier & Neustadt, L.L.P.

(57) ABSTRACT

A compound of Formula I and formulations including such a compound may be used for the reduction of infestation with ectoparasites, in particular ectoparasites of the insect class, including fleas and mosquitoes, and/or ectoparasites of the arachnid class, including ticks and mites, etc. Methods for controlling ectoparasites and/or formulations including such compounds may include use as a repellent, and/or application to a mammal, e.g., a human, dog, cat, cattle, horse, or sheep, or to an object or a fabric. The form may be a topical formulation, a shampoo composition, a cleansing composition, or a treatment composition, preferably a lotion, cream, ointment, gel, foam, patch, powder, solid, sponge, tape, vapor, paste, tincture, or spray.

13 Claims, No Drawings

(56) References Cited

FOREIGN PATENT DOCUMENTS

| | | | | |
|---|---|---|---|---|
| WO | 1995003306 | A1 | * | 2/1995 |
| WO | WO 95/03306 | A1 | | 2/1995 |
| WO | WO 96/36637 | A1 | | 11/1996 |
| WO | WO 98/48801 | A1 | | 11/1998 |
| WO | WO 2014/192868 | A1 | | 12/2014 |
| WO | WO 2020/260392 | A1 | | 12/2020 |

OTHER PUBLICATIONS

Johan Wouters, et al., "Chapter 16: Monographs of Most frequent Co-Crystal Formers" RSC Drug Discovery, Pharmaceutical Salts and Co-crystals, published in 2012 by the Royal Society of Chemistry, 2012, pp. 338-382.

Mahdi Jufri et al., "Formulation of Tobacco Based Mosquito Repellent to Avoid Dengue Fever", International Journal of PharmTech Research, 2016, 9, No. 7, pp. 140-145.

International Search Report and Written Opinion issued Oct. 15, 2021 in PCT/EP2021/067190, filed on Jun. 23, 2021, 10 pages (with English Translation).

Tomizawa, M. et al. "Neonicotinoid Insecticide Toxicology: Mechanisms of Selective Action", Annual Review of Pharmacology and Toxicology, vol. 45, Sep. 7, 2004, XP-002426971 (26 pages).

Krow, G. et al. Nitrogen Bridge Homoepibatidines. syn-6-and syn-5(6-Chloro-3-pyridyl)isoquinuclidines. Tetrahedron, vol. 55, No. 25, Jun. 18, 1999. 7747-7756, XP-004168552 (10 pages).

Szczepanski, S.W. et al. "Synthesis of Semi-Rigid Analogs of Anabasine", Tetrahedron Letters, vol. 37, No. 49 pp. 8841-8844, Dec. 2, 1996, XP-005029145 (4 pages).

Combined Japanese Office Action and Search Report issued May 22, 2025 in Japanese Patent Application No. 2022-577651 (with English Translation), 46 pages.

Weber et al., "Antiparasitic properties of leaf extracts derived from selected *Nicotiana* species and Nicotiana tabacum varieties", Food and Chemical Toxicology, vol. 132, 2019, 12 pages.

"2-(3-Pyridyl)-1,2,5,6-tetrahydropyridine", Pub Chem, Pub Chem CID 46837530, Aug. 9, 2010, 10 pages.

"Pyridine, 3-(2-piperidinylmethoxy)-"Registry, CAS Registration No. 933759-31-0, Apr. 30, 2007, 1 page.

Combined Chinese Office Action and Search Report issued Nov. 9, 2024, in corresponding Chinese Patent Application No. 202180043146.2 (with English Translation) 23 pages.

"Extraction and Bioactivity Study of Alkaloids in Tobacco", China Excellent Master's Degree Thesis Full-text Database Engineering Technology I Series, 2019, Issue 01, 14 pages.

Russian Office Action issued Jun. 26, 2025 in Russian Patent Application No. 2023101240/04 (with English Translation), 30 pages.

Combined Russian Office Action and Search Report issued Dec. 6, 2024 in Russian Patent Application No. 2023101240/04 (with English Translation), 34 pages.

Pinto et al., "Thermoanalytical studies of carbamazepine: hydration/dehydration, thermal decomposition, and solid phase transitions", Brazilian Journal of Pharmaceutical Sciences, vol. 50, No. 4, 2014, pp. 877-884.

Caira, "Crystalline Polymorphism of Organic Compounds", Topics of Current Chemistry, vol. 198, 1998, 46 pages.

May et al., "Chemistry of Synthetic Drug", Publishing House, 1964, 9 pages.

Belikov, "Pharmaceutical Chemistry", Medpress-inform, 2007, 4 pages.

Indian Office Action issued Feb. 19, 2026 in Indian Patent Application No. 202317004059, 9 pages.

Yamamoto et al., "Studies on Nicotinoids as an Insecticide, Part VII. Cholinesterase Inhibition by Nicotinoids and Pyridyl-alkylamines—Its Significance to Mode of Action", Agricultural and Biological Chemistry, vol. 32, No. 11, 1968, pp. 1341-1348.

* cited by examiner

COMPOSITIONS AND METHODS FOR PARASITE CONTROL

CROSS-REFERENCE TO RELATED APPLICATIONS

The present application is the national stage of international application PCT/EP2021/067190, filed on Jun. 23, 2021, and claims the benefit of the filing date of European Appl. No. 20182044.6, filed on Jun. 24, 2020.

The present invention relates in its broadest aspect to a compound of Formula I as provided herein, formulations comprising such a compound and corresponding uses thereof for the reduction of infestation with ectoparasites, in particular with insects, preferably with mosquitoes. Also provided herein are methods for preparing the formulations of the invention and methods for controlling ectoparasites using the compounds and/or formulations provided herein.

The infestation of animals or humans with parasites is highly undesirable. Humans or animals, for example, horses, dogs and cats all can serve as hosts for a large number of internal and external parasites. The presence of parasites can lead to discomfort, impaired health and performance, and even death. Each year, for example, millions of dogs and cats in the United States are treated for fleas, ticks, and mites. Flea, tick, and mite infestations cause great discomfort, transmit disease to pets and humans.

Mosquitoes are important as disease carriers. They transmit, for example, malaria, parasitic worms (filariasis), viruses (e.g. yellow fever, dengue fever, West Nile fever, chikungunya fever, Rift Valley fever) or bacteria (tularemia). Diseases that can be transmitted from mosquitoes to animals include Venezuelan equine encephalomyelitis, myxomatosis or rabbit plague, or the worms *Dirofilaria repens* and *Dirofilaria immitis*, which parasitize domestic dogs.

Mosquitoes can also significantly affect the quality of life of humans and animals if they appear in large numbers, since it is no longer possible to stay outdoors. This can lead to economic damage in the tourism sector or in livestock farming.

Several classes of insecticides are effective for combating parasites. For example, pyrethroids, organophosphates, organocarbarnates, and phenylpyrazoles are used to treat animals for parasite infestation. The newly discovered isoxazoline class was recently launched for ectoparasite control in dogs and cats. Various methods of formulating anti-parasitic agents are known in the art. These formulations include oral treatments, dietary supplements, powders, sprays, topical treatments (e.g., dips and pour ons), and shampoos. While each of these formulations has some efficacy in combating parasites, the formulations generally include synthetic insecticides or repellents. Synthetic insecticides have been known to cause environmental effects that are harmful to humans and animals. Similarly, Pyrethrin, although extracted from the *Chrysanthemum* flower, is hard to process and standardize.

Natural insecticides, i.e., insecticides that include natural plant essential oils as an active ingredient, have been known to kill household parasites such as ants, cockroaches, and fleas by applying the natural insecticide in the form of a spray, powder, or liquid to a locus or area to be protected from the parasites, as disclosed in U.S. Pat. Nos. 5,439,690, 5,693,344, 6,114,384, and 6,531,163.

Natural compounds or extracts have also been described in the art, e.g. by Jufri et al. (2016) International Journal of PharmTech Research 9, No. 7, pp. 140-145.

Further, tobacco (*Nicotiana* genus spp.) leaves, powder, extracts or fumigants have been used for centuries to control agricultural pests or parasites of medical and veterinary importance. However, because of safety concerns regarding tobacco's major alkaloid nicotine and the discovery of more specific and potent synthetic pesticides, no nicotine-based products are currently commercially available. Synthetic neonicotinoids are structurally related to nicotine and widely used as agricultural and veterinary pesticides; however, unlike tobacco-related alkaloids, synthetic neonicotinoids have a higher selectivity for the insect nicotinic acetylcholine receptor (nAChR) and reduced binding to vertebrate nicotinic receptors. Their unique physicochemical features (photostability, non-volatility and hydrophilicity) explain their success as pesticides, but also their excessive use that lead to an extensive contamination of the environment. Neonicotinoids have now become a major concern for the survival of ecosystems. The proven impact on pollinators, aquatic and soil communities, and a more problematic toxicity profile than once perceived, pushes forward initiatives to limit or totally ban their use in agriculture, and move away from the worldwide use of synthetic pesticides.

In view of the concerns associated with the use of tobacco's major alkaloid nicotine or the structurally related synthetic neonicotinoids, a need still exists for more effective compounds and compositions for use in controlling ectoparasites on humans and/or animals that have better safety profile than nicotine or the synthetic neonicotinoids due to differentiated mode of action and offer a more environmentally friendly solution. Many known insecticide classes are not fully protective, in particular those acting systemicly, such as the isooxazolines, and do not prevent ecptoparasites from biting, increasing the risk of vector borne disease transmission. Therefore, it is desirable to provide new compounds and formulations which are in particular active as a repellent for ectoparasites. Accordingly, rather than killing the ectoparasites, such compounds can keep ectoparasites away from areas or subjects to be protected.

The solution to the above technical problem is characterized in the herein provided embodiments and claims.

Accordingly, the invention relates to, inter alia, the following embodiments:

1. A compound selected from any of the following compounds, including their salts and solvates:

2-phenyl-5-(1,2,3,6-tetrahydropyridin-2-yl)pyridine
2-chloro-5-(1,2,3,6-tetrahydropyridin-2-yl)pyridine
2,3-dichloro-5-(1,2,3,6-tetrahydropyridin-2-yl)pyridine
3-ethynyl-5-(1,2,3,6-tetrahydropyridin-2-yl)pyridine
2-[5-(1,2,3,6-tetrahydropyridin-2-yl)-3-pyridyl]-2,5-diazabicyclo[2.2.1]heptane
3-[(2S)-4-phenyl-1,2,3,6-tetrahydropyridin-2-yl]pyridine
3-[(2S)-2-(3-pyridyl)-1,2,3,6-tetrahydropyridin-4-yl]pyridine
2-methyl-3-(2-phenyl-5-pyridyl)-2-azabicyclo[2.2.2]octane
5-(2-chloro-5-pyridyl)-2-azabicyclo[2.2.2]oct-5-ene
5-(2-chloro-5-pyridyl)-2-methyl-2-azabicyclo[2.2.2]oct-5-ene
7-(3-pyridyl)-2-azabicyclo[2.2.2]oct-5-ene
7-(2-chloro-5-pyridyl)-2-azabicyclo[2.2.2]oct-5-ene
3-[[(2S)-1,2,3,6-tetrahydropyridin-2-yl]methoxy]pyridine
2-ethynyl-5-[2-(3-pyridyl)-1,2,3,6-tetrahydropyridin-4-yl]pyridine
2-methyl-7-(3-pyridyl)-2-azabicyclo[2.2.2]oct-5-ene
7-(2-chloro-5-pyridyl)-2-methyl-2-azabicyclo[2.2.2]oct-5-ene, and 7-(2-ethoxypyridin-5-yl)-2-methyl-2-azabicyclo[2.2.2]oct-5-ene.

2. Use of a compound of formula (I) or a salt or crystal thereof for the reduction of infestation with ectoparasites:

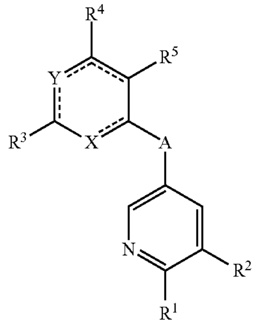

wherein

X is selected from C—$R^7$ and N, if the ===== attached to X is a double bond, or is selected from $C(R^7)_2$ and N—$R^7$, if the ===== attached to X is a single bond, Y is selected from C—$R^8$ and N, if one of thel ===== attached to Y is a double bond, or is selected from $C(R^8)_2$ and N—$R^8$, if none of the ===== attached to Y is a double bond, $R^1$ and $R^2$ are each independently selected from hydrogen, halogen, alkyl, haloalkyl, heteroalkyl, alkenyl, alkynyl, optionally substituted cycloalkyl, optionally substituted cycloheteroalkyl, optionally substituted aryl and optionally substituted heteroaryl, $R^3$, $R^4$, $R^5$ are each independently selected from hydrogen, halogen, alkyl, haloalkyl, heteroalkyl, alkenyl, alkynyl, optionally substituted cycloalkyl, optionally substituted cycloheteroalkyl, optionally substituted aryl and optionally substituted heteroaryl, or wherein optionally $R^1$ and $R^4$, or optionally $R^3$ and $R^5$, are taken together to form group Z selected from $—CH_2—$, $—CH_2—CH_2—$, $—CH{=}CH—$, $—CH_2—NR^9$, $—NR^9—CH_2—$, $—CH_2—CH_2—CH_2—$, and $—CH_2—CH_2—NR^9—$, $—NR^9—CH_2—CH_2—$, and $—CH_2—NR^9—CH_2—$, wherein each $R^9$ is independently selected from hydrogen, alkyl, haloalkyl and heteroalkyl, ===== independently indicates a single bond or a double bond, A is selected from a bond and -L1-L2-L3-L4-, wherein L1 is connected to the ring containing X and Y, wherein L1 is selected from a methylene group which is optionally substituted with halogen, alkyl, haloalkyl and/or heteroalkyl, L2 is selected from a bond, —O— and a methylene group wherein the methylene group is optionally substituted with halogen, alkyl, haloalkyl and/or heteroalkyl, L3 is a bond or a methylene group wherein the methylene group is optionally substituted with halogen, alkyl, haloalkyl and/or heteroalkyl, L4 is a bond or a methylene group wherein the methylene group is optionally substituted with halogen, alkyl, haloalkyl and/or heteroalkyl, $R^7$ and $R^8$ are each independently selected from hydrogen, alkyl, haloalkyl and heteroalkyl, and the optional substituent of the optionally substituted cycloalkyl, optionally substituted cycloheteroalkyl, optionally substituted aryl and optionally substituted heteroaryl is/are each independently selected from halogen, alkyl, haloalkyl and heteroalkyl.

3. The use according to item 2, wherein the following compounds are excluded:

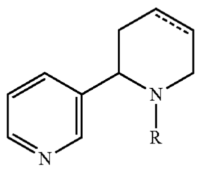

wherein

R represents hydrogen or $C_1$-$C_5$ alkyl, and

===== represents a single or double bond.

4. The use according to item 2 or 3, wherein the ring containing X and Y contains only one or two double bonds, preferably one double bond.

5. The use according to any one of items 2 to 4, wherein the compound of formula (I) is represented by the following formula (Ia):

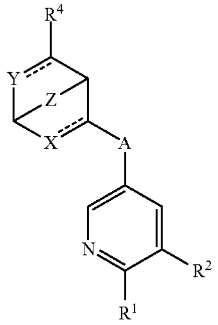

wherein $R^4$, $R^2$, $R^4$, A, X, Y and Z are as defined in item 2, and

===== indicates a single bond or a double bond.

6. The use according to any one of items 1 to 3, wherein the compound of formula (I) is represented by the following formula (Ib):

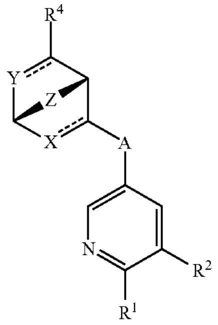

wherein $R^4$, $R^2$, $R^4$, A, X, Y and Z are as defined in item 2, and

===== indicates a single bond or a double bond.

7. The use according to any one of items 1 to 3, wherein the compound of formula (I) is represented by the following formula (Ic):

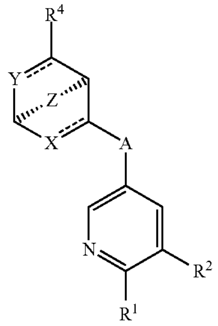

wherein $R^1$, $R^2$, $R^4$, A, X, Y and Z are as defined in item 2, and ═══ indicates a single bond or a double bond.

8. The use according to any one of items 1 to 3, wherein the compound of formula (I) is represented by the following formula (Id):

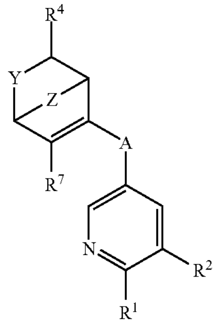

wherein $R^1$, $R^2$, $R^4$, $R^7$, A, Y and Z are as defined in item 2.

9. The use according to any one of items 1 to 3, wherein the compound of formula (I) is represented by the following formula (Ie):

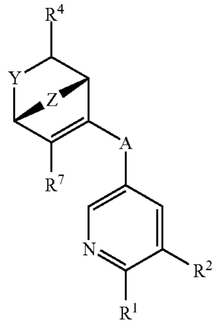

wherein $R^1$, $R^2$, $R^4$, $R^7$, A, Y and Z are as defined in item 2.

10. The use according to any one of items 1 to 3, wherein the compound of formula (I) is represented by the following formula (If):

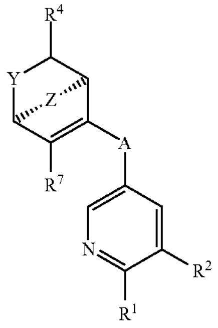

wherein $R^1$, $R^2$, $R^4$, $R^7$, A, Y and Z are as defined in item 2.

11. The use according to any one of items 1 to 3, wherein the compound of formula (I) is represented by the following formula (Ig):

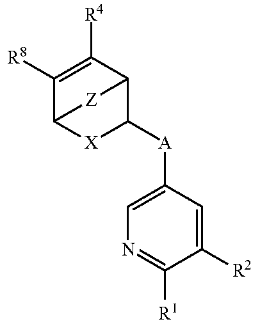

wherein $R^1$, $R^2$, $R^4$, $R^8$, A, X and Z are as defined in item 2.

12. The use according to any one of items 1 to 3, wherein the compound of formula (I) is represented by the following formula (Ih):

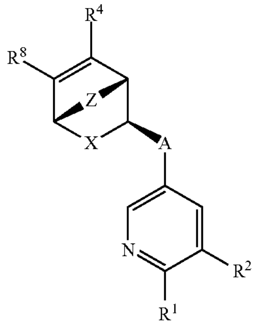

wherein $R^4$, $R^2$, $R^4$, $R^8$, A, X and Z are as defined in item 2.

13. The use according to any one of items 1 to 3, wherein the compound of formula (I) is represented by the following formula (Ii):

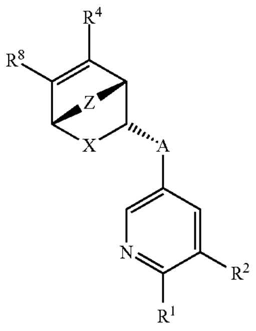

wherein $R^1$, $R^2$, $R^4$, $R^8$, A, X and Z are as defined in item 2.

14. The use according to any one of items 1 to 3, wherein the compound of formula (I) is represented by the following formula (Ij):

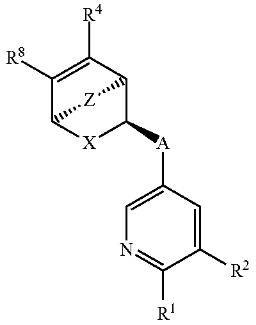

wherein $R^1$, $R^2$, $R^4$, $R^8$, A, X and Z are as defined in item 2.

15. The use according to any one of items 1 to 3, wherein the compound of formula (I) is represented by the following formula (Ik):

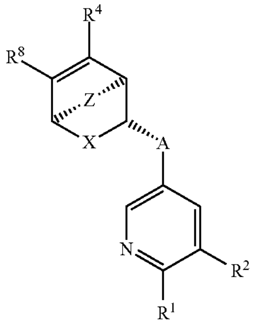

wherein $R^1$, $R^2$, $R^4$, $R^8$, A, X and Z are as defined in item 2.

16. The use according to item 1 or 2, wherein the compound of formula (I) is represented by the following formula (Il):

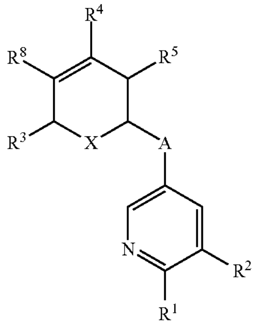

wherein $R^4$, $R^2$, $R^3$, $R^4$, $R^5$, $R^8$, A and X are as defined in item 2.

17. The use according to any one of items 1 to 3, wherein the compound of formula (I) is represented by the following formula (Im):

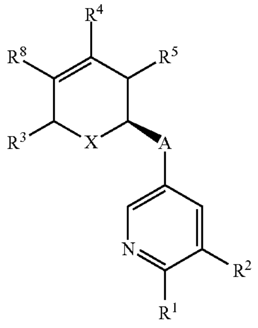

wherein $R^4$, $R^2$, $R^3$, $R^4$, $R^5$, $R^8$, A and X are as defined in item 2.

18. The use according to any one of items 1 to 3, wherein the compound of formula (I) is represented by the following formula (In):

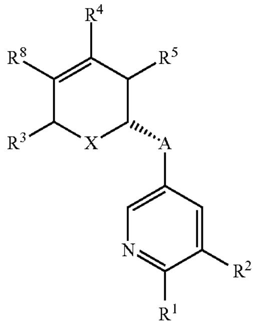

wherein $R^1$, $R^2$, $R^3$, $R^4$, $R^5$, $R^1$, A and X are as defined in item 2.

19. The use according to any one of items 1 to 3, wherein the compound of formula (I) is represented by the following formula (Io):

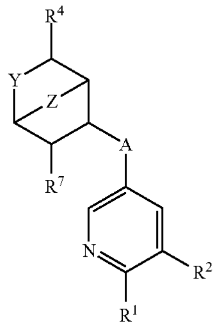

wherein $R^1$, $R^2$, $R^4$, $R^7$, A, Y and Z are as defined in item 2.

20. The use according to any one of items 1 to 3, wherein the compound of formula (I) is represented by the following formula (Ip):

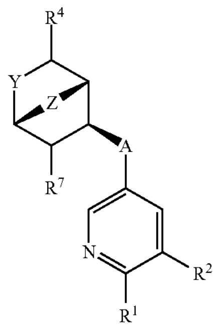

wherein $R^1$, $R^2$, $R^4$, $R^7$, A, Y and Z are as defined in item 2.

21. The use according to any one of items 1 to 3, wherein the compound of formula (I) is represented by the following formula (Iq):

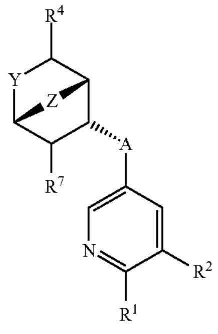

wherein $R^1$, $R^2$, $R^4$, $R^7$, A, Y and Z are as defined in item 2.

22. The use according to any one of items 1 to 3, wherein the compound of formula (I) is represented by the following formula (Ir):

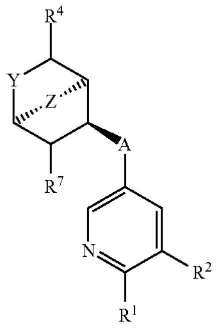

wherein $R^4$, $R^2$, $R^4$, $R^7$, A, Y and Z are as defined in item 2.

23. The use according to any one of items 1 to 3, wherein the compound of formula (I) is represented by the following formula (Is):

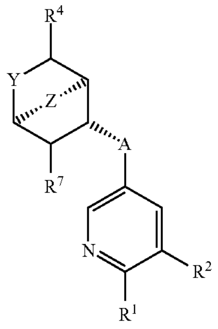

wherein $R^1$, $R^2$, $R^4$, $R^7$, A, Y and Z are as defined in item 2.

24. The use according to any one of items 1 to 3, wherein the compound of formula (I) is represented by the following formula (It):

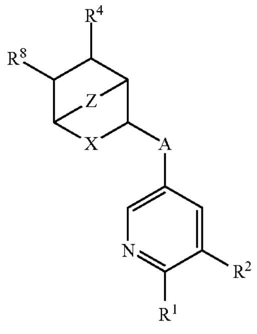

wherein $R^1$, $R^2$, $R^4$, $R^8$, A, X and Z are as defined in item 2.

25. The use according to any one of items 1 to 3, wherein the compound of formula (I) is represented by the following formula (Iu):

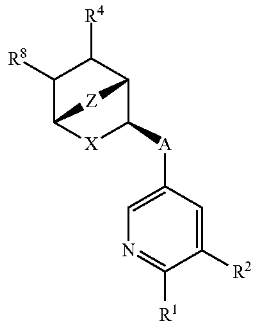

wherein $R^1$, $R^2$, $R^4$, $R^8$, A, X and Z are as defined in item 2.

26. The use according to any one of items 1 to 3, wherein the compound of formula (I) is represented by the following formula (Iv):

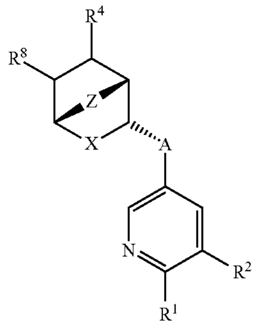

wherein $R^1$, $R^2$, $R^4$, $R^8$, A, X and Z are as defined in item 2.

27. The use according to any one of items 1 to 3, wherein the compound of formula (I) is represented by the following formula (Iw):

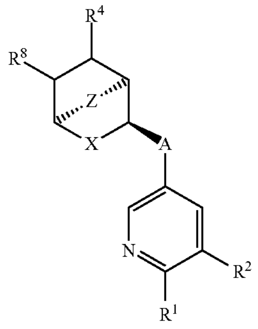

wherein $R^4$, $R^2$, $R^4$, $R^8$, A, X and Z are as defined in item 2.

28. The use according to any one of items 1 to 3, wherein the compound of formula (I) is represented by the following formula (Ix):

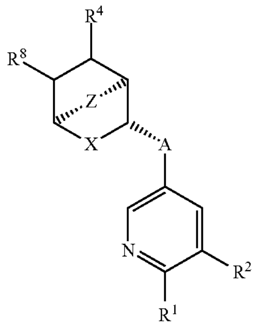

wherein $R^1$, $R^2$, $R^4$, $R^8$, A, X and Z are as defined in item 2.

29. The use of the compound according to any one of items 2 to 27, wherein $R^1$ is selected from hydrogen, halogen, alkyl, haloalkyl, heteroalkyl, alkynyl, optionally substituted cycloalkyl, optionally substituted cycloheteroalkyl and optionally substituted aryl.

30. The use of the compound according to any one of items 2 to 27, wherein $R^1$ is selected from hydrogen, halogen, heteroalkyl and optionally substituted aryl.

31. The use of the compound according to any one of items 2 to 27, wherein $R^1$ is selected from hydrogen, halogen, —O-alkyl and phenyl.

32. The use of the compound according to any one of items 2 to 27, wherein $R^2$ is selected from hydrogen, halogen, alkyl, haloalkyl, heteroalkyl, alkynyl, optionally substituted cycloalkyl, optionally substituted cycloheteroalkyl and optionally substituted aryl.

33. The use of the compound according to any one of items 2 to 27, wherein $R^2$ is selected from hydrogen, halogen, alkyl, haloalkyl, heteroalkyl, alkynyl, optionally substituted cycloalkyl and optionally substituted cycloheteroalkyl.

34. The use of the compound according to any one of items 2 to 27, wherein $R^2$ is selected from hydrogen, halogen, alkynyl and optionally substituted cycloheteroalkyl.

35. The use of the compound according to any one of items 2 to 27, wherein Z is selected from $—CH_2—CH_2—$, $—CH{=}CH—$, $—CH_2—NR^9$, $—NR^9—CH_2—$, $—CH_2—CH_2—CH_2—$, $—CH_2—CH_2—NR^9—$, $—NR^9—CH_2—CH_2—$, and $—CH_2—NR^9—CH_2—$.

36. The use of the compound according to any one of items 2 to 27, wherein Z is selected from $—CH_2—CH_2—$, $—CH{=}CH—$, $—CH_2—NR^9$ and $—NR^9—CH_2—$, preferably wherein Z is $—CH_2—CH_2—$ or $—CH{=}CH—$, more preferably wherein Z is $—CH_2—CH_2—$.

37. The use of the compound according to any one of items 2 to 27, wherein L1 is selected from a methylene group which is optionally substituted with halogen and/or alkyl.

38. The use of the compound according to any one of items 2 to 27, wherein L1 is selected from a methylene group which is optionally substituted with halogen and/or methyl.

39. The use of the compound according to any one of items 2 to 27, wherein L1 is a methylene group.

40. The use of the compound according to any one of items 2 to 27, wherein L2 is selected from a bond, —O— and a methylene group wherein the methylene group is optionally substituted with halogen and/or alkyl.

41. The use of the compound according to any one of items 2 to 27, wherein L2 is selected from a bond and —O—.

42. The use of the compound according to any one of items 2 to 27, wherein L2 is a bond.

43. The use of the compound according to any one of items 2 to 27, wherein L3 is selected from a bond or a methylene group which is optionally substituted with halogen and/or methyl.

44. The use of the compound according to any one of items 2 to 27, wherein L3 is a bond.

45. The use of the compound according to any one of items 2 to 27, wherein L4 is selected from a bond or a methylene group which is optionally substituted with halogen and/or methyl.

46. The use of the compound according to any one of items 2 to 27, wherein L4 is a bond.

47. The use of the compound according to any one of items 2 to 27, wherein $R^7$ is selected from hydrogen, alkyl, haloalkyl and heteroalkyl.

48. The use of the compound according to any one of items 2 to 27, wherein $R^7$ is selected from hydrogen, alkyl and haloalkyl.

49. The use of the compound according to any one of items 2 to 27, wherein $R^7$ is hydrogen or methyl.

50. The use of the compound according to any one of items 2 to 27, wherein $R^8$ is selected from hydrogen, alkyl, haloalkyl and heteroalkyl.

51. The use of the compound according to any one of items 2 to 27, wherein $R^8$ is selected from hydrogen, alkyl and haloalkyl.

52. The use of the compound according to any one of items 2 to 27, wherein $R^8$ is hydrogen or methyl.

53. The use of the compound according to any one of items 2 to 27, wherein each $R^9$ is independently selected from hydrogen, alkyl, haloalkyl and heteroalkyl.

54. The use of the compound according to any one of items 2 to 27, wherein each $R^9$ is independently selected from hydrogen, alkyl and haloalkyl.

55. The use of the compound according to any one of items 2 to 27, wherein each $R^9$ is independently selected from hydrogen and methyl.

56. The use of the compound according to item 2, wherein the compound is as defined in item 1.

57. The use of the compound according to item 2, wherein the compound of formula (I) is selected from exo-3-(3-pyridyl)-2-azabicyclo[2.2.2]oct-5-ene, endo-3-(3-pyridyl)-2-azabicyclo[2.2.2]oct-5-ene, 2-methyl-3-(3-pyridyl)-2-azabicyclo[2.2.2]octane, 2-methyl-3-(3-pyridyl)-2-azabicyclo[2.2.2]octane, 3-(1,2,3,6-tetrahydropyridin-2-yl)pyridine, 3-(1,2,5,6-tetrahydropyridin-4-yl)pyridine dihydrochloride, 3-(1,2,3,6-tetrahydropyridin-6-yl)pyridine dihydrochloride, 2-phenyl-5-(1,2,3,6-tetrahydropyridin-2-yl)pyridine dihydrochloride, 2-chloro-5-(1,2,3,6-tetrahydropyridin-2-yl)pyridine dihydrochloride, 2,3-dichloro-5-(1,2,3,6-tetrahydropyridin-2-yl)pyridine dihydrochloride, 3-ethynyl-5-(1,2,3,6-tetrahydropyridin-2-yl)pyridine dihydrochloride, 2-[5-(1,2,3,6-tetrahydropyridin-2-yl)-3-pyridyl]-2,5-diazabicyclo[2.2.1]heptane dihydrochloride, 3-[(2S)-4-phenyl-1,2,3,6-tetrahydropyridin-2-yl]pyridine dihydrochloride, 3-[(2S)-2-(3-pyridyl)-1,2,3,6-tetrahydropyridin-4-yl]pyridine dihydrochloride, 2-methyl-3-(3-pyridinyl)-2-azabicyclo[2.2.2]oct-5-ene, 3-(6-chloro-3-pyridyl)-2-methyl-2-azabicyclo[2.2.2]oct-5-ene, 3-(6-chloro-3-pyridyl)-2-methyl-2-azabicyclo[2.2.2]octane, 2-methyl-3-(6-phenyl-3-pyridyl)-2-azabicyclo[2.2.2]octane hydrochloride, 5-(3-pyridyl)-2-azabicyclo[2.2.2]oct-5-ene, 2-methyl-5-(3-pyridyl)-2-azabicyclo[2.2.2]oct-5-ene, 5-(6-chloro-3-pyridyl)-2-azabicyclo[2.2.2]oct-5-ene hydrochloride, 5-(6-chloro-3-pyridyl)-2-methyl-2-azabicyclo[2.2.2]oct-5-ene, 7-(3-pyridyl)-2-azabicyclo[2.2.2]oct-5-ene, 7-(6-chloro-3-pyridyl)-2-azabicyclo[2.2.2]oct-5-ene, 3-(2-piperidylmethoxy)pyridine, 3-[[(2S)-1,2,3,6-tetrahydropyridin-2-yl]methoxy]pyridine, 2-ethynyl-5-[2-(3-pyridyl)-1,2,3,6-tetrahydropyridin-4-yl]pyridine, 2-methyl-7-(3-pyridyl)-2-azabicyclo[2.2.2]oct-5-ene, 7-(6-chloro-3-pyridyl)-2-methyl-2-azabicyclo[2.2.2]oct-5-ene, 7-(6-ethoxypyridin-3-yl)-2-methyl-2-azabicyclo[2.2.2]oct-5-ene, and salts or crystals thereof.

58. A compound as defined in any of items 2 to 57 or a salt or crystal thereof, or a formulation comprising a compound as defined in any of items 2 to 57 or a salt or crystal thereof, for use in the treatment of an ectoparasite infestation, preferably as an ectoparasiticide for the treatment of an ectoparasite infestation.

59. The use according to any one of items 2 to 57 or the compound for use or formulation for use according to item 58, wherein the compound or formulation is for use as an ectoparasiticide.

60. The use according to any one of items 2 to 57 or the compound for use or formulation for use according to item 58, wherein the compound or formulation is for use as a repellent.

61. The use according to any one of items 2 to 57 or the compound for use or formulation for use according to item 58, wherein the formulation or compound is applied in the form of a topical formulation, a shampoo composition, a cleansing composition or a treatment composition.

62. The use or the compound for use or formulation for use according to item 61, wherein the topical formulation, shampoo composition, cleansing composition or treatment composition is in the form of a lotion, cream, ointment, gel, foam, patch, powder, solid, sponge, tape, vapor, paste, tincture, or spray.

63. The use or the compound for use or formulation for use according to item 61 or 62, wherein the formulation or compound is applied to a mammal, in particular a human, dog, cat, cattle, horse or sheep.

64. The use or the compound for use or formulation for use according to item 61 or 62, wherein the formulation or compound is applied to an object or a fabric.

It is to be understood that while the compound of formula (I) has been described in the context of its use, the present disclosure also relates to this compound as such as well as to any specific compounds of formula (I), such as formulae (Ia) to (Ix), as such.

The present invention relates in particular to the compounds, including their salts and solvates:

2-phenyl-5-(1,2,3,6-tetrahydropyridin-2-yl)pyridine
2-chloro-5-(1,2,3,6-tetrahydropyridin-2-yl)pyridine
2,3-dichloro-5-(1,2,3,6-tetrahydropyridin-2-yl)pyridine
3-ethynyl-5-(1,2,3,6-tetrahydropyridin-2-yl)pyridine
2-[5-(1,2,3,6-tetrahydropyridin-2-yl)-3-pyridyl]-2,5-diazabicyclo[2.2.1]heptane
3-[(2S)-4-phenyl-1,2,3,6-tetrahydropyridin-2-yl]pyridine 3-[(2S)-2-(3-pyridyl)-1,2,3,6-tetrahydropyridin-4-yl]pyridine
2-methyl-3-(2-phenyl-5-pyridyl)-2-azabicyclo[2.2.2]octane
5-(2-chloro-5-pyridyl)-2-azabicyclo[2.2.2]oct-5-ene
5-(2-chloro-5-pyridyl)-2-methyl-2-azabicyclo[2.2.2]oct-5-ene
7-(3-pyridyl)-2-azabicyclo[2.2.2]oct-5-ene
7-(2-chloro-5-pyridyl)-2-azabicyclo[2.2.2]oct-5-ene
3-[[(2S)-1,2,3,6-tetrahydropyridin-2-yl]methoxy]pyridine
2-ethynyl-5-[2-(3-pyridyl)-1,2,3,6-tetrahydropyridin-4-yl]pyridine
2-methyl-7-(3-pyridyl)-2-azabicyclo[2.2.2]oct-5-ene
7-(2-chloro-5-pyridyl)-2-methyl-2-azabicyclo[2.2.2]oct-5-ene, and
7-(2-ethoxypyridin-5-yl)-2-methyl-2-azabicyclo[2.2.2]oct-5-ene.

These compounds are more particularly selected from the following:

2-phenyl-5-(1,2,3,6-tetrahydropyridin-2-yl)pyridine dihydrochloride
2-chloro-5-(1,2,3,6-tetrahydropyridin-2-yl)pyridine dihydrochloride
2,3-dichloro-5-(1,2,3,6-tetrahydropyridin-2-yl)pyridine dihydrochloride
3-ethynyl-5-(1,2,3,6-tetrahydropyridin-2-yl)pyridine dihydrochloride
2-[5-(1,2,3,6-tetrahydropyridin-2-yl)-3-pyridyl]-2,5-diazabicyclo[2.2.1]heptane dihydrochloride
3-[(2S)-4-phenyl-1,2,3,6-tetrahydropyridin-2-yl]pyridine dihydrochloride
3-[(2S)-2-(3-pyridyl)-1,2,3,6-tetrahydropyridin-4-yl]pyridine dihydrochloride
2-methyl-3-(2-phenyl-5-pyridyl)-2-azabicyclo[2.2.2]octane hydrochloride
5-(2-chloro-5-pyridyl)-2-azabicyclo[2.2.2]oct-5-ene hydrochloride
5-(2-chloro-5-pyridyl)-2-methyl-2-azabicyclo[2.2.2]oct-5-ene
7-(3-pyridyl)-2-azabicyclo[2.2.2]oct-5-ene
7-(2-chloro-5-pyridyl)-2-azabicyclo[2.2.2]oct-5-ene
3-[[(2S)-1,2,3,6-tetrahydropyridin-2-yl]methoxy]pyridine
2-ethynyl-5-[2-(3-pyridyl)-1,2,3,6-tetrahydropyridin-4-yl]pyridine
2-methyl-7-(3-pyridyl)-2-azabicyclo[2.2.2]oct-5-ene
7-(2-chloro-5-pyridyl)-2-methyl-2-azabicyclo[2.2.2]oct-5-ene, and
7-(2-ethoxypyridin-5-yl)-2-methyl-2-azabicyclo[2.2.2]oct-5-ene.

The present invention also relates to the use of a compound of formula (I) or a salt or crystal thereof for the reduction of infestation with ectoparasites:

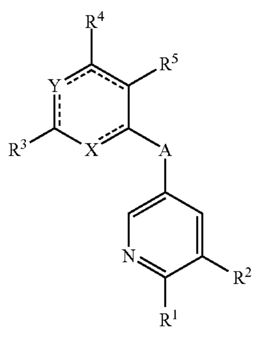

wherein

X is selected from C—$R^7$ and N, if the ===== attached to X is a double bond, or is selected from $C(R^7)_2$ and N—$R^7$, if the ===== attached to X is a single bond, Y is selected from C—$R^8$ and N, if one of the ===== attached to Y is a double bond, or is selected from $C(R^8)_2$ and N—$R^8$, if none of the ===== attached to Y is a double bond, $R^1$ and $R^2$ are each independently selected from hydrogen, halogen, alkyl, haloalkyl, heteroalkyl, alkenyl, alkynyl, optionally substituted cycloalkyl, optionally substituted cycloheteroalkyl, optionally substituted aryl and optionally substituted heteroaryl, $R^3$, $R^4$, $R^5$ are each independently selected from hydrogen, halogen, alkyl, haloalkyl, heteroalkyl, alkenyl, alkynyl, optionally substituted cycloalkyl, optionally substituted cycloheteroalkyl, optionally substituted aryl and optionally substituted heteroaryl, or wherein optionally $R^1$ and $R^4$, or optionally $R^3$ and $R^5$, are taken together to form group Z selected from $—CH_2—$, $—CH_2—CH_2—$, $—CH{=}CH—$, $—CH_2—NR^9$, $—NR^9—CH_2—$, $—CH_2—CH_2—CH_2—$, and $—CH_2—CH_2—NR^9—$, $—NR^9—CH_2—CH_2—$, and $—CH_2—NR^9—CH_2—$, wherein each $R^9$ is independently selected from hydrogen, alkyl, haloalkyl and heteroalkyl, ===== each independently indicates a single bond or a double bond, A is selected from a bond and -L1-L2-L3-L4-, wherein L1 is connected to the ring containing X and Y, wherein L1 is selected from a methylene group which is optionally substituted with halogen, alkyl, haloalkyl and/or heteroalkyl, L2 is selected from a bond, —O— and a methylene group wherein the methylene group is optionally substituted with halogen, alkyl, haloalkyl and/or heteroalkyl, L3 is a bond or a methylene group wherein the methylene group is optionally substituted with halogen, alkyl, haloalkyl and/or heteroalkyl, L4 is a bond or a methylene group wherein the methylene group is optionally substituted with halogen, alkyl, haloalkyl and/or heteroalkyl, $R^7$ and $R^8$ are each independently selected from hydrogen, alkyl, haloalkyl and heteroalkyl, and the optional substituent of the optionally substituted cycloalkyl, optionally substituted cycloheteroalkyl, optionally substituted aryl and optionally substituted heteroaryl is/are each independently selected from halogen, alkyl, haloalkyl and heteroalkyl.

The following definitions apply throughout the present specification, unless specifically indicated otherwise.

As used herein, the terms "optional", "optionally" and "may" denote that the indicated feature may be present but can also be absent. Whenever the term "optional", "optionally" or "may" is used, the present invention specifically relates to both possibilities, i.e., that the corresponding feature is present or, alternatively, that the corresponding feature is absent. For example, the expression "X is optionally substituted with Y" (or "X may be substituted with Y") means that X is either substituted with Y or is unsubstituted. Likewise, if a component of a composition is indicated to be "optional", the invention specifically relates to both possibilities, i.e., that the corresponding component is present (contained in the composition) or that the corresponding component is absent from the composition.

Various groups are referred to as being "optionally substituted" in this specification. Generally, these groups may carry one or more substituents, such as, e.g., one, two, three or four substituents. It will be understood that the maximum number of substituents is limited by the number of attachment sites available on the substituted moiety. Unless defined otherwise, the "optionally substituted" groups referred to in this specification carry preferably not more than two substituents and may, in particular, carry only one substituent. Moreover, unless defined otherwise, it is preferred that the optional substituents are absent, i.e. that the corresponding groups are unsubstituted.

As used herein, the term "halogen" refers to fluoro (—F), chloro (—Cl), bromo (—Br), or iodo (—I).

As used herein, the term "alkyl" refers to a monovalent saturated acyclic (i.e., non-cyclic) hydrocarbon group which may be linear or branched. Accordingly, an "alkyl" group does not comprise any carbon-to-carbon double bond or any carbon-to-carbon triple bond. The term "alkyl" preferably refers to a "$C_{1-6}$ alkyl". A "$C_{1-6}$ alkyl" denotes an alkyl group having 1 to 6 carbon atoms. Preferred exemplary alkyl groups are methyl, ethyl, propyl (e.g., n-propyl or isopropyl), or butyl (e.g., n-butyl, isobutyl, sec-butyl, or tert-butyl). Unless defined otherwise, the term "alkyl" more preferably refers to $C_{1-4}$ alkyl, more preferably to methyl or ethyl, and even more preferably to methyl.

As used herein, the term "haloalkyl" refers to an alkyl group substituted with one or more (preferably 1 to 6, more preferably 1 to 3) halogen atoms which are selected independently from fluoro, chloro, bromo and iodo, and are preferably all fluoro atoms. It will be understood that the maximum number of halogen atoms is limited by the number of available attachment sites and, thus, depends on the number of carbon atoms comprised in the alkyl moiety of the haloalkyl group. "Haloalkyl" may, e.g., refer to $—CF_3$, $—CHF_2$, $—CH_2F$, $—CF_2—CH_3$, $—CH_2—CF_3$, $—CH_2—CHF_2$, $—CH_2—CF_2—CH_3$, $—CH_2—CF_2—CF_3$, or $—CH(CF_3)_2$.

As used herein, the term "heteroalkyl" refers to an alkyl group in which one or two of the $—CH_2—$ groups have been replaced each independently by a group selected from —O—, —S— and —N($C_{1-6}$alkyl)-.

As used herein, the term "alkenyl" refers to a monovalent unsaturated acyclic hydrocarbon group which may be linear or branched and comprises one or more (e.g., one or two) carbon-to-carbon double bonds while it does not comprise any carbon-to-carbon triple bond.

The term "$C_{2-6}$ alkenyl" denotes an alkenyl group having 2 to 6 carbon atoms. Preferred exemplary alkenyl groups are ethenyl, propenyl (e.g., prop-1-en-1-yl, prop-1-en-2-yl, or prop-2-en-1-yl), butenyl, butadienyl (e.g., buta-1,3-dien-1-yl or buta-1,3-dien-2-yl), pentenyl, or pentadienyl (e.g., isoprenyl). Unless defined otherwise, the term "alkenyl" preferably refers to $C_{2-6}$ alkenyl, more preferably $C_{2-4}$ alkenyl.

As used herein, the term "alkynyl" refers to a monovalent unsaturated acyclic hydrocarbon group which may be linear or branched and comprises one or more (e.g., one or two) carbon-to-carbon triple bonds and optionally one or more carbon-to-carbon double bonds. The term "$C_{2-6}$ alkynyl" denotes an alkynyl group having 2 to 6 carbon atoms. Preferred exemplary alkynyl groups are ethynyl, propynyl, or butynyl. Unless defined otherwise, the term "alkynyl" preferably refers to $C_{2-6}$ alkynyl, more preferably $C_{2-4}$ alkynyl.

As used herein, the term "aryl" refers to an aromatic hydrocarbon ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic). "Aryl" may, e.g., refer to phenyl, naphthyl, dialinyl (i.e., 1,2-dihydronaphthyl), tetralinyl (i.e., 1,2,3,4-tetrahydronaphthyl), anthracenyl, or phenanthrenyl. Unless defined otherwise, an "aryl" preferably has 6 to 14 ring atoms, more preferably 6 to 10 ring atoms, and most preferably refers to phenyl.

As used herein, the term "heteroaryl" refers to an aromatic ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic), wherein said aromatic ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). "Heteroaryl" may, e.g., refer to thienyl (i.e., thiophenyl), benzo[b]thienyl, naphtho[2,3-b]thienyl, thianthrenyl, furyl (i.e., furanyl), benzofuranyl, isobenzofuranyl, chromenyl, xanthenyl, phenoxathiinyl, pyrrolyl (e.g., 2H-pyrrolyl), imidazolyl, pyrazolyl, pyridyl (i.e., pyridinyl; e.g., 2-pyridyl, 3-pyridyl, or 4-pyridyl), pyrazinyl, pyrimidinyl, pyridazinyl, indolizinyl, isoindolyl, indolyl (e.g., 3H-indolyl), indazolyl, purinyl, isoquinolyl, quinolyl, phthalazinyl, naphthyridinyl, quinoxalinyl, cinnolinyl, pteridinyl, carbazolyl, beta-carbolinyl, phenanthridinyl, acridinyl, perimidinyl, phenanthrolinyl (e.g., [1,10]phenanthrolinyl, [1,7]phenanthrolinyl, or [4,7]phenanthrolinyl), phenazinyl, thiazolyl, isothiazolyl, phenothiazinyl, oxazolyl, isoxazolyl, furazanyl, phenoxazinyl, pyrazolo[1,5-a]pyrimidinyl (e.g., pyrazolo[1,5-a]pyrimidin-3-yl), 1,2-benzoisoxazol-3-yl, benzothiazolyl, benzoxazolyl, benzisoxazolyl, benzimidazolyl, 1H-tetrazolyl, 2H-tetrazolyl, coumarinyl, or chromonyl. Unless defined otherwise, a "heteroaryl" preferably refers to a 5 to 14 membered (more preferably 5 to 10 membered) monocyclic ring or fused ring system comprising one or more (e.g., one, two, three or four) ring heteroatoms independently selected from O, S and N, wherein one or more S ring atoms (if present) and/or one or more N ring atoms (if present) are optionally oxidized, and wherein one or more carbon ring atoms are optionally oxidized; even more preferably, a "heteroaryl" refers to a 5 or 6 membered monocyclic ring comprising one or more (e.g., one, two or three) ring heteroatoms independently selected from O, S and N, wherein one or more S ring atoms (if present) and/or one or more N ring atoms (if present) are optionally oxidized, and wherein one or more carbon ring atoms are optionally oxidized. A particularly preferred example of the term "heteroaryl" is pyridiyl.

As used herein, the term "cycloalkyl" refers to a saturated hydrocarbon ring group, including monocyclic rings as well as bridged ring, spiro ring and/or fused ring systems (which may be composed, e.g., of two or three rings; such as, e.g., a fused ring system composed of two or three fused rings). "Cycloalkyl" may, e.g., refer to cyclopropyl, cyclobutyl, cyclopentyl, cyclohexyl, cycloheptyl, or adamantyl. Unless defined otherwise, "cycloalkyl" preferably refers to a $C_{3-11}$ cycloalkyl, and more preferably refers to a $C_{3-8}$ cycloalkyl.

A particularly preferred "cycloalkyl" is a monocyclic saturated hydrocarbon ring having 3 to 8 ring members.

As used herein, the term "cycloheteroalkyl" (which may also be referred to as "heterocycloalkyl") refers to a saturated ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). "Cycloheteroalkyl" may, e.g., refer to oxetanyl, tetrahydrofuranyl, piperidinyl, piperazinyl, aziridinyl, azetidinyl, pyrrolidinyl, imidazolidinyl, morpholinyl (e.g., morpholin-4-yl), pyrazolidinyl, tetrahydrothienyl, octahydroquinolinyl, octahydroisoquinolinyl, oxazolidinyl, isoxazolidinyl, azepanyl, diazepanyl, oxazepanyl or 2-oxa-5-aza-bicyclo[2.2.1]hept-5-yl. Unless defined otherwise, "cycloheteroalkyl" preferably refers to a 3 to 11 membered saturated ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, and wherein one or more carbon ring atoms are optionally oxidized; more preferably, "cycloheteroalkyl" refers to a 5 to 8 membered saturated monocyclic ring group containing one or more (e.g., one, two, or three) ring heteroatoms independently selected from O, S and N, wherein one or more S ring atoms (if present) and/or one or more N ring atoms (if present) are optionally oxidized, and wherein one or more carbon ring atoms are optionally oxidized.

As used herein, the term "are taken together" means that two groups are combined to represent a single group. It is to be understood that this single group will be a divalent group. Accordingly, the term "$R^3$ and $R^5$ are taken together to form group Z" preferably indicates that $R^3$ and $R^5$ are (theoretically) linked to form a divalent group (—$R^3$-$R^5$—), wherein the (theoretical) divalent group (—$R^3$-$R^5$—) is then replaced by Z. In other words, the divalent group Z binds with one bond to the carbon to which $R^3$ was attached and with the other bond to the carbon to which $R^5$ was attached.

The present invention furthermore relates to such compounds and formulations containing such compounds for use in the treatment of an ectoparasite infestation.

The ectoparasites is preferably from the insect class, including fleas and mosquitoes and/or from the arachnid class, including ticks and mites. It is preferably from the insect class, more preferably fleas and mosquitoes, even more preferably mosquitoes.

The optional substituent of the optionally substituted cycloalkyl, optionally substituted cycloheteroalkyl, optionally substituted aryl (including optionally substituted phenyl) and optionally substituted heteroaryl (including optionally substituted pyridyl) is/are each independently selected from halogen, alkyl, haloalkyl and heteroalkyl. Preferably, the optional substituent of the optionally substituted cycloalkyl, optionally substituted cycloheteroalkyl, optionally substituted aryl (including optionally substituted phenyl) and optionally substituted heteroaryl (including optionally substituted pyridyl) is/are each independently selected from halogen, alkyl and heteroalkyl, more preferably halogen, methyl, methoxy and ethyl, even more preferably halogen.

The following compounds are preferably excluded:

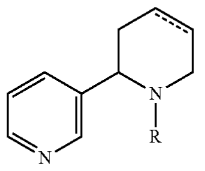

wherein

R represents hydrogen or $C_1$-$C_5$ alkyl, and

----- represents a single or double bond.

Preferably, the ring containing X and Y contains only one or two double bonds, preferably one double bond. It is to be understood that the double bound which may be present in Z is not taken into account in this number of double bonds.

If the ----- attached to X is a double bond, X is preferably selected from C—$R^7$. Likewise, if one of the ----- attached to Y is a double bond, Y is preferably selected from C—$R^8$.

Specific examples of the compound of formula (I) are represented by the following formulae (Ia) to (Ix), wherein $R^1$, $R^2$, $R^3$, $R^4$, $R^5$, $R^7$, $R^8$, $R^9$, A, X, Y and Z are as defined above, and ----- indicates a single bond or a double bond:

(Ia)

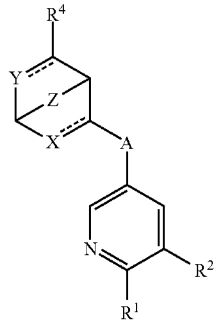

(Ib)

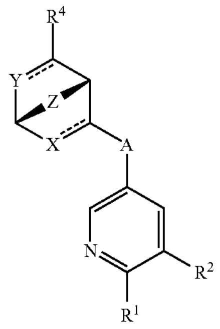

-continued
(Ic)
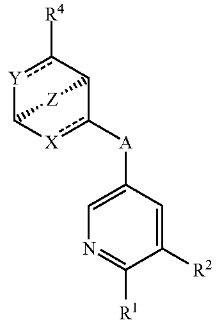
(Id)
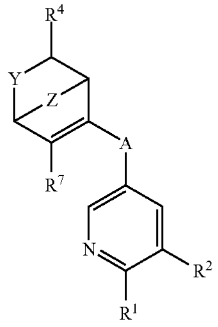
(Ie)
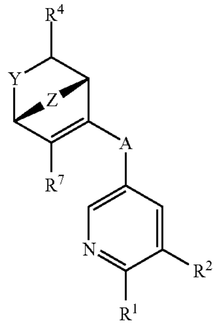
(If)
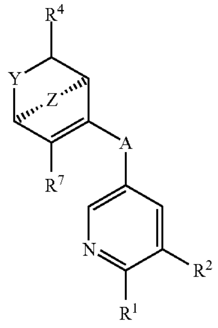
(Ig)
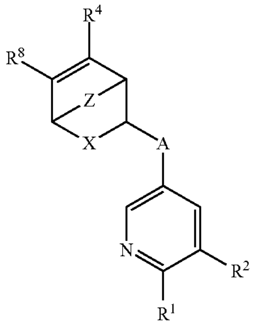
-continued
(Ih)
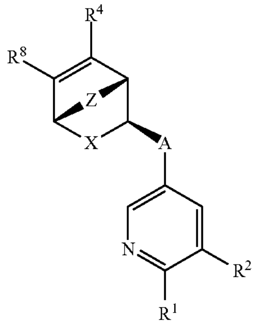
(Ii)
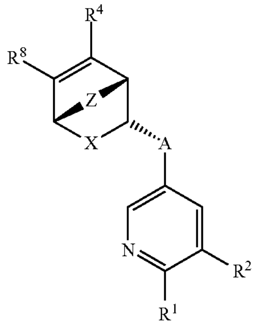
(Ij)
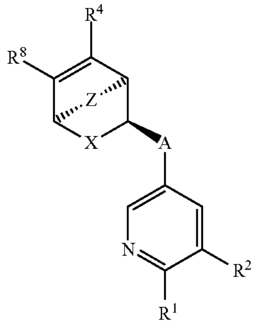
(Ik)
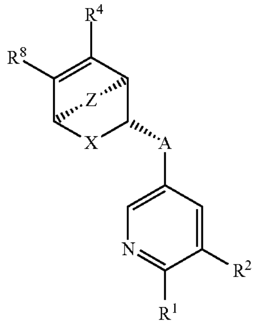
(Il)
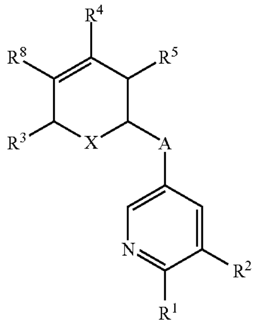

-continued
(Im)
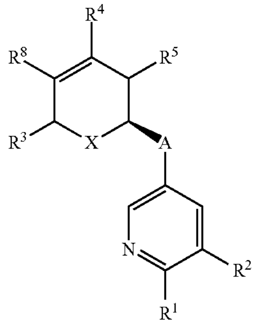
(In)
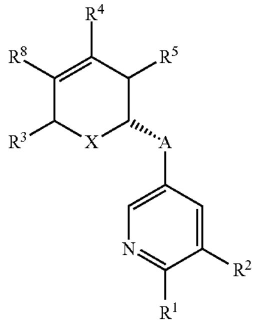
(Io)
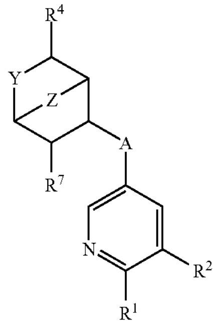
(Ip)
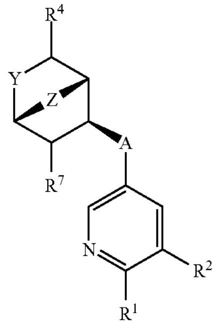
(Iq)
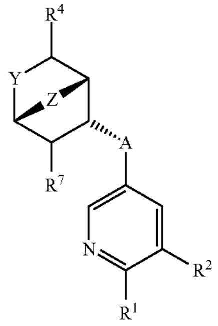
-continued
(Ir)
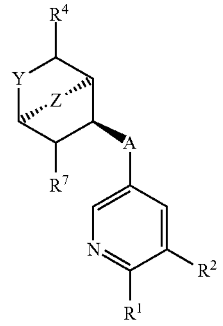
(Is)
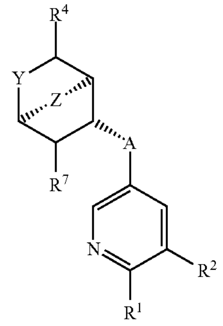
(It)
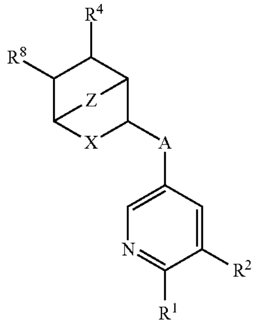
(Iu)
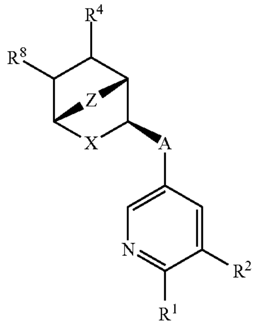
(Iv)
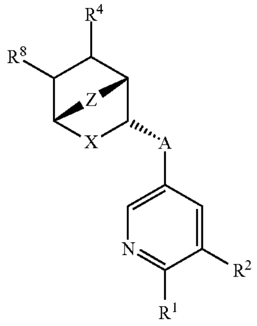

-continued (Iw)

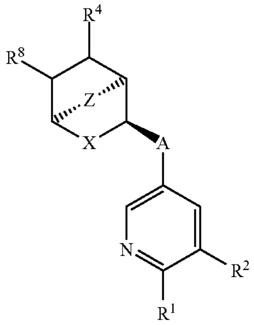

(Ix)

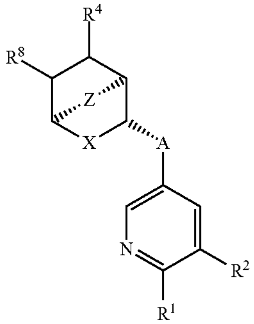

With respect to these compounds it is to be understood that any substituent not explicitly referred to is considered defined as set out above with respect to the compound of formula (I), and as set out in preferred embodiments in the following.

It is preferred that $R^1$ is selected from hydrogen, halogen, alkyl, haloalkyl, heteroalkyl, alkynyl, optionally substituted cycloalkyl, optionally substituted cycloheteroalkyl and optionally substituted aryl. More preferably, $R^1$ is selected from hydrogen, halogen, heteroalkyl and aryl. Even more preferably, $R^1$ is selected from hydrogen, halogen, —O-alkyl and phenyl.

$R^2$ is preferably selected from hydrogen, halogen, alkyl, haloalkyl, heteroalkyl, alkynyl, optionally substituted cycloalkyl, optionally substituted cycloheteroalkyl and optionally substituted aryl. More preferably, $R^2$ is selected from hydrogen, halogen, alkyl, haloalkyl, heteroalkyl, alkynyl, optionally substituted cycloalkyl and optionally substituted cycloheteroalkyl. Even more preferably, $R^2$ is selected from hydrogen, halogen, alkynyl and optionally substituted cycloheteroalkyl.

It is preferred that Z is selected from $—CH_2—CH_2—$, —CH═CH—, $—CH_2—NR^9$, $—NR^9—CH_2—$, $—CH_2—CH_2—CH_2—$, $—CH_2—CH_2—NR^9—$, $—NR^9—CH_2—CH_2—$, and $—CH_2—NR^9—CH_2—$. More preferably, Z is selected from $—CH_2—CH_2—$, —CH═CH—, $—CH_2—NR^9$ and $—NR^9—CH_2—$. Still more preferably, Z is $—CH_2—CH_2—$. In other embodiments, in particular if Y is N or $NR^9$, it is preferred that Z is —CH═CH—.

L1 is preferably selected from a methylene group which is optionally substituted with halogen and/or alkyl. More preferably, L1 is selected from a methylene group which is optionally substituted with halogen and/or methyl. Even more preferably L1 is a methylene group.

It is furthermore contemplated that L1 may be a carbonyl group.

It is preferred that L2 is selected from a bond, —O— and a methylene group wherein the methylene group is optionally substituted with halogen and/or alkyl. More preferably, L2 is selected from a bond and —O—. Even more preferably, L2 is a bond.

It is furthermore contemplated that L2 may be an —N(H)— or $—N(C_{1-6}alkyl)-$ group.

L3 is preferably selected from a bond or a methylene group which is optionally substituted with halogen and/or methyl. More preferably, L3 is a bond.

L4 is preferably selected from a bond or a methylene group which is optionally substituted with halogen and/or methyl. More preferably, L4 is a bond.

It is preferred that L3 and L4 are each a bond. In other words, it is preferred that A corresponds to -L1-L2-.

It is particularly preferred that A is a bond or $—CH_2—O—$ wherein the $—CH_2$ group binds to the ring containing X and Y as shown in formula (I).

It is preferred that $R^7$ is selected from hydrogen, alkyl, haloalkyl and heteroalkyl. More preferably, $R^7$ is selected from hydrogen, alkyl and haloalkyl. Even more preferably, $R^7$ is hydrogen or methyl.

$R^8$ is preferably selected from hydrogen, alkyl, haloalkyl and heteroalkyl. More preferably, $R^8$ is selected from hydrogen, alkyl and haloalkyl. Still more preferably, $R^8$ is hydrogen or methyl.

It is preferred that each $R^9$ is independently selected from hydrogen, alkyl, haloalkyl and heteroalkyl. More preferably, each $R^9$ is independently selected from hydrogen, alkyl and haloalkyl. Even more preferably, each $R^9$ is independently selected from hydrogen and methyl.

The inventors have surprisingly and unexpectedly found that compounds of Formula I have an improved effect in the reduction of infestation with ectoparasites, in particular ectoparasites from the insect class, including fleas and mosquitoes and/or from the arachnid class, particularly ticks and mites, in particular in the reduction of infestation with mosquitoes and ticks. As shown in the appended Examples, the effect of compounds of Formula I is particularly improved over the effect of nicotine, which is considered in the prior art as the most effective repellent comprised in tobacco extracts. It is also assumed that the compounds are less toxic than insecticides used for protection from ectoparasites, in particular the compounds are less irritating to the skin.

Within the present invention, reducing the infestation with ectoparasites may be achieved through the repelling activity of the formulation or compound of the invention and/or the killing activity of the formulation or compound of the invention. As such, the formulations or compounds of the invention may have both repelling and killing activity or repelling or killing activity against ectoparasites such as insects including fleas and mosquitoes and/or arachnids, particularly ticks and mites, but in particular against mosquitoes. Repelling and/or killing activity may be determined using methods provided herein, in particular methods as employed herein below in the examples section. It is preferred within the present invention that a reduction of infestation of at least 30%, 35%, 40%, 45%, 50%, 55%, 60%, 65%, 70%, 75%, 80%, 85%, 90%, 95% or 100% is achieved, when preferably compared to a control without an active ingredient and applying the identical assay method.

In a further embodiment, the present invention relates to the use of a compound of Formula I, or a salt or crystal thereof for the control of ectoparasites, in particular ectoparasites of the insect class, including fleas and mosquitoes and/or of the arachnid class, including ticks and mites, particularly ticks, etc., but preferably for the control of insects, more preferably for the control of ticks and mosquitoes.

The compound as used herein or as comprised in the formulation of the invention can be in pure form or combined with, for example, a suitable excipient or additive.

In a more particularly preferred embodiment of the invention, the compound is a racemate or one enantiomeric form may be present in enantiomeric excess. Accordingly, the compound present in the invention may be S- or R- or it may be present at any ratio between both enantiomeric forms.

Within the present invention, the compound of Formula I or the formulation of the invention may be applied in the form of a topical formulation.

The skilled person is aware of various topical formulations. Within the present invention, it is however preferred that the topical formulation is in the form of a lotion, cream, ointment, gel, foam, patch, powder, solid, sponge, tape, vapor, paste or tincture. The topical formulation can furthermore preferably be selected from liquid formulations, such as pour on, spot on and spray formulations.

Accordingly, in one embodiment of the invention, the compound is applied on the skin of a mammal, in particular a human, dog, cat, cattle, or horse.

While the compound or formulation of the invention is effective against a wide range of parasites, it is preferred within the present invention that the parasite is an ectoparasite, in particular an ectoparasite from the phylum arthropoda, more particularly an ectoparasite from the insect class, including fleas and mosquitoes and/or from the arachnid class, particularly ticks and mites, but preferably the ectoparasite is a tick or a mosquito.

Accordingly, in one embodiment of the invention, the use of the compound or formulation of the invention as an insecticide or an ectoparasiticide is provided.

In a further embodiment of the invention, the use of the compound or formulation of the invention as an insect repellent a tick repellent or an ectoparasite repellent is provided.

Further aspects and embodiments of the present invention will be become apparent as this description continues.

Unless defined otherwise, all technical and scientific terms used herein have the same meanings as commonly understood by one of ordinary skill in the art to which this invention belongs.

The term "about" where used to characterize an enantiomeric excess means±4% referring to the given numeric value, if not indicated otherwise. In each of the invention embodiments, "about" can be deleted.

The term "preferably" is used to describe features or embodiments which are not required in the present invention but may lead to improved technical effects and are thus desirable but not essential.

With respect to the numerical values mentioned herein, unless explicitly stated otherwise, the last decimal place of a numerical value preferably indicates its degree of accuracy. Thus, unless other error margins are given, the maximum margin is preferably ascertained by applying the rounding-off convention to the last decimal place. Thus, a value of 2.5 preferably has an error margin of 2.45 to 2.54.

In the following, unless stated otherwise, references concerning the compound of Formula I are deemed to also relate to the compound of Formula Ia, Ib, etc. In the context of the use according to the present invention, however, references concerning the compound of Formula I, are to be understood as relating to the compound of Formula I in general, including any salts or crystals thereof, and preferably to the compound of Formula Ia, Ib, etc.

As the skilled person is aware, compounds of formula (I) can be present in two enantiomeric forms, S and R. The compound of Formula I of the present invention may be present at any overall range of ratios of R and S, alternatively expressed as the enantiomeric excess of (R), which has been surprisingly shown to be even more effective than S.

It is to be understood that the "ratio" of R and S as used herein refers to the weight ratio of R and S, unless explicitly stated otherwise. If solvates of R and/or S are used, the solvent is thus to be disregarded in this calculation. In other words, the "ratio of R and S is calculated as follows:

$$\text{Ratio of } R \text{ and } S = \frac{\text{amount of } R \text{ by weight}}{\text{amount of } S \text{ by weight}}$$

As known by the skilled person in the art, the ratio of compounds differing only in chirality, such as in the case of R and S, can be determined in a number of ways known in the art, including but not limited to chromatography using a chiral support, polarimetric measurement of the rotation of polarized light, nuclear magnetic resonance spectroscopy using chiral shift reagents, or derivatization of a compound using a chiral compound such as Mosher's acid followed by chromatography or nuclear magnetic resonance spectroscopy. Enantiomers can further be isolated from mixtures by methods known to those skilled in the art, including chiral high-pressure liquid chromatography (HPLC) and direct fractional crystallization of the racemate, i.e., by chiral co-crystallization techniques, which exploit the formation of specific hydrogen bonding interactions present in co-crystals (see Springuel G R, et al., 2012; and U.S. Pat. No. 6,570,036). Useful co-crystallization partners include enantiomers of mandelic acid, malic acid, tartaric acid and its derivatives; or enantiomers can be prepared by asymmetric syntheses. See, for example, Eliel and Wilen, 1994.

The ratio of R and S (which may also be referred to as the chiral purity) of the inventive composition can also be expressed in terms of its enantiomeric excess (ee), typically and preferably as determined by chiral HPLC, and calculated by the equation:

$$ee=(A_R-A_S)/(A_R+A_S)\times 100\%,$$

wherein $A_R$ is the area of the peak of R and $A_S$ is the area of the peak of S, in the HPLC chromatogram of the sample solution.

The compound of Formula Ia may be present in the formulation of the invention or in the uses provided herein as a solvate or co-crystal.

In this respect, within the present invention, a "solvate" refers to an association or complex of one or more solvent molecules and either the R or S. Examples of solvents that form solvates include, but are not limited to, water, isopropanol, ethanol, methanol, dimethyl sulfoxide (DMSO), ethyl acetate, acetic acid, and ethanolamine. The term "hydrate" refers to the complex where the solvent molecule is water.

A "co-crystal" refers to a crystalline structure that contains at least two different compounds that are solid in their pure form under ambient conditions. The at least two different compounds may include R and/or S and/or any further components of the composition or formulation provided herein. Co-crystals are made from neutral molecular species, and all species remain neutral after crystallization; further, typically and preferably, they are crystalline homogeneous phase materials where two or more building compounds are present in a defined stoichiometric ratio. See hereto Wang Y and Chen A, 2013; and Springuel G R, et al., 2012; and U.S. Pat. No. 6,570,036. It is to be understood that the R and S may be in the form of any polymorph. A variety of co-crystals and techniques for preparing such co-crystals are described in RSC Drug Discovery, Pharmaceutical Salts and Co-crystals, published in 2012 by the Royal Society of Chemistry and edited by Johan Wouters and Luc Quéré, in particular in chapters 15 and 16. Preferred examples of the co-crystal formers are those disclosed in Table 16.1 of this reference. Even more preferred co-crystals include co-crystals of α-hydroxy acids, α-keto acids and/or α-keto amides with the enantiomers in the (R) to (S)-ratios as disclosed herein. Examples of α-hydroxy acids include atrolactic acid, benzilic acid, 4-chloromandelic acid, citric acid, 3,4-dihydroxymandelic acid, ethyl pyruvate, galacturonic acid, gluconolactone, glucuronic acid, glucuronolactone, glycolic acid, 2-hydroxybutanoic acid, 2-hydroxypentanoic acid, 2-hydroxyhexanoic acid, 2-hydroxyheptanoic acid, 2-hydroxyactanoic acid, 2-hydroxynonanoic acid, 2-hydroxydecanoic acid, 2-hydroxyundecanoic acid, 4-hydroxymandelic acid, 3-hydroxy-4-methoxymandelic acid, 4-hydroxy-3-methoxymandelic acid, α-hydroxyarachidonic acid, α-hydroxybutyric acid, α-hydroxyisobutyric acid, α-hydroxylauric acid, α-hydroxymyristic acid, α-hydroxypalmitic acid, α-hydroxystearic acid, 3-(2'-hydroxyphenyl)lactic acid, 3-(4'-hydroxyphenyl)lactic acid, lactic acid, malic acid, mandelic acid, methyllactic acid, methylpyruvate, mucic acid, α-phenylacetic acid, α-phenylpyruvic acid, pyruvic acid, saccharic acid, tartaric acid and tartronic acid. Examples of α-keto acids include 2-ketoethanoic acid (glyoxylic acid), methyl 2-ketoethanoate, 2-ketopropanoic acid (pyruvic acid), methyl 2-ketopropanoate(methyl pyruvate), ethyl 2-ketopropanoate (ethyl pyruvate), propyl 2-ketopropanoate (propyl pyruvate), 2-phenyl-2-ketoethanoic acid (benzoylformic acid), methyl 2-phenyl-2-ketoethanoate (methyl benzoylformate), ethyl 2-phenyl-2-ketoethanoate (ethyl benzoylformate), 3-phenyl-2-ketopropanoic acid (phenylpyruvic acid), methyl 3-phenyl-2-ketopropanoate (methyl phenylpyruvate), ethyl 3-phenyl-2-ketopropanoate (ethyl phenylpyruvate), 2-ketobutanoic acid, 2-ketopentanoic acid, 2-ketohexanoic acid, 2-ketoheptanoic acid, 2-ketooctanoic acid, 2-ketododecanoic acid and methyl 2-ketooctanoate. Examples of α-keto amides include any compounds obtainable by reacting any one of the above examples of α-keto acids with primary or secondary amines.

The compound or formulation of the invention is also provided for use in the control of insects and/or arachnids that are parasites, particularly for use in the control of insects and/or arachnids that are of ectoparasites, particularly for the reduction of infestation with the same. Accordingly, the present invention, inter alia, relates to the use of the compound or formulation provided herein for reducing infestation with ectoparasites, in particular ectoparasites from the phylum arthropoda, more particularly an ectoparasite from the insect class, including fleas and mosquitoes and/or from the arachnid class, particularly mites, including ticks, etc., but preferably for reducing infestation with mosquitoes.

In the context of the present invention, insects may be in particular mosquitoes. In particular, the term mosquitoes in understood to include members of the family Culicidae, including the subfamilies Anophelinae and Culicinae. However, within the invention the term "insects" includes insects of the order: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera. However, the invention relates in particular to those which trouble humans or animals and carry pathogens, for example flies such as *Musca domestica, Musca vetustissima, Musca autumnalis, Fannia canicularis, Sarcophaga carnaria, Lucilia cuprina, Hypoderma bovis, Hypoderma lineatum, Chrysomyia chloropyga, Dermatobia hominis, Cochliomyia hominivorax, Gasterophilus intestinalis, Oestrus ovis, Stomoxys calcitrans, Haematobia irritans* and *Nematocera*, such as mosquitoes (Culicidae), including the genera *Aedes, Anopheles, Culex*, and *Ochlerotatus*, midges (Ceratopogonidae, Simuliidae, and Psychodidae), including the *Phlebotoma* and *Lutzomyia* genera, for example fleas (Siphonaptera), such as *Ctenocephalides felis* and *Ctenocephalides canis* (cat and dog fleas), *Xenopsylla cheopis, Pulex irritans, Dermatophilus penetrans*, blood-sucking lice (Anoplura), such as *Hematopinus* spp, *Solenopotes* spp, *Linognathus* spp, *Pediculus humanis*, chewing-lice (mallophaga), such as *Bovicola* (*Damalina*) *ovis* and *Bovicola bovis*, biting flies and horse-flies (Tabanidae), *Haematopota* spp. such as *Haematopota pluvialis*, Tabanidae spp. such as *Tabanus nigrovittatus*, Chrysopsinae spp. such as *Chrysops caecutiens*, tsetse flies, such as species of *Glossinia*, nuisance insects, particularly cockroaches, such as *Blatella germanica, Blatta orientalis*, and *Periplaneta americana.*

In the context of the present invention, ectoparasites of the arachnid class may be in particular ectoparasites of the order Acarina, including mites and ticks. Representatives of mites are, for example, *Dermanyssus gallinae, Sarcoptes scabiei, Psoroptes ovis* and *Psorergates* spp. Known representatives of ticks are, for example, *Boophilus, Amblyomma, Anocentor, Dermacentor, Haemaphysalis, Hyalomma, Ixodes, Rhipicentor, Margaropus, Rhipicephalus, Argas, Otobius* and *Ornithodoros* and the like, which preferably infest warm-blooded animals including farm animals, such as cattle, horses, pigs, sheep and goats, poultry such as chickens, turkeys and geese, fur-bearing animals such as mink, foxes, chinchillas, rabbits and the like, as well as companion animals such as cats and dogs, but also humans.

Ticks may be divided into hard and soft ticks. Hard ticks are characterised by infesting one, two or three host animals. They attach themselves to a passing host animal and suck the blood or body fluids. Fully engorged female ticks drop from the host animal and lay large amounts of eggs (2000 to 3000) in a suitable crack in the floor or in any other protected site where the larvae hatch. These in turn seek a host animal, in order to suck blood from it. Larvae of ticks which only infest one host animal moult twice and thus become nymphs and finally adult ticks without leaving the host they have selected. Larvae of ticks which infest two or three host animals leave the animal after feeding on the blood, moult in the local environment and seek a second or third host as nymphs or as adult ticks, in order to suck its blood.

Ticks are responsible world-wide for the transmission and spread of many human and animal diseases. Because of their economic influence, the most important tick genera are *Boophilus, Rhipicephalus, Ixodes, Hyalomma, Amblyomma* and *Dermacentor*. They are carriers of viral, bacterial (including *Rickettsia* and *Spyrochetes*) and protozoal diseases and cause tick-paralysis and tick-toxicosis. Even a single tick can cause paralysis whereby its saliva penetrates into the host animal during ingestion. Diseases caused by ticks are usually transmitted by ticks, which infest several host animals. Such diseases, for example anaplasmosis, ehrlichiosis, babesiosis, theileriosis and heart water disease, are responsible for the death or impairment of a large number of domestic and farm animals in the entire world. In many countries of temperate climate, ticks of the genus *Ixodes* transmit the agent of the chronically harmful Lyme's disease from wild animals to humans. Apart from the transmission of disease, the ticks are responsible for great economic losses in livestock production. Losses are not confined to the death of the host animals, but also include damage to the pelts, loss of growth, a reduction in milk production and reduced value of the meat. Although the harmful effects of a tick infestation on animals have been known for years, and enormous progress has been made using tick-control programmes, until now no completely satisfactory methods of controlling or eliminating these parasites have been found, and in addition, ticks have often developed resistance to chemical active ingredients.

The infestation of fleas on domestic animals and pets likewise still represents for the owner a problem which has not been satisfactorily resolved or can only be resolved at considerable expense. As with ticks, fleas are not only troublesome, but are carriers of disease. For example, to be mentioned here is Flea Atopic dermatitis (FAD), a serious skin disease in dogs, which is difficult to treat. Fleas can transmit various fungal diseases from host animal to host animal and to the animal keeper, particularly in moist, warm climatic areas, for example in the Mediterranean, in the southern part of USA, etc. Those at risk in particular are people with a weakened immune system or children whose immune system has not yet fully developed. Owing to their complex life cycle, none of the known methods for the control of fleas is completely satisfactory, especially as most known methods are basically directed towards the control of adult fleas in the pelt, and leave completely untouched the different juvenile stages of the fleas, which exist not only in the pelt of the animal, but also on the floor, in carpets, in the bedding of the animal, on chairs, in the garden and all other places with which the infested animal comes into contact. Flea treatment can be expensive and has to be continued over long periods of time.

Besides being a real nuisance in many parts of the world, mosquitoes are the most important and deadly vectors of human and animal diseases: viruses (i.e. Zika, dengue, chikungunya, West Nile, yellow fever), protozoans (malaria plasmodium), and filarial nematodes (dog heartworm, human lymphatic filariasis). Avoiding mosquito bites by treating human, animals, households with insecticides or repellents is therefore the best method for the prevention of mosquito borne diseases. Extensive programs for the control of mosquito populations have been put in place that are nowadays less efficient due to the wide spreading of resistance to current insecticides among mosquito populations.

Mosquitoes are known to function as vectors, or transmitters, of infectious disease in both animals and humans.

Disease organisms transmitted by mosquitoes include, for example, West Nile virus, Saint Louis encephalitis virus, Eastern equine encephalomyelitis virus, Everglades virus, Highlands J virus, La Crosse Encephalitis virus in the United States; dengue fever, yellow fever, Ilheus virus, malaria, Zika virus and filariasis in the American tropics; Rift Valley fever, *Wuchereria bancrofti*, Japanese encephalitis, chikungunya and filariasis in Africa and Asia; and Murray Valley encephalitis in Australia.

Depending on the situation, source reduction, biocontrol, larviciding (killing of larvae), or adulticiding (killing of adults) may be used to manage mosquito populations. These techniques are accomplished using habitat modification, pesticide, biological-control agents, and trapping.

Success usually depends on treating not only the infested animal, e.g. the human, dog, cat, cattle, horse, but at the same time all the locations which the infested animal frequents.

Such a complicated procedure is unnecessary with the present compounds of formula (I), since a particular advantage of the compounds of formula I under discussion is that they are extremely effective and at the same time of very low toxicity for the warm-blooded animals.

The compounds of formula (I) according to the present invention may be mixed with other substances having the same sphere of activity or with parasiticides or with other activity-improving substances to achieve further improved or longer-lasting action, and then applied.

Since the active ingredients are in many instances applied to warm-blooded animals and of course come into contact with the skin, suitable formulation excipients are the excipients and administration forms that are known in cosmetics. They may be administered in the form of solutions, emulsions, ointments, creams, pastes, powders, sprays, etc.

The compounds of formula (I) according to the present invention may be formulated for application to the animal by any technique suitable for topical administration, including a spraying, dipping, or a pour-on technique. Further preferred application techniques include slow release devices, such as bracelet, collars or ear tags (for cattle) aiming at providing long lasting protection against ectoparasites.

The compounds of formula (I) according to the present invention is preferably applied externally to the skin of the animal using an applicator device, such as a gun, spray, or the animal is submerged in a bath of the dip formulation.

In particular, suitable formulations may be applied in a liquid form or an aerosol form. The aerosol form may use a liquid or a gas as a propellant. These include, for example, conventional propellant gases required for spray cans, such as propane, butane, dimethyl ether, $CO_2$, or halogenated lower alkyl gases (for example, halogenated $C_1$-$C_4$ alkyls), and mixtures of two or more thereof.

In particular, the compounds of formula (I) according to the present invention is formulated such that they can be sprayed directly in an area of infestation or they can be bound to a solid support or encapsulated in a time release material.

The solid support may be provided in form of collars, which are designed to combat common external parasites on companion animals. These collars typically consist of a matrix, usually of a matrix of a plastics material containing between 5 and 40% of an active substance and allow a release of the active ingredient over an extended time. These collars therefore ensure a long-lasting protection against ectoparasites.

For administration to farm animals or pets, such as cows, horses, asses, camels, dogs, cats, poultry, sheep, goats, etc., the so-called 'pour-on' or 'spot-on' formulations are also suitable; these liquid or semi-liquid formulations have the advantage that they only have to be applied to a small area of the pelt or plumage, and, thanks to the proportion of spreading oils or other spreading additives, they disperse by themselves over the whole pelt or plumage, without having to do anything else, and become active over the whole area.

Of course, inanimate materials, for example clothing or dog and cat baskets, stables, carpets, curtains, living quarters, conservatories, etc. may be treated with said formulations and thus protected from parasite infestation.

For application on humans, a pleasant-smelling essence, e.g. a perfume, can be added to make application more attractive.

In a preferred embodiment of the present invention, the compound of the invention or the formulation of the invention is applied in the form of a topical formulation.

Thus, in accordance with the present invention, a formulation is provided comprising a compound of Formula I.

In certain embodiments the compound of Formula I may be placed in liposomes. In accordance with the present invention, any phospholipid and/or phospholipid derivative such as a lysophospholipid may be utilized to form a liposome for encapsulating the compound of Formula I. Suitable phospholipids and/or phospholipid derivatives include, but are not limited to, lecithin, lysolecithin, phosphatidylcholine, phosphatidylethanolamine, phosphatidylinositol, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, combinations thereof, and the like.

In some embodiments, a lecithin derived from egg or soybean may be utilized as the phospholipid. Such lecithins include those commercially available as PHOSPHOLIPON® 85G (purified soybean lecithin), PHOSPHOLIPON® 90G (soybean phosphatidylcholine, granulated), and PHOSPHOLIPON® 90H (the fully hydrogenated version of PHOSPHOLIPON® 90G) from American Lecithin Company, Oxford, CT. Other suitable lecithins include LECINOL S-10® lecithin (purified hydrogenated soy lecithin) from Nikko Chemicals.

The above phospholipids or derivatives thereof may be utilized to form liposomes containing the compound of Formula I or alternative formulations comprising Formula I. In embodiments, a lecithin having a high phosphatidylcholine content may be utilized to form a liposome. In some embodiments a high phosphatidylcholine lecithin which may be utilized includes PHOSPHOLIPON® 85G, a soy-derived lecithin containing a minimum of about 85% of a linoleic acid based-phosphatidylcholine. This lecithin is easy to use and is able to produce submicron liposomes at low process temperatures (from about 20° C. to about 55° C.) without the addition of any other special additives. PHOSPHOLIPON® 85G contains, in addition to phosphatidylcholine, approximately 5-7% phosphatidic acid. The phosphatidic acid confers a negative surface charge to the resulting formulations, reduces processing time and process energy, and aids in the formation of stable forms.

In some embodiments, additional components may be combined with the formulation to improve overall rheological and processing properties, and to insure microbiological integrity during storage. Such components include, without limitation, absorbents, antifoaming agents, acidifiers, alkalizers, buffers, antimicrobial agents, antioxidants (for example tocopherols, BHT, polyphenols, phytic acid) binders, biological additives, chelating agents (for example, disodium EDTA, tetrasodium EDTA, sodium metasilicate, and the like), denaturants, preservatives (for example imidazolidinyl urea, diazolidinyl urea, phenoxyethanol, methylparaben, ethylparaben, propylparaben, and the like), reducing agents, solubilizing agents, solvents, viscosity modifiers, humectants, thickening agents, and combinations thereof. These additional components may be present in an amount from about 0.001% by weight to about 10% by weight of the dispersion, in embodiments from about 0.1% by weight to about 1% by weight of the dispersion.

Examples of suitable humectants which may be added to the formulation include, but are not limited to, polyols and polyol derivatives, including glycerol, diglycerol, triglycerol, ethylene glycol, propylene glycol, butylene glycol, pentylene glycol (sometimes referred to herein as 1,2-pentane diol), isopreneglycol (1,4-pentane diol), 1,5-pentane diol, hexylene glycol, erythritol, 1,2,6-hexanetriol, polyethylene glycols such as PEG-4, PEG-6, PEG-7, PEG-8, PEG-9, PEG-10, PEG-12, PEG-14, PEG-16, PEG-18, PEG-20, combinations thereof, sugars and sugar derivatives (including fructose, glucose, maltose, maltitol, mannitol, inositol, sorbitol, sorbityl silanediol, sucrose, trehalose, xylose, xylitol, glucuronic acid and salts thereof), ethoxylated sorbitol (Sorbeth-6, Sorbeth-20, Sorbeth-30, Sorbeth-40), and combinations thereof. In some embodiments, a commercially available 1,2-pentane diol such as HYDROLITE-5@ pentylene glycol (commercially available from Symrise GmbH) may be utilized. In other embodiments, a propylene glycol may be utilized. Where utilized, such humectants may be present in amounts from about 0.1% by weight to about 20% by weight of the dispersion, in embodiments from about 3% by weight to about 10% by weight of the dispersion.

In some embodiments, a preservative such as phenoxyethanol and a humectant such as butylene glycol, hexylene glycol, pentylene glycol and/or propylene glycol may both be added to the formulation. In embodiments, the pentylene glycold and/or propylene glycol may provide humectancy and assist in the preservation of the concentrate when combined with phenoxyethanol. The phenoxyethanol and pentylene glycol and/or propylene glycol mix should be water soluble and non-volatile.

The compound of Formula I may be present in the resulting concentrate in an amount of from about 10% by weight of the concentrate to about 30% by weight of the concentrate, in embodiments from about 18% by weight of the concentrate to about 26% by weight of the concentrate, in some embodiments from about 21% by weight of the concentrate to about 22% by weight of the concentrate. The amount of phospholipids in the concentrate may be from about 1% by weight of the concentrate to about 20% by weight of the concentrate, in embodiments from about 4% by weight of the concentrate to about 12% by weight of the concentrate, with the balance being the solvent, humectant and preservative.

The resulting formulation may be administered directly or, in embodiments, may be combined with any acceptable carrier. As used herein the terms "acceptable carrier" and "acceptable carriers" refers to those compounds which are suitable for use in contact with the tissues of the human or animal without undue toxicity, irritation, allergic response, and the like, commensurate with a reasonable benefit/risk ratio, and effective for their intended use, as well as salts and biocompatible derivatives of those compounds. As used herein, a pharmaceutically acceptable carrier includes any and all solvents, including water, dispersion media, coatings, antibacterial and antifungal agents, stabilizing excipients, absorption enhancing or delaying agents, polymers, including polymeric binders and polymeric adhesives, combinations thereof, and the like. Such materials should be non-toxic to the recipients at the dosages and concentrations employed, and may include buffers such as TRIS-HCl (Tris(hydroxymethyl) Aminomethane Hydrochloride), phosphate, citrate, acetate and other organic acid salts; antioxidants such as ascorbic acid; low molecular weight (less than about ten residues) peptides such as polyarginine, proteins such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN (polyoxyethylene sorbitan monolaurate), PLURONICS (polyoxypropylene-polyoxyethylene block copolymer) and/or polyethylene glycol.

The use of such media and agents is within the purview of those skilled in the art. Supplementary active ingredients can also be incorporated into the compositions.

In embodiments, the above carriers may be utilized alone or in combination to form a carrier system. Suitable carrier systems are within the purview of those skilled in the art and may include, but are not limited to, lotions, creams, gels, emulsions, dispersions, solids, solid sticks, semisolids, aerosol or non-aerosol foams, sprays, serums, transdermal adhesive patch systems, combinations thereof, and the like. In embodiments, the liposomes may be in a liposomal concentrate and may be introduced with a permeation enhancer as described above. In embodiments, the permeation enhancer may be present in a water phase added to the liposomal concentrate to form a composition of the present disclosure. In embodiments, the formulation may be used for transdermal delivery.

The compound of Formula I may thus be present in the final composition, in embodiments a lotion, cream or any other suitable form described above, in amounts of from about 0.2% by weight to about 50%, preferably from about 5% by weight to about 50% by weight of the composition, in embodiments from about 10% by weight to about 50% by weight of the composition.

For example, in some embodiments a lotion or cream may include an oil phase which, in turn, may include emollients, fatty alcohols, emulsifiers, combinations thereof, and the like. For example, an oil phase could include emollients such as C12-15 alkyl benzoates (commercially available as FINSOLV™ TN from Finetex Inc. (Edison, NJ)), capric-caprylic triglycerides (commercially available from Huls as MIGLYOL™ 812), and the like. Other suitable emollients which may be utilized include vegetable derived oils (corn oil, safflower oil, olive oil, macadamian nut oil, etc.); various synthetic esters, including caprates, linoieates, dilinoleates, isostearates, fumarates, sebacates, lactates, citrates, stearates, palmitates, and the like; synthetic medium chain triglycerides, silicone oils or polymers; fatty alcohols such as cetyl alcohol, stearyl alcohol, cetearyl alcohol, lauryl alcohol, combinations thereof, and the like; and emulsifiers including glyceryl stearate, PEG-100 stearate, Glyceryl Stearate, Glyceryl Stearate SE, neutralized or partially neutralized fatty acids, including stearic, palmitic, oleic, and the like; vegetable oil extracts containing fatty acids, Ceteareth-20, Ceteth-20, PEG-150 Stearate, PEG-8 Laurate, PEG-8 Oleate, PEG-8 Stearate, PEG-20 Stearate, PEG-40 Stearate, PEG-150 Distearate, PEG-8 Distearate, combinations thereof, and the like; or other non-polar cosmetic or pharmaceutically acceptable materials used for skin emolliency within the purview of those skilled in the art, combinations thereof, and the like.

The emollients, $C_{12-15}$ alkyl benzoates, may be included for emolliency and spreadability. Where present, the emollient may be present in an amount from about 0.2% by weight to about 15% by weight of the total composition, in embodiments from about 2% by weight to about 6% by weight of the total composition. Alcohols such as cetyl alcohol and stearyl alcohol may be added to impart body or texture to a cream. Where both cetyl alcohol stearyl alcohol are utilized, the ratio of cetyl alcohol to stearyl alcohol may be from about 2:1 to about 1:2, with the waxy alcohols making up from about 1 to about 6 weight percent of the total composition, in embodiments from about 2% by weight to about 4% by weight of the total composition.

As noted above, this oil phase may also include emulsifiers. Suitable emulsifiers include, but are not limited to, stearates including glyceryl stearate, PEG-100 stearate, glyceryl stearate SE, glyceryl stearate citrate, combinations thereof, and the like. In embodiments, a combination of stearates may be utilized in the oil phase as an emulsifier. For example, a glyceryl stearate and PEG-100 stearate mixture (in embodiments, a mixture of glyceryl stearate and polyethylene glycol 100 stearate commercially available as ARLACEL® 165 from ICI Americas) may be used as an emulsifier to form an oil-in-water (o/w) emulsion. In such a combination, the PEG-100 stearate may act as the primary emulsifier and the glyceryl stearate may be a co-emulsifier. The emulsifier may be present in an amount from about 2% by weight to about 8% by weight of the total composition, in embodiments from about 3% by weight to about 5% by weight of the total composition.

The weight ratio of emulsifier to emollients as described above in this oil phase may be from about 10:1 to about 1:2, in some embodiments from about 2:1 to about 1:1.

Where present, an oil phase may be present in an amount of from about 5% to about 20% by weight of a lotion or cream, in embodiments from about 8% to about 15% by weight of a lotion or cream. Lotions or creams formed with the above liposomes may also include a water phase, which may, in embodiments, include the permeation enhancer described above as well as those items combined to form the second phase described above, including humectants and preservatives. Thus, in embodiments, the water phase utilized in formation of a lotion or cream possessing liposomes as described herein may include the second phase described above. In addition, in embodiments it may be desirable to add a viscosity modifier, sometimes referred to herein as a viscosity agent, to provide the lotion and/or cream with a desired viscosity.

Suitable viscosity agents which may be added to the water phase include water soluble polymers, including anionic polymers and nonionic polymers. Useful polymers include vinyl polymers such as cross linked acrylic acid polymers with the CTFA name CARBOMER, pullulan, mannan, scleroglucans, polyvinylpyrrolidone, polyvinyl alcohol, guar gum, hydroxypropyl guar gum, xanthan gum, acacia gum, arabia gum, tragacanth, galactan, carob gum, karaya gum, locust bean gum, carrageenin, pectin, amylopectin, agar, quince seed (*Cydonia oblonga* Mill), starch (rice, corn, potato, wheat), algae colloids (algae extract), microbiological polymers such as dextran, succinoglucan, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble materials such as bentonite, aluminum magnesium silicate, laponite, hectonite, and anhydrous silicic acid. Combinations of the foregoing may also be used in embodiments. In some embodiments, a CARBOMER such as CARBOMER 940 may be added as a viscosity agent to control the rheological properties of the cream formulas and add stability to the primary emulsion.

Where utilized, a viscosity agent may be present in an amount from about 0.1% to about 2% by weight of the composition, in embodiments from about 0.25% to about 0.6% of the composition.

Alternatively, the water phase may contain other soluble humectants such as glycols, polyols, lactate salts, amino acids, peptides, sugars, urea, sodium PCA, hyaluronic acid, or salts thereof, or any other suitable humectant or water soluble or water-dispersible moisturizer within the purview of those skilled in the art. The weight ratio of humectants to permeation enhancer to preservative to viscosity agent may be from about 20:10:1:1 to about 10:20:1:1, in some embodiments from about 15:10:2:1 to about 10:15:1:1.

Thus, as noted above, the water phase utilized to form a lotion and/or cream of the present disclosure may include water, humectants, preservatives, viscosity agents, and permeation enhancers. For example, in embodiments a suitable water phase may include a combination of glycerine, pentylene glycol and/or propylene glycol, ethoxydiglycol, phenoxyethanol, water, and CARBOMER 940 (poly(acrylic acid).

In some embodiments, the viscosity agent may be added to the water phase as a dispersion in a humectant as described above, optionally in combination with water, optionally in combination with a preservative as described above. For example, in embodiments CARBOMER 940 may be added as a dispersion such as a 2% dispersion containing CARBOMER 940 dispersed in a mixture of water, propylene glycol, and phenoxyethanol. This CARBOMER 940 dispersion may be made separately in a batch manufacturing process. Where a viscosity agent such as CARBOMER 940 is added as a separate dispersion to the water phase, the weight ratio of viscosity agent to humectant to preservative to water may be from about 0.3:2:0.05:10 to about 0.5:1:0.2:10, in some embodiments from about 0.1:0.5:0.05:9 to about 0.2:1:0.1:9.

Where present, a water phase may be present in an amount of from about 60% to about 80% by weight of a lotion or cream, in embodiments from about 63% to about 71% by weight of a lotion or cream.

In some embodiments, a third phase, which may be referred to herein as a neutralization phase or buffer phase, may also be added in the formation of a cream or lotion. The components of such a phase may include, but are not limited to, water, amines including triethanolamine, triisopropanolamine, 2-amino-2methyl-1,3-propanediol, tris(hydroxymethyl)amine, 2-aminobutanol, sodium hydroxide, potassium hydroxide, salts such as sodium lactate, potassium lactate, sodium citrate, potassium citrate, sodium or potassium mono-, di, or tri-phosphate, sodium borate, potassium borate, acids such as lactic acid, citric acid, phosphoric acid, boric acid, combinations thereof, and the like. The water may act as a solvent and a diluent for the other ingredients in this phase. The amine such as triethanolamine may act as a neutralizer of an acid component in the water phase, such as the CARBOMER acrylic acid copolymer; additional salts such as a sodium lactate solution (60% w/w in water) and additional acids such as lactic acid may be added as a buffer system to adjust and maintain the final pH of the cream at from about 4.8 to about 6, in some embodiments from about 5 to about 5.5 (within the natural pH range of the skin). In embodiments, a pH of about 5 or higher may be useful, as the CARBOMER 940 acrylic copolymer of the water phase or similar material should be fully neutralized and develop its full viscosity potential.

In embodiments a suitable amount of amine such as triethanolamine may be added so that it is present in an amount from about 0.5% to about 2% by weight of the final composition, in embodiments from about 1% to about 1.5% by weight of the final composition. A suitable amount of salt such as sodium lactate may be added so that it is present in an amount from about 0.5% to about 3% by weight of the final composition, in embodiments from about 1% to about 1.5% by weight of the final composition. In embodiments, a suitable amount of acid such as lactic acid may be added so that it is present in an amount from about 0% to 1% by weight of the final composition, in some embodiments about 0.25% to about 0.75% by weight of the final composition, in some embodiments about 0.5% by weight of the final composition. The neutralizer and/or buffer may be added so that it is present in an amount from about 0.01% to about 10% by weight of the final composition, in embodiments from about 2% to about 4% by weight of the final composition.

Where present, the neutralizing phase may be present in an amount of from about 0.1% to about 15% by weight of a lotion or cream, in embodiments from about 5% to about 8% by weight of a lotion or cream.

In embodiments, other soluble ingredients may also be added which include, but are not limited to, pH adjusting and buffering agents, tonicity adjusting agents, wetting agents and the like, for example, sodium acetate, sodium chloride, potassium chloride, calcium chloride, sorbitan monolaurate, triethanolamine oleate, and the like. Other buffers which may be added include sodium hydroxide, potassium hydroxide, ammonium hydroxide, monoethanolamine, diethanolamine, triethanolamine, diisopropanolamine, aminomethylpropanol, trimethamine, tetrahydroxypropyl ethylenediamine, citric acid, acetic acid, lactic acid, and salts of lactic acid including sodium lactate, potassium lactate, lithium lactate, calcium lactate, magnesium lactate, barium lactate, aluminum lactate, zinc lactate, sodium citrate, sodium acetate, silver lactate, copper lactate, iron lactate, manganese lactate, ammonium lactate, combinations thereof, and the like. These additives may be added to any phase described above utilized in forming a cream or lotion, including the oil phase, water phase, neutralizing phase, pigment, combinations thereof, and the like.

In embodiments the use of the formulations described above may permit tailoring the production of various compositions having the compound of Formula I at varying concentrations. For example, in embodiments, it may have the compound of Formula I at a concentration of from about 10 to about 15 times greater than the amount of compound of Formula I in a final composition for administration. For manufacturing, a large batch of concentrate may be produced, and then multiple portions of the concentrate may be utilized to produce multiple compositions having the bioactive agent at varying concentrations. This permits great flexibility in tailoring the concentration of a compound of Formula I in a composition of the present invention.

The resulting creams, lotions, and the like may have a long shelf-life; i.e., they may remain stable during storage for at least about 2 years, in embodiments from about 2 to about 10 years.

According to a specific embodiment of the present invention, a cleansing composition or shampoo composition is provided, in particular a cleanser or shampoo for animals including humans, comprising the compound of Formula I. The composition can include optionally at least one humectant or moisturizer, at least one surfactant, at least one skin conditioner, at least one hair conditioner, at least one cleansing agent, at least one exfoliant, at least one oil, at least one antioxidant, at least one preservative, at least one emollient (soothing agent), at least one astringent, a fragrance(s), and water.

Some humectants that can be used in a shampoo can also serve as a hair conditioner, and/or a skin conditioner. Some surfactants that can be used can also serve as a hair conditioner, and/or as a foam booster, and/or as a cleansing agent. Some hair conditioners that can be used can also serve as a skin conditioner. Some oils that can be used can also serve as a skin conditioner. Some emollients that can be used can also serve as a skin conditioner. Some antioxidants that can be used can also serve as a skin conditioner. Some astringents that can be used can also serve as a skin conditioner.

Optionally, the composition can also be formulated using a viscosity adjusting agent, e.g., sodium chloride. Optionally, the composition can also be formulated using any commonly used buffer system, if maintaining a certain level of pH is necessary. For example, citric acid can be used to adjust pH.

The total concentration of the moisturizer(s) in the composition can be between about 1 and 10 mass % of the total composition. Some non-limiting examples of moisturizers that can be used include glycerin, honey, and algae extracts. Other non-limiting examples of moisturizers that can be used include urea, sodium lactate, and some amino acids, such as glycine or histidine.

The total concentration of the cleansing agent(s) in the composition can be between about 25 and 40 mass % of the total composition. Some non-limiting examples of cleansing agents that can be used include sodium laurate sulfate, and PEG-80 sorbitan laurate.

The total concentration of the surfactant(s) in the composition can be between about 10 and 20 mass % of the total composition. Some non-limiting examples of surfactants that can be used include sodium $C_{14-16}$ olefin sulfonate, disodium cocamphodiacetate, and PEG-80 sorbitan laurate.

The total concentration of the skin conditioner(s) in the composition can be between about 2 and 15 mass % of the total composition. Some non-limiting examples of skin conditioners that can be used include glycerin, wheat amino acid, *Lavandula angustifolia* (lavender) extract, PEG-120 methyl glucose trioleate, honey, *Mentha pulegium* extract, *Cucumis sativus* (cucumber) fruit extract, *Camellia simensis* leaf extract, *Chamomilla recutita* (*matricaria*) flower extract, *Rosamarinus officinalis* (rosemary) leaf extract, tocopheryl acetate, algae extract, and *Hamamelis virginiana* (witch hazel).

The total concentration of the hair conditioner(s) in the composition can be between about 2 and 10 mass % of the total composition. Some non-limiting examples of hair conditioners that can be used include glycerin, disodium cocamphodiacetate, and wheat amino acid.

The total concentration of the exfoliant(s) in the composition can be between about 0.1 and 1 mass % of the total composition. One non-limiting example of an exfoliant that can be used is bromelain.

The total concentration of the oil(s) in the composition can be between about 0.1 and 2 mass % of the total composition. Some non-limiting examples of an oil that can be used include *Lavandula angustifolia* (lavender) extract and *Cedrus atlantica* (cedarwood) bark oil.

The total concentration of the antioxidant(s) in the composition can be between about 0.1 and 3 mass % of the total composition. Some non-limiting examples of antioxidants that can be used include *Melaleuca altermifolia* (tea tree) leaf oil, *Camellia simensis* leaf extract, and tocopheryl acetate.

The total concentration of the preservative(s) in the composition can be between about 0.1 and 1 mass % of the total composition. Some non-limiting examples of preservatives that can be used include methylisothiazolinone, and methylchloroisothiazolinone.

The total concentration of the emollient(s) in the composition can be between about 0.1 and 2 mass % of the total composition. Some non-limiting examples of emollients that can be used include PEG-120 methyl glucose trioleate, and *Cucumis sativus* (cucumber) fruit extract.

The total concentration of the astrigent(s) in the composition can be between about 0.1 and 1 mass % of the total composition. One non-limiting example of an astrigent that can be used is *Hamamelis virginiana* (witch hazel).

Any composition satisfying the above-described requirements can be prepared using common formulating techniques known to those having ordinary skill in the art. For example, the above-described components can be mixed with one another, followed by adding water, to form an aqueous composition, e.g., by employing rapid stirring. Alternatively, each component, in a separate container, can be preliminary dissolved in water, or otherwise mixed with water resulting in a plurality of water-based systems, each contained in a separate container. The contents of all the containers can then be combined, e.g., by stirring or shaking, to form the final composition.

If desired, those having ordinary skill in the art can design other methods of mixing the components forming the composition. Regardless of the method of mixing that is selected, those having ordinary skill in the art will provide such quantities of each component so that the concentration of each of the components in the composition satisfies the above-described limits.

A method for the treatment of an animal is further provided. A composition can be prepared according to a procedure described above, optionally followed by washing the animal. The composition can be then applied topically onto the skin of an animal that needs protection against ectoparasites. Various methods can be used for applying the composition onto the skin of an animal. For example, the composition can be sprayed using a conventional hand-operated pump. Alternatively, the composition can be formulated to form an aerosol using commonly known methods for aerosol preparation. Those having ordinary skill in the art can devise other methods for applying the composition.

The present invention also provides for a method for protecting objects from infestation, in particular infestation with insects or arachnids, including insects or arachnids that are ectoparasites. The method, in one embodiment, may comprise contacting or covering the surface of the object with a treatment composition comprising the compound of Formula I. Contacting or covering the surface of the object may be achieved, for example, by employing a spraying device comprising the treatment composition of the invention. As such, the invention also provides insect-repellent objects or arachnid-repellent objects, such as for example fabrics or clothes. The fabrics have insect repellent molecules absorbed in the fibers of the fabrics. The fabrics are suitable for use in clothing and, more particularly, are suitable for use in protective garments designed to be worn by individuals, who may be at risk of exposure to insects, in particular ectoparasites. The repellent compounds of the invention may be incorporated into the fabrics in a variety of ways including, but not limited to, immersing the fibers or fabrics in a bath containing the compound of Formula I, providing a spray to the fibers or fabrics or washing the fibers or fabrics. Within the present invention, amounts of the formulation of the invention to the fibers or fabrics may be varied by the skilled person in order to achieve the desired effect of reducing infestation with ectoparasites. It is preferred within the present invention to use amounts sufficient to achieve concentrations of at least 5, 10, 15, 20, 25, 30, 40, 50, 60, 70, 80, 90, or 100 μmol/$m^2$ of the formulation or compounds of the invention on the fibers or fabrics. It is furthermore preferred within the present invention to use amounts of up to 300 μmol/$m^2$ of the formulation or compounds of the invention on the fibers or fabrics. In particular, it is preferably to use an amount sufficient to achieve protection against ectoparasites for 0.1 day to 30 days, particularly for 1 h to 48 h, most particularly from 4 h to 8 h.

In further embodiments, the topical formulation of the present invention comprising a compound of Formula I may be in the form of a lotion, cream, ointment, gel, foam, patch, powder, solid, sponge, tape, vapor, paste or tincture. A further example is the compound of Formula I in the form of a liquid, such as a solution.

The following examples describe the invention further, without limiting it to the content of the examples.

EXAMPLES

Example 1: Mosquito Repellency Assay of Anatabine Derivatives

Results from other compounds of the present invention are shown in Table 1 and compared to DEET, and were similarly tested as follows:

The compound of the invention is mixed with ethanol to make a composition that can be applied to a surface and allowed to dry. After the surface is treated with the compounds of the invention and dried, it is heated to human body temperature, and the number of landings and the total time spent by the mosquitoes on the warm surface by adult *Aedes aegypti* mosquitoes is recorded automatically by machine vision to measure repellency of each compound.

Repellency (based on the number of individual landings on the warm surface) is expressed as a percentage reduction of the control, where the average number of mosquitoes landing on a warm surface treated only with the vehicle solvent is counted. 100% means no mosquitoes landed on the warm surface.

For mosquitoes that still landed on the warm surface, the time spent on the warm surface is also recorded and expressed as a percentage of the control, corresponding to the average time that mosquitoes spent on the same warm surface when treated only with the vehicle solvent. 100% mean that the mosquitoes spent the same time on the treated warm surface as on a warm surface treated only with the vehicle solvent.

Each compound/dose is tested in triplicates using an oil pre-coated glass surface of 132.7 cm and 360 microliters of solution without the compound (the placebo) or with the compound dilution spread on the surface, and allowed to dry before the test. The average and standard error on triplicates is calculated. The control (using only vehicle solvent) is run with ethanol/1% (w/w) dimethylsulfoxide. The same population of mosquitoes is exposed first to the warm surface treated with the vehicle solvent, then to the surface treated with the compound. The concentration of the solution comprising the test compound is adjusted to ensure the treatment dosage of the compound is according to the final concentration per surface unit area in the table.

TABLE 1

| Compound | Concentration [μmol/$m^2$] | Mean repellency (% compared to control) | Standard deviation | Mean probing time on warm-body (% compared to control) | Standard deviation |
|---|---|---|---|---|---|
| exo-3-(3-pyridyl)-2-azabicyclo[2.2.2]oct-5-ene | 75 | 54.1 | 33.69 | 28.87 | 11.44 |
| endo-3-(3-pyridyl)-2-azabicyclo[2.2.2]oct-5-ene | 75 | 62.93 | 11.55 | 67.63 | 28.45 |
| 2-methyl-3-(3-pyridyl)-2-azabicyclo[2.2.2]octane | 23.7 | 56.35 | 15.81 | 60.34 | 2.70 |
| 2-methyl-3-(3-pyridyl)-2-azabicyclo[2.2.2]octane | 75 | 78.00 | 9.63 | 9.75 | 6.66 |
| 3-(1,2,3,6-tetrahydropyridin-2-yl)pyridine | 75 | 81.53 | 8.50 | 29.86 | 16.61 |
| 3-(1,2,5,6-tetrahydropyridin-4-yl)pyridine dihydrochloride | 23.7 | 57.67 | 16.95 | 72.95 | 29.87 |
| 3-(1,2,3,6-tetrahydropyridin-6-yl)pyridine dihydrochloride | 23.7 | 46.46 | 16.70 | 54.70 | 7.64 |
| 2-phenyl-5-(1,2,3,6-tetrahydropyridin-2-yl)pyridine dihydrochloride | 23.7 | 57.79 | 14.72 | 48.79 | 5.49 |
| 2-chloro-5-(1,2,3,6-tetrahydropyridin-2-yl)pyridine dihydrochloride | 23.7 | 33.51 | 21.05 | 69.83 | 8.64 |
| 2,3-dichloro-5-(1,2,3,6-tetrahydropyridin-2-yl)pyridine dihydrochloride | 23.7 | 48.47 | 17.24 | 26.95 | 12.32 |
| 3-ethynyl-5-(1,2,3,6-tetrahydropyridin-2-yl)pyridine dihydrochloride | 23.7 | 38.91 | 19.39 | 63.41 | 9.26 |
| 2-[5-(1,2,3,6-tetrahydropyridin-2-yl)-3-pyridyl]-2,5-diazabicyclo[2.2.1]heptane dihydrochloride | 23.7 | 30.14 | 13.38 | 76.37 | 22.51 |
| 3-[(2S)-4-phenyl-1,2,3,6-tetrahydropyridin-2-yl]pyridine dihydrochloride | 23.7 | 49.39 | 6.36 | 66.30 | 23.15 |

TABLE 1-continued

| Compound | Concentration [μmol/m$^2$] | Mean repellency (% compared to control) | Standard deviation | Mean probing time on warm-body (% compared to control) | Standard deviation |
|---|---|---|---|---|---|
| 3-[(2S)-2-(3-pyridyl)-1,2,3,6-tetrahydropyridin-4-yl]pyridine dihydrochloride | 23.7 | 47.97 | 3.52 | 38.50 | 3.32 |
| 2-methyl-3-(3-pyridinyl)-2-azabicyclo[2.2.2]oct-5-ene | 23.7 | 69.10 | 15.76 | 34.22 | 14.04 |
| 3-(6-chloro-3-pyridyl)-2-methyl-2-azabicyclo[2.2.2]oct-5-ene | 23.7 | 38.68 | 21.11 | 49.89 | 8.13 |
| 3-(6-chloro-3-pyridyl)-2-methyl-2-azabicyclo[2.2.2]octane | 23.7 | 39.07 | 23.61 | 64.60 | 15.48 |
| 2-methyl-3-(6-phenyl-3-pyridyl)-2-azabicyclo[2.2.2]octane hydrochloride | 23.7 | 57.06 | 16.57 | 43.54 | 8.76 |
| 5-(3-pyridyl)-2-azabicyclo[2.2.2]oct-5-ene | 23.7 | 50.40 | 11.05 | 84.14 | 44.59 |
| 2-methyl-5-(3-pyridyl)-2-azabicyclo[2.2.2]oct-5-ene | 23.7 | 82.32 | 3.68 | 44.15 | 13.01 |
| 5-(6-chloro-3-pyridyl)-2-azabicyclo[2.2.2]oct-5-ene hydrochloride | 23.7 | 41.31 | 20.28 | 70.65 | 16.31 |
| 5-(6-chloro-3-pyridyl)-2-methyl-2-azabicyclo[2.2.2]oct-5-ene | 23.7 | 68.25 | 15.93 | 46.57 | 9.04 |
| 7-(3-pyridyl)-2-azabicyclo[2.2.2]oct-5-ene | 23.7 | 60.39 | 13.79 | 51.47 | 20.46 |
| 7-(6-chloro-3-pyridyl)-2-azabicyclo[2.2.2]oct-5-ene | 23.7 | 57.82 | 15.85 | 59.26 | 27.60 |
| 3-(2-piperidylmethoxy)pyridine | 23.7 | 54.17 | 15.40 | 59.79 | 11.59 |
| 3-[[(2S)-1,2,3,6-tetrahydropyridin-2-yl]methoxy]pyridine | 23.7 | 65.00 | 11.75 | 66.81 | 4.19 |
| 2-ethynyl-5-[2-(3-pyridyl)-1,2,3,6-tetrahydropyridin-4-yl]pyridine | 23.7 | 48.17 | 16.69 | 57.72 | 18.59 |
| 2-methyl-7-(3-pyridyl)-2-azabicyclo[2.2.2]oct-5-ene | 23.7 | 51.61 | 2.82 | 47.77 | 6.86 |
| 7-(6-chloro-3-pyridyl)-2-methyl-2-azabicyclo[2.2.2]oct-5-ene | 23.7 | 59.30 | 8.83 | 53.84 | 12.74 |
| 7-(6-ethoxypyridin-3-yl)-2-methyl-2-azabicyclo[2.2.2]oct-5-ene | 23.7 | 77.45 | 2.31 | 39.97 | 5.95 |
| N,N-diethyl-3-methyl-benzamide, DEET | 23.7 | 75.21 | 5.59 | 19.80 | 10.61 |

Example 2: Tick Repellency Assay and Acaricidal Activity of Anatabine Derivatives The test for repellency of compounds to ticks relies on their questing behavior. Ticks will explore their habitat to find a suitable host hunting site and try to avoid areas treated with repellent or irritating substances. The compounds of the invention are dissolved in dimethylsulfoxide (DMSO) and then diluted with ethanol to make a composition containing a maximum of 1% (w/w) DMSO, which is suitable for achieving the stated concentration per unit area on the applied surface. The composition or control is applied to the treatment area and allowed to dry. A circular arena of 8.96 cm2 from which ticks cannot escape is used for the assay. Only one quadrant (2.25 cm2) is treated with the test compound or control, while the rest is left untreated. 30 to 60 *Rhipicephalus sanguineus* tick larvae are deposited in the non-treated area of the circular arena. After 1 minute, the change in position of the ticks in the treated and untreated areas is measured for a duration of 2 minutes. A visual recording device, such as a camera, records the test area, from which number of movements in the treated and untreated areas can be counted and reported as number of tick movements. If the compound shows repellent activity, ticks will avoid walking on the treated quadrant. Repellency is expressed as: $1-M_T/M_U)\times100$, where $M_T$ is the number of tick movements within the treated area, and $M_U$ is the number of tick movements within the untreated area. 100% means that all the ticks completely avoided the treated surface. The potential acaricidal activity of the test compounds is measured in the same setup over a duration of 8 minutes and the knockdown activity is expressed in % motility reduction between the beginning and the end of the 8 minutes.

TABLE 2

| Compound | Concentration [μmol/m$^2$] | Mean repellency (%) | Standard deviation | Knockdown activity (%) | Standard deviation |
|---|---|---|---|---|---|
| exo-3-(3-pyridyl)-2- | 89 | 73.50 | 23.64 | 41.93 | 12.40 |
| azabicyclo[2.2.2]oct-5-ene | 28.1 | 52.33 | 15.47 | 18.67 | 4.61 |
| endo-3-(3-pyridyl)-2- | 89 | 63.43 | 8.06 | 73.07 | 6.65 |

TABLE 2-continued

| Compound | Concentration [μmol/m$^2$] | Mean repellency (%) | Standard deviation | Knockdown activity (%) | Standard deviation |
|---|---|---|---|---|---|
| azabicyclo[2.2.2]oct-5-ene | 28.1 | 24.43 | 12.29 | 15.67 | 8.70 |
| 2-methyl-3-(3-pyridyl)-2-azabicyclo[2.2.2]octane | 89 | 96.23 | 4.47 | 6.70 | 11.60 |
| | 28.1 | 78.80 | 5.38 | 0.00 | 0.00 |
| 3-(1,2,3,6-tetrahydropyridin-2-yl)pyridine | 89 | 66.63 | 10.51 | 45.23 | 2.67 |
| | 28.1 | 15.10 | 13.16 | 10.47 | 4.54 |
| 3-(1,2,5,6-tetrahydropyridin-4-yl)pyridine dihydrochloride | 89 | 95.43 | 1.08 | 5.43 | 9.41 |
| | 28.1 | 80.17 | 5.60 | 16.20 | 8.85 |
| 3-(1,2,3,6-tetrahydropyridin-6-yl)pyridine dihydrochloride | 89 | 50.40 | 28.46 | 0.00 | 0.00 |
| | 28.1 | 37.33 | 38.18 | 0.00 | 0.00 |
| 2-phenyl-5-(1,2,3,6-tetrahydropyridin-2-yl)pyridine dihydrochloride | 89 | 77.50 | 21.23 | 0.00 | 0.00 |
| | 28.1 | 82.93 | 6.40 | 0.00 | 0.00 |
| 2-chloro-5-(1,2,3,6-tetrahydropyridin-2-yl)pyridine dihydrochloride | 89 | 100.00 | 0.00 | 0.00 | 0.00 |
| | 28.1 | 98.87 | 1.79 | 0.00 | 0.00 |
| 2,3-dichloro-5-(1,2,3,6-tetrahydropyridin-2-yl)pyridine dihydrochloride | 89 | 100.00 | 0.00 | 2.50 | 3.50 |
| | 28.1 | 100.00 | 0.00 | 0.00 | 0.00 |
| 3-ethynyl-5-(1,2,3,6-tetrahydropyridin-2-yl)pyridine dihydrochloride | 89 | 93.93 | 8.99 | 0.00 | 0.00 |
| | 28.1 | 92.63 | 12.76 | 0.00 | 0.00 |
| 2-[5-(1,2,3,6-tetrahydropyridin-2-yl)-3-pyridyl]-2,5-diazabicyclo[2.2.1]heptane dihydrochloride | 89 | 74.00 | 15.34 | 0.00 | 0.00 |
| | 28.1 | 66.33 | 18.64 | 0.00 | 0.00 |
| 3-[(2S)-4-phenyl-1,2,3,6-tetrahydropyridin-2-yl]pyridine dihydrochloride | 89 | 80.63 | 17.76 | 0.00 | 0.00 |
| | 28.1 | 88.20 | 6.18 | 0.00 | 0.00 |
| 3-[(2S)-2-(3-pyridyl)-1,2,3,6-tetrahydropyridin-4-yl]pyridine dihydrochloride | 89 | 51.73 | 30.96 | 0.00 | 0.00 |
| | 28.1 | 81.37 | 3.19 | 1.63 | 2.83 |
| 2-methyl-3-(3-pyridinyl)-2-azabicyclo[2.2.2]oct-5-ene | 89 | 96.47 | 3.50 | 0.00 | 0.00 |
| | 28.1 | 91.37 | 7.23 | 0.00 | 0.00 |
| 3-(6-chloro-3-pyridyl)-2-methyl-2-azabicyclo[2.2.2]oct-5-ene | 89 | 54.27 | 48.71 | 0.00 | 0.00 |
| | 28.1 | 29.67 | 29.61 | 0.00 | 0.00 |
| 3-(6-chloro-3-pyridyl)-2-methyl-2-azabicyclo[2.2.2]octane | 89 | 67.00 | 12.57 | 0.00 | 0.00 |
| | 28.1 | 41.97 | 34.07 | 0.00 | 0.00 |
| 2-methyl-3-(6-phenyl-3-pyridyl)-2-azabicyclo[2.2.2]octane hydrochloride | 89 | 26.77 | 29.95 | 7.20 | 12.47 |
| | 28.1 | 42.23 | 27.11 | 0.00 | 0.00 |
| 5-(3-pyridyl)-2-azabicyclo[2.2.2]oct-5-ene | 89 | 58.40 | 6.05 | 2.83 | 4.40 |
| | 28.1 | 60.47 | 34.48 | 0.00 | 0.00 |
| 2-methyl-5-(3-pyridyl)-2-azabicyclo[2.2.2]oct-5-ene | 89 | 39.83 | 34.63 | 3.53 | 4.36 |
| | 28.1 | 46.23 | 44.82 | 0.00 | 0.00 |
| 5-(6-chloro-3-pyridyl)-2-azabicyclo[2.2.2]oct-5-ene hydrochloride | 89 | 39.67 | 34.42 | 6.40 | 9.09 |
| | 28.1 | 44.37 | 19.62 | 0.00 | 0.00 |
| 5-(6-chloro-3-pyridyl)-2-methyl-2-azabicyclo[2.2.2]oct-5-ene | 89 | 27.53 | 26.31 | 2.40 | 2.95 |
| | 28.1 | 25.03 | 9.59 | 0.00 | 0.00 |
| 7-(3-pyridyl)-2-azabicyclo[2.2.2]oct-5-ene | 89 | 59.07 | 20.06 | 9.27 | 8.20 |
| | 28.1 | 15.50 | 13.03 | 1.57 | 2.71 |
| 7-(6-chloro-3-pyridyl)-2-azabicyclo[2.2.2]oct-5-ene | 89 | 21.20 | 28.50 | 4.93 | 4.31 |
| | 28.1 | 33.53 | 29.04 | 0.00 | 0.00 |
| 3-(2-piperidylmethoxy)pyridine | 89 | 91.00 | 10.75 | 14.37 | 5.18 |
| | 28.1 | 75.50 | 4.20 | 0.00 | 0.00 |
| 3-[[(2S)-1,2,3,6-tetrahydropyridin-2-yl]methoxy]pyridine | 89 | 78.47 | 5.51 | 6.27 | 10.85 |
| | 28.1 | 68.53 | 3.93 | 3.37 | 3.62 |
| 2-ethynyl-5-[2-(3-pyridyl)-1,2,3,6-tetrahydropyridin-4-yl]pyridine | 89 | 79.03 | 9.15 | 1.20 | 2.08 |
| | 28.1 | 75.80 | 6.54 | 3.33 | 5.77 |
| 2-methyl-7-(3-pyridyl)-2-azabicyclo[2.2.2]oct-5-ene | 89 | 81.20 | 3.18 | 4.63 | 8.03 |
| | 28.1 | 51.60 | 3.61 | 6.77 | 6.65 |
| 7-(6-chloro-3-pyridyl)-2-methyl-2-azabicyclo[2.2.2]oct-5-ene | 89 | 97.83 | 3.75 | 3.57 | 6.18 |
| | 28.1 | 86.30 | 8.82 | 7.40 | 7.03 |
| 7-(6-ethoxypyridin-3-yl)-2- | 89 | 74.50 | 22.27 | 15.73 | 7.66 |

TABLE 2-continued

| Compound | Concentration [μmol/m²] | Mean repellency (%) | Standard deviation | Knockdown activity (%) | Standard deviation |
|---|---|---|---|---|---|
| methyl-2-azabicyclo[2.2.2]oct-5-ene | 28.1 | 78.03 | 16.77 | 17.90 | 6.15 |
| N,N-diethyl-3-methyl- | 89 | 100.00 | 0.00 | 0.00 | 0.00 |
| benzamide,DEET | 28.1 | 91.83 | 3.79 | 0.00 | 0.00 |
| Ethyl alcohol/1% dimethylsulfoxide (control) | 100 | 33.17 | 28.34 | 0.00 | 0.00 |

The following table provides an overview of the compounds whose synthesis will be described hereinbelow:

| No. | structure | chemical name |
|---|---|---|
| 1 | 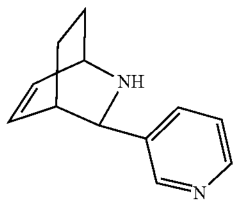 [SMILES: C1=CC23CCC2NC(c2cccnc2)C13] | exo-3-(pyridin-3-yl)-2-azabicyclo[2.2.2]oct-5-ene |
| 2 | 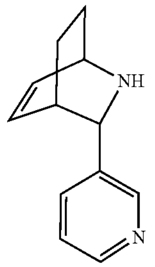 [SMILES: C1=CC23CCC2NC(c2cccnc2)C13] | endo-3-(pyridin-3-yl)-2-azabicyclo[2.2.2]oct-5-ene |
| 3 | 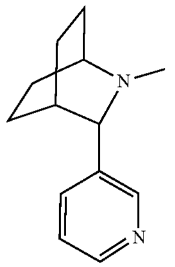 [SMILES: CN1C(c2cccnc2)C2CCC23CCC13] | 2-methyl-3-(pyridin-3-yl)-2-azabicyclo[2.2.2]octane |
| 4 | 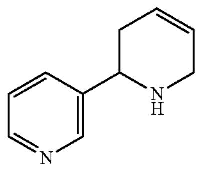 [SMILES: C1=CCC(c2cccnc2)NC1] | 3-(1,2,3,6-tetrahydropyridin-2-yl)pyridine |
| 5 | 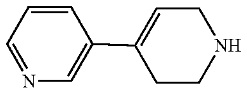 [SMILES: C1=C(c2cccnc2)CCNC1] | 3-(1,2,5,6-tetrahydropyridin-4-yl)pyridine dihydrochloride |
| 6 | 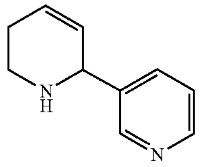 [SMILES: C1=CC(c2cccnc2)NCC1] | 3-(1,2,3,6-tetrahydropyridin-6-yl)pyridine dihydrochloride |

-continued

| No. | structure | chemical name |
| --- | --- | --- |
| 7 | 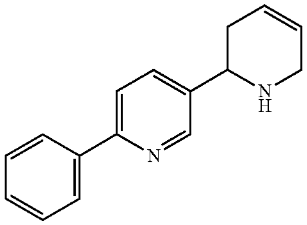 [SMILES: C1=CCC(c2ccc(-c3ccccc3)nc2)NC1] | 2-phenyl-5-(1,2,3,6-tetrahydropyridin-2-yl)pyridine dihydrochloride |
| 8 | 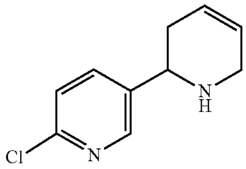 [SMILES: Clc1ccc(C2CC=CCN2)cn1] | 2-chloro-5-(1,2,3,6-tetrahydropyridin-2-yl)pyridine dihydrochloride |
| 9 | 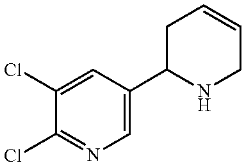 [SMILES: Clc1cc(C2CC=CCN2)cnc1Cl] | 2,3-dichloro-5-(1,2,3,6-tetrahydropyridin-2-yl)pyridine dihydrochloride |
| 10 | 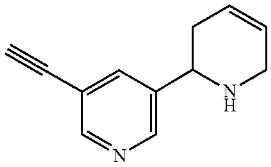 | 3-ethynyl-5-(1,2,3,6-tetrahydropyridin-2-yl)pyridine dihydrochloride |
| 11 | 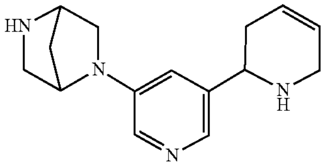 [SMILES: C1=CCC(c2cncc(N3CC4CC3CN4)c2)NC1] | 2-[5-(1,2,3,6-tetrahydropyridin-2-yl)-3-pyridyl]-2,5-diazabicyclo[2.2.1]heptane dihydrochloride |
| 12 | 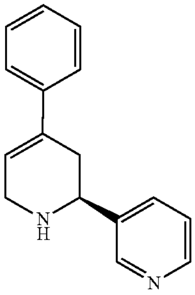 [SMILES: C1=C(c2ccccc2)C[C@@H](c2cccnc2)NC1] | 3-[(2S)-4-phenyl-1,2,3,6-tetrahydropyridin-2-yl]pyridine dihydrochloride |
| 13 | 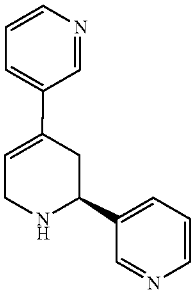 [SMILES: C1=C(c2cccnc2)C[C@@H](c2cccnc2)NC1] | 3-[(2S)-2-(3-pyridyl)-1,2,3,6-tetrahydropyridin-4-yl]pyridine dihydrochloride |

-continued

| No. | structure | chemical name |
|---|---|---|
| 14 | 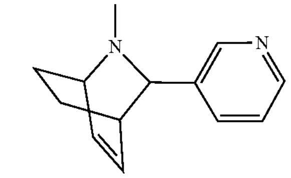 [SMILES: CN1C(c2cccnc2)C2C=CC23CCC13] | 2-methyl-3-(3-pyridinyl)-2-azabicyclo[2.2.2]oct-5-ene |
| 15 | 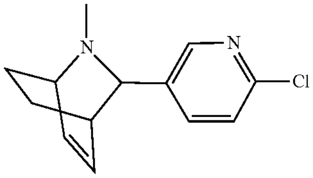 [SMILES: CN1C(c2ccc(Cl)nc2)C2C=CC23CCC13] | 3-(6-chloro-3-pyridyl)-2-methyl-2-azabicyclo[2.2.2]oct-5-ene |
| 16 | 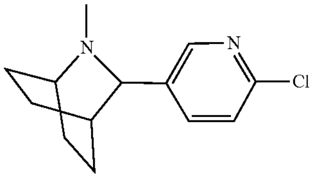 [SMILES: CN1C(c2ccc(Cl)nc2)C2CCC23CCC13] | 3-(6-chloro-3-pyridyl)-2-methyl-2-azabicyclo[2.2.2]octane |
| 17 | 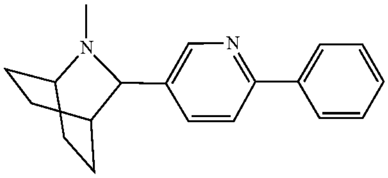 [SMILES: CN1C(c2ccc(-c3ccccc3)nc2)C2CCC23CCC13] | 2-methyl-3-(6-phenyl-3-pyridyl)-2-azabicyclo[2.2.2]octane hydrochloride |
| 18 | 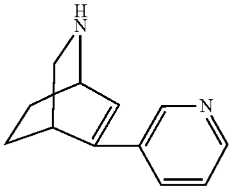 [SMILES: C1=C(c2cccnc2)C2CCC23CNC13] | 5-(3-pyridyl)-2-azabicyclo[2.2.2]oct-5-ene |
| 19 | 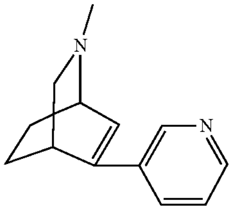 [SMILES: CN1CC23CCC2C(c2cccnc2)=CC13] | 2-methyl-5-(3-pyridyl)-2-azabicyclo[2.2.2]oct-5-ene |
| 20 | 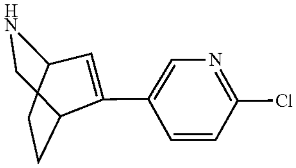 [SMILES: Clc1ccc(C2=CC3NCC34CCC24)cn1] | 5-(6-chloro-3-pyridyl)-2-azabicyclo[2.2.2]oct-5-ene-hydrochloride |
| 21 | 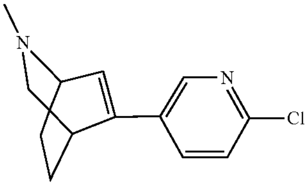 [SMILES: CN1CC23CCC2C(c2ccc(Cl)nc2)=CC13] | 5-(6-chloro-3-pyridyl)-2-methyl-2-azabicyclo[2.2.2]oct-5-ene |

-continued
| No. | structure | chemical name |
| --- | --- | --- |
| 22 | 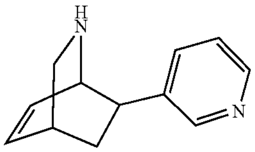 [SMILES: C1=CC23CNC2C(c2cccnc2)CC13] | 7-(3-pyridyl)-2-azabicyclo[2.2.2]oct-5-ene |
| 23 | 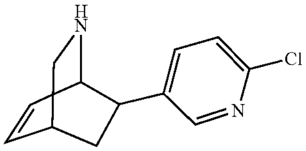 [SMILES: Clc1ccc(C2CC3C=CC34CNC24)cn1] | 7-(6-chloro-3-pyridyl)-2-azabicyclo[2.2.2]oct-5-ene |
| 24 | 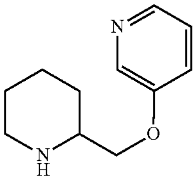 [SMILES: c1cncc(OCC2CCCCN2)c1] | 3-(2-piperidylmethoxy)pyridine |
| 25 | 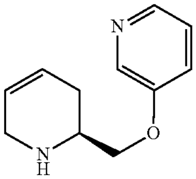 [SMILES: C1=CC[C@@H](COc2cccnc2)NC1] | 3-[[(2S)-1,2,3,6-tetrahydroypridin-2-yl]methoxy]pyridine |
| 26 | 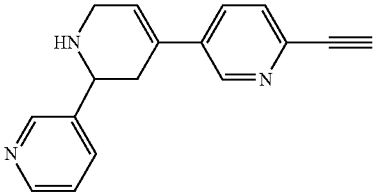 [SMILES: C#Cc1ccc(C2=CCNC(c3cccnc3)C2)cn1] | 2-ethynyl-5-[2-(3-pyridyl)-1,2,3,6-tetrahydropyridin-4-yl]pyridine |
| 27 | 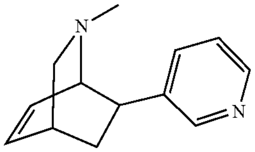 [SMILES: CN1CC23C=CC2CC(c2cccnc2)C13] | 2-methyl-7-(3-pyridyl)-2-azabicyclo[2.2.2]oct-5-ene |
| 28 | 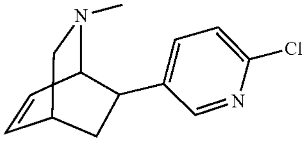 [SMILES: CN1CC23C=CC2CC(c2ccc(Cl)nc2)C13] | 7-(6-chloro-3-pyridyl)-2-methyl-2-azabicyclo[2.2.2]oct-5-ene |
| 29 | 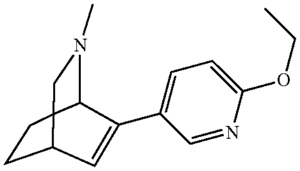 [SMILES: CCOc1ccc(C2=CC3CCC34CN(C)C24)cn1] | 7-(6-ethoxypyridin-3-yl)-2-methyl-2-azabicyclo[2.2.2]oct-5-ene |

Compounds 1-3 were synthesized by SpiroChem, compound 5 was purchased from Enamine, compounds 4, 7-29 were obtained by WuXi Apptec Co., Ltd., N,N-diethyl-3-methyl-benzamide was purchased from Sigma-Aldrich.

Compound 1 and 2

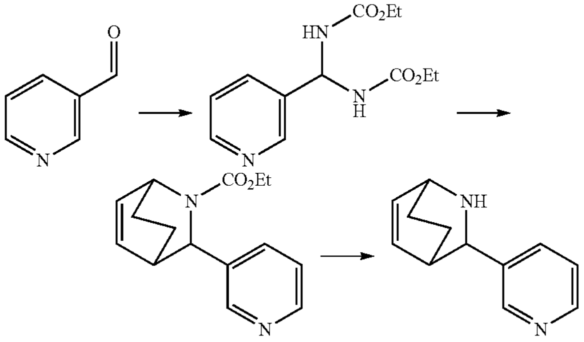

Diethyl(pyridin-3-ylmethylene)dicarbamate. p-Toluenesulfonic acid (5.00 g, 26.3 mmol) was added to a solution of ethyl carbamate (33.27 g, 373.4 mmol) and nicotinaldehyde (17.53 mL, 186.7 mmol) in benzene (400 mL). The solution was stirred at strong reflux with a Dean Stark apparatus (overnight). A precipitate formed during the reaction. The reaction mixture was cooled to 0° C. and the material was filtrated. It was further washed twice with diethyl ether to afford a colorless solid (6.2 g, 88%).

Ethyl 3-(pyridin-3-yl)-2-azabicyclo[2.2.2]oct-5-ene-2-carboxylate. Cyclohexa-1,3-diene (1.57 mL, 16.46 mmol) was added to a solution of diethyl(pyridin-3-ylmethylene) dicarbamate (4.00 g, 14.97 mmol) in acetic acid (30 mL). Boron trifluoride acetic acid complex (17.04 mL, 122.7 mmol) was added and the tube was sealed and heated at 80° C. for 3 h. The mixture was then poured at 0° C. into a sodium hydroxide solution (6M) to reach pH=14. The aqueous layer was then extracted with dichloromethane (3 times). The organic layers were dried over sodium sulfate, filtered and evaporated. The residue was purified by flash chromatography using a 50 to 100% ethyl acetate/cyclohexane gradient to afford an orange to brown oil as a mixture exo/endo-isomers (0.650 g, 17%). $^1$H NMR (400 MHz, chloroform-d) δ 8.47-8.55 (m, 2H), 7.52-7.60 (m, 1H), 7.20-7.26 (m, 1H), 6.38-6.40 (in, 0.45H), 6.24-6.30 (in, 0.55H), 4.76 (s, 0.55H), 4.68 (s, 0.45H), 4.44 (t, J=5.2 Hz, 0.45H), 4.34 (t, J=5.2 Hz, 0.55H), 3.91-4.12 (m, 2H), 2.50-2.60 (m, 1H) 2.40-2.45 (m, 2H), 2.08-2.20 (m, 1H), 1.70-1.76 (m, 1H), 1.27 (t, J=7.1 Hz, 2H), 0.95 (t, J=7.1 Hz, 1H).

3-(Pyridin-3-yl)-2-azabicyclo[2.2.2]oct-5-ene. KOH (3.30 g, 59.00 mmol) was added to ethyl 3-(pyridin-3-yl)-2-azabicyclo[2.2.2]oct-5-ene-2-carboxylate in diglyme (10 mL). The tube was sealed and the solution was heated under microwave 30 min at 160° C. The volatiles were evaporated. Water and dichloromethane were added to the residue and the pH was adjusted to 8-9 with 2M hydrochloric acid. The layers were separated and the aqueous layer was washed with dichloromethane. The organic layers were combined and concentrated under vacuum. The residue was purified by chromatography column using dichloromethane—methanol gradient 1:0 to 4:1 as eluent.

Compound 1: $^1$H NMR (400 MHz, chloroform-d) δ 8.53 (d, J=1.8 Hz, 1H), 8.40 (d, J=5.0 Hz, 1H), 7.70 (dt, J=8.05, 1.80, 1H), 7.16-7.20, (m, 1H), 5.95-5.99 (m, 1H), 5.55-5.59 (m, 1H), 4.15 (s, 1H), 3.68 (t, J=5.0 Hz, 1H), 2.95-3.05 (br s, 2H), 2.47-2.18 (m, 3H), 1.99-2.02 (m, 1H), 1.73 (d, J=8.0 Hz, 1H).

Compound 2: $^1$H NMR (400 MHz, chloroform-d) δ 8.64 (d, J=1.8 Hz, 1H), 8.45 (d, J=5.0 Hz, 1H), 7.75 (dt, J=8.05, 1.80, 1H), 7.16-7.20, (m, 1H), 6.22-6.18 (m, 1H), 5.58-5.62 (m, 1H), 4.56 (s, 1H), 3.78 (t, J=5.0 Hz, 1H), 2.23-2.53 (m, 2H), 1.84-2.10 (m, 4H), 1.60 (d, J=8.0 Hz, 1H)

Compound 3

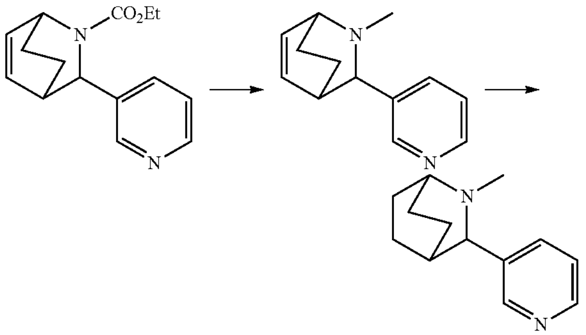

2-Methyl-3-(pyridin-3-yl)-2-azabicyclo[2.2.2]oct-5-ene. An ether solution of ethyl 3-(pyridin-3-yl)-2-azabicyclo [2.2.2]oct-5-ene-2-carboxylate was added to an ether solution of lithium aluminum hydride. The solution was stirred at reflux (6 h). Water was added and the organic layer was extracted with dichloromethane (3×). The organic layers were combined, dried over $Na_2SO_4$ and under vacuum. The residue was purified by flash chromatography using a 0 to 10% dichloromethane—methanol gradient to afford brown oil as a mixture of exo/endo isomers (0.150 g, 48%). $^1$H NMR (400 MHz, chloroform-d) δ 8.59 (d, J=1.8 Hz, 1H), 8.40 (d, J=5.0 Hz, 1H), 7.67 (dt, J=8.05, 1.80, 1H), 7.17, (dd, J=7.8, 4.6 Hz, 1H), 5.84-5.91 (m, 1H), 5.68-5.74 (m, 1H), 3.35 (t, J=4.8 Hz, 1H), 3.07 (s, 1H), 2.29-2.39 (m, 1H), 2.25 (s, 3H), 2.17-2.23 (m, 1H), 2.06-2.16 (m, 2H), 1.65 (m, 1H).

2-Methyl-3-(pyridin-3-yl)-2-azabicyclo[2.2.2]octane. Palladium on carbon (Pd/C) (10 wt. % loading, 8 mg) was added to an ethyl acetate solution of 2-methyl-3-(pyridin-3-yl)-2 azabicyclo[2.2.2]oct-5-ene (80 mg, 0.04 mmol). The solution was stirred 5 h under hydrogen atmosphere (1 atm). Pd/C was filtered and the pad of Celite was washed with ethyl acetate. Pd/C (8 mg) was added to the solution, and the mixture was stirred 16 h under hydrogen atmosphere (1 atm). Pd/C was filtered and the pad of Celite was washed with ethyl acetate. The volatiles were evaporated leading to 2-methyl-3-(pyridin-3-yl)-2-azabicyclo[2.2.2]octane (78 mg, quant.).

$^1$H NMR (400 MHz, chloroform-d) δ 8.32-8.37 (m, 2H), 7.37-7.42 (m, 1H), 7.12-7.22 (m, 1H), 2.40-2.55 (m, 1H), 2.31 (s, 3H), 2.17-2.28 (m, 1H), 1.80-1.45 (m, 7H), 1.10-1.20 (m, 1H) 0.75-0.95 (m, 2H).

Compound 4

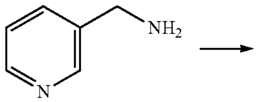

-continued

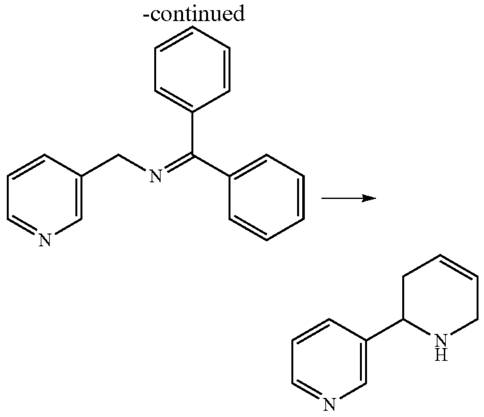

1,1-Diphenyl-N-(3-pyridylmethyl)methanimine. To a solution of 3-(aminomethyl)pyridine (500 g, 2.74 mol) in toluene (2000 mL) was added p-toluenesulfonic acid (47.2 g, 274 mmol) and benzophenone (374 g, 3.46 mol, 350 mL). The mixture was stirred at 110° C. for 12 hr. TLC (petroleum ether:ethyl acetate=3:1) showed 3-(aminomethyl)pyridine (Rf=0.8) was consumed, and a new major spot (Rf=0.5) formed. The reaction mixture was concentrated under reduced pressure to remove toluene. The residue was diluted with ethyl acetate (500 mL) and filtered and concentrated under reduced pressure to give a residue. The residue was purified by flash silica gel chromatography (ISCO®; 1.5 kg SepaFlash® Silica Flash column, eluent of 0~30% ethyl acetate/petroleum ether gradient, flow rate 200 mL/min). 1,1-Diphenyl-N-(3-pyridylmethyl)methanimine (500 g, 1.80 mol, 65.6% yield, 98.1% purity) was obtained as a yellow oil; TLC (petroleum ether:ethyl acetate, 3:1, product Rf=0.5; m/z=273.3 $(M+1)^+$; $^1$H NMR (400 MHz, $CDCl_3$) δ 8.48-8.47 (m, 1H), 8.43-8.42 (m, 1H), 7.65-7.60 (m, 3H), 7.43-7.41 (m, 1H), 7.33-7.29 (m, 2H), 7.27-7.14 (m, 1H), 7.14-7.12 (m, 2H), 4.53 (s, 2H).

3-(1,2,3,6-Tetrahydropyridin-2-yl)pyridine. To a mixture of 1,1-diphenyl-N-(3-pyridylmethyl)methanimine (500 g, 1.84 mol) in tetrahydrofuran (1.00 L) was added lithium diisopropylamide (2 M, 1.00 L) at −78° C. After addition, the mixture was stirred at −60° C. for 30 min. Then to the mixture was added cis-1,4-dichloro-2-butene (364 g, 2.91 mol, 305 mL) at −60° C. After addition, the mixture was stirred at −60° C. for 1 hr. The mixture was quenched with 2 N HCl (300 mL) and stirred at 25° C. for 30 min. Then the mixture was extracted with methyl tert-butyl ether (500 mL×3). Then the aqueous water phase was basified with solid $K_2CO_3$ to pH=12. The water phase was stirred at 25° C. for 2 hr. Then the water phase was extracted with dichloromethane (1 L×5). The combined dichloromethane phases were washed with brine (2 L) and concentrated under reduced pressures to afford an oil residue. TLC (ethyl acetate—methanol=10:1) showed a main new spot was found (Rf=0.2). The oil was purified with chromatography column (silica gel, petroleum ether—ethyl acetate, 1:0 and ethyl acetate—methanol, 10:1, Rf=0.2). Obtained crude material was purified with reverse chromatography ($NH_4ON$, $CH_3CN$) to give 3-(1,2,3,6-tetrahydropyridin-2-yl)pyridine (52.0 g, 318 mmol, 17.3% yield, 98.1% purity); m/z $(M+H)^+$=161; $^1$H NMR (400 MHz, $CDCl_3$) δ 8.55 (d, J=2.0 Hz, 1H), 8.44 (dd, J=1.6, 4.8 Hz, 1H), 7.66 (td, J=1.6, 7.6 Hz, 1H), 7.30-7.11 (m, 1H), 5.89-5.60 (m, 2H), 3.83 (t, J=7.2 Hz, 1H), 3.64-3.33 (m, 2H), 2.28-2.14 (m, 2H).

Compound 6

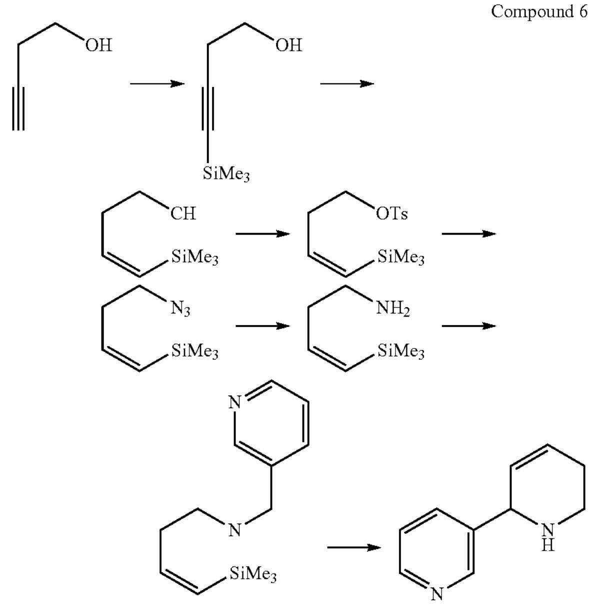

Trimethylsilylbut-3-yn-1-ol. To a solution of but-3-yn-1-ol (10.0 g, 142 mmol, 10.8 mL, 1.00 eq.) in tetrahydrofuran (100 mL) was added tert-butyl lithium (2.5 M, 85.5 mL, 1.50 eq.) at −60° C., the mixture was stirred for 1 hr. Then trimethylsilyl chloride (20.1 g, 185 mmol, 23.4 mL, 1.30 eq.) was added at −60° C. The mixture was stirred at 0° C. for 2 hrs. The reaction mixture was quenched by addition of saturated aqueous solution of $NH_4Cl$ (10 mL) at 0° C., and then diluted with water (50 mL) and extracted with ethyl acetate (100 mL×2). The combined organic layers were washed with brine (100 mL×2), dried over $Na_2SO_4$, filtered and concentrated under reduced pressure to give a residue. The residue was purified by flash silica gel chromatography (ISCO®; 120 g SepaFlash® Silica Flash Column, Eluent of 0~30% ethyl acetate/petroleum ether gradient, flow rate 60 mL/min) to give 4-trimethylsilylbut-3-yn-1-ol (9.40 g, 66.0 mmol, 46.3% yield) as colorless oil; $^1$HNMR (400 MHz, $CDCl_3$) δ 3.71 (m, 2H), 2.51 (m, 2H), 0.16 (s, 9H).

4-Trimethylsilylbut-3-en-1-ol. To a solution of 4-trimethylsilylbut-3-yn-1-ol in methyl tert-butyl ether (100 mL) was added diisobutylaluminium hydride (1 M, 189 mL, 3.00 eq.) at 0° C. The mixture was stirred at 0° C. for 30 min. The reaction was heated at 60° C. 12 hrs. The reaction mixture was quenched by addition of $H_2SO_4$ (2M, 100 ml) at 0° C., then the mixture was filtered through Celite and diluted with water (100 mL) and extracted with ethyl acetate (100 mL×2). The combined organic layers were washed with brine (100 mL×2), dried over $Na_2SO_4$, filtered and concentrated under reduced pressure to give 4-trimethylsilylbut-3-en-1-ol (7.00 g, crude) as yellow oil. $^1$HNMR (400 MHz, $CDCl_3$) δ 6.33-6.26 (m, 1H), 5.71-5.68 (d, J=12 Hz, 1H), 3.70-3.67 (m, 2H), 2.43-2.41 (m, 2H), 0.14 (s, 9H).

4-Trimethylsilylbut-3-enyl 4-methylbenzenesulfonate. To a solution of 4-trimethylsilylbut-3-en-1-ol (7.00 g, 48.5 mmol, 1.00 eq.) in dichloromethane (80 mL) was added 4-dimethylaminopyridine (3.50 g, 28.6 mmol, 0.591 eq.) and 4-methylbenzenesulfonyl chloride (11.1 g, 58.2 mmol, 1.20 eq.), triethylamine (4.90 g, 48.4 mmol, 6.74 mL, 0.998 eq.) The mixture was stirred at 0° C. for 2 hrs. The residue was diluted with water (40 mL) and extracted with dichloromethane (20 mL×2). The combined organic layers were washed with brine (40 mL×2), dried over $Na_2SO_4$, filtered and concentrated under reduced pressure to give a residue. The residue was purified by column chromatography ($SiO_2$, petroleum ether/ethyl acetate=80/1) to give 4-trimethylsilyl-but-3-enyl 4-methylbenzenesulfonate (11.3 g, 37.8 mmol, 78.0% yield) as colorless oil. $^1$HNMR (400 MHz, DMSO-$d_6$) δ 7.78-7.76 (d, J=8.2 Hz, 2H), 7.49-7.47 (m, 2H), 6.14-6.07 (m, 1H), 5.59-5.55 (d, J=14.0 Hz, 1H), 4.06-4.02 (m, 2H), 2.50-2.42 (s, 2H), 0.05 (s, 9H).

1-Azido-4-trimethylsilylbut-3-ene. To a solution of 4-trimethylsilylbut-3-enyl 4-methylbenzenesulfonate (11.3 g, 37.8 mmol, 1.00 eq.) in N,N-dimethylformamide (120 mL) was added $NaN_3$ (5.66 g, 87.0 mmol, 2.50 eq.) at 25° C. The mixture was stirred at 60° C. for 2 hr. The reaction mixture was diluted with water (60 mL) and extracted with ethyl acetate (100 mL×2). The combined organic layers were washed with brine (100 mL×2), dried over $Na_2SO_4$, filtered and concentrated under reduced pressure to give 1-azido-4-trimethylsilylbut-3-ene (5.30 g, crude) as colorless oil. $^1$HNMR (400 MHz, DMSO-$d_6$) δ 6.31-6.24 (m, 1H), 5.64-5.60 (d, J=14.5 Hz, 1H), 3.37 (t, J=6.78 Hz, 1H), 2.40-2.35 (m, 2H), 0.12 (s, 9H).

1-Amino-4-trimethylsilylbut-3-ene. To a solution of 1-azido-4-trimethylsilylbut-3-ene (4.50 g, 26.5 mmol, 1.00 eq.) in methyl tert-butyl ether (50 mL) was added lithium aluminum hydride (1.21 g, 31.9 mmol, 1.20 eq.) at 0° C. The mixture was stirred at 0° C. for 2 hrs. To the mixture was added water (1 ml), then was added NaOH (15%, 1 ml) and water (3 ml) at 0° C., dried over $Na_2SO_4$, filtered and the filtrate was used in the next step. 1-Amino-4-trimethylsilyl-but-3-ene (3.00 g, crude) was obtained as yellow oil.

1-(3-Pyridyl)-N-(4-trimethylsilylbut-3-enyl)methanimine. To a solution of 1-amino-4-trimethylsilylbut-3-ene (3.00 g, 20.9 mmol, 1.00 eq.) in methyl tert-butyl ether (5 mL) was added $MgSO_4$ (17.6 g, 146 mmol, 7.00 eq.) and 3-pyridinecarboxaldehyde (2.24 g, 20.9 mmol, 1.97 mL, 1.00 eq.). The mixture was stirred at 25° C. for 0.5 hr. The reaction mixture was then filtered and concentrated under reduced pressure The residue was purified by reverse phase chromatography (base condition) to get 1-(3-pyridyl)-N-(4-trimethylsilylbut-3 -enyl)methanimine (2.00 g, 8.61 mmol, 41.0% yield) as yellow oil. $^1$HNMR (400 MHz, $CDCl_3$) δ 8.86-8.85 (m, 1H), 8.65-8.64 (m, 1H), 8.31-8.30 (m, 1H), 8.12-8.10 (m, 1H), 7.36-7.27 (m, 1H), 6.34-6.29 (m, 1H), 5.63-5.59 (m, 1H), 3.73-3.70 (m, 2H), 2.56-2.53 (m, 2H), 0.12 (m, 9H).

3-(1,2,3,6-Tetrahydropyridin-6-yl)pyridine. To a solution of 1-(3-pyridyl)-N-(4-trimethylsilylbut-3-enyl)methanimine (2.00 g, 8.61 mmol, 1.00 eq) in acetonitrile (5 mL) was added $Sc(OTf)_3$ (8.47 g, 17.21 mmol, 2.00 eq.). The mixture was stirred at 60° C. for 12 hrs. The reaction mixture was adjusted to pH 9-111. The residue was diluted with water (10 mL) and extracted with dichloromethane (20 mL×2). The combined organic layers were washed with brine (10 mL×2), dried over $Na_2SO_4$, filtered and concentrated under reduced pressure to give a residue. The residue was purified by prep-HPLC (basic condition: column: Waters X bridge C18 150×50 mm, 10 μm; mobile phase: [water (10 mM $NH_4HCO_3$)-acetonitrile]; B %: 5%-30%, 11 min) to give 3-(1,2,3,6-tetrahydropyridin-6-yl)pyridine (102 mg, 7.25% yield, 98.7% purity) as yellow oil; m/z=161.2 $(M+1)^+$; $^1$HNMR (400 MHz, $CDCl_3$) δ 8.60-8.59 (d, J=2.1 Hz, 1H), 8.53-8.52 (dd, J=4.7 Hz, 1H), 7.72-7.70 (m, 1H), 7.28-7.25 (m, 1H), 6.02-5.99 (ddt, J=7.6 Hz 1H), 5.73-5.70 (dd, J=10.1 Hz, 1H), 4.52-4.51 (s, 1H), 3.09-3.00 (m, 2H), 2.26-2.24 (m, 1H), 2.13-2.05 (m, 1H). 3-(1,2,3,6-Tetrahydropyridin-6-yl) pyridine was converted into dihydrochloride salt by treatment with hydrogen chloride solution in diethyl ether.

Compound 7

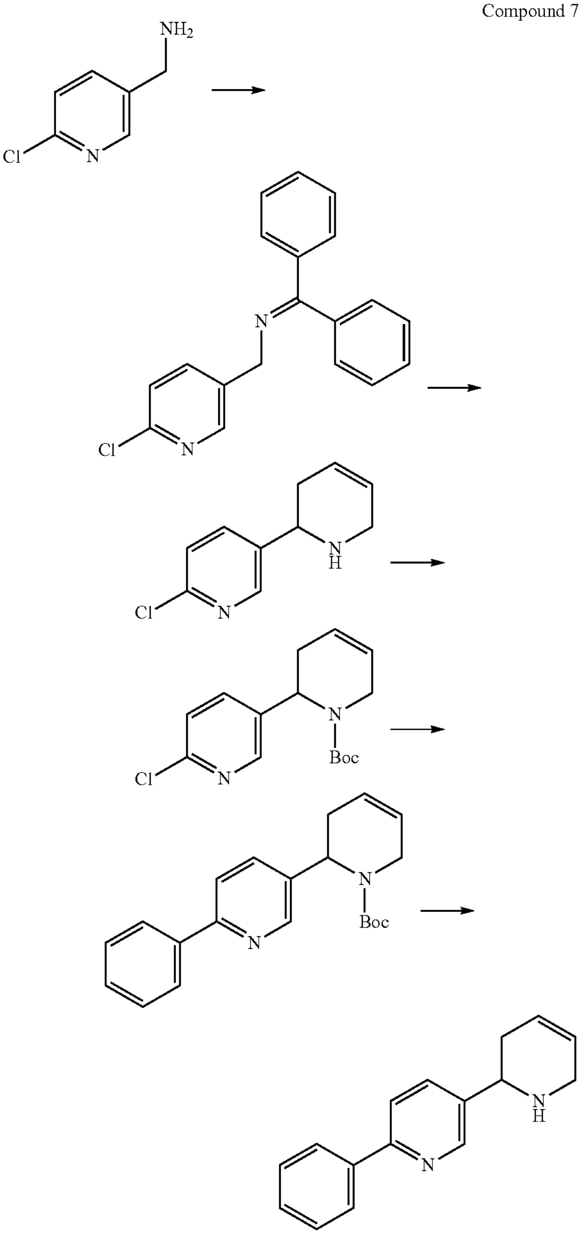

N-[(6-Chloro-3-pyridyl)methyl]-1,1-diphenyl-methanimine. To a solution of (6-chloro-3-pyridyl)methanamine (2.00 g, 11.0 mmol, 1.00 eq), benzophenone (1.57 g, 11.0 mmol, 1.00 eq) in toluene (20 mL) was added p-toluenesulfonic acid (418 mg, 2.20 mmol, 0.200 eq). The mixture was stirred at 110° C. for 10 hrs. The mixture was concentrated. The residue was purified by column chromatography (silica gel, petroleum ether/ethyl acetate=1/0 to 5/1) to get the spot (petroleum ether/ethyl acetate=5/1, Rf=0.5). N-[(6-Chloro-3-pyridyl)methyl]-1,1-diphenyl-methanimine (1.20 g, crude) was obtained as a colorless oil; m/z=307.0 $(M+1)^+$.

2-Chloro-5-(1,2,3,6-tetrahydropyridin-2-yl)pyridine. To a solution of N-[(6-chloro-3-pyridyl)methyl]-1,1-diphenyl-methanimine (982 mg, 3.20 mmol, 1.00 eq) in tetrahydrofuran (10 mL) was added lithium diisopropylamide (2 M, 3.20 mL, 2.00 eq) at −70° C. The mixture was stirred at −70° C. for 0.5 hr and then cis-1,4-dichloro-2-butene (0.400 g, 3.20 mmol, 336 uL, 1.00 eq) was added. The mixture was stirred at 25° C. for 3 hrs. The mixture was quenched with HCl (1 M) (50 mL) and stirred for 0.5 h. Then adjusted pH to 12 with NaOH solution (40%) and extracted with dichloromethane (20 mL×3). The combined organic layers were dried over sodium sulfate, filtered and concentrated. The residue was purified by reversed phase (HCl condition, ISCO®; 40 g SepaFlash® Silica Flash Column, eluent of 0-20% acetonitrile/water, flow rate 40 mL/min) to get 2-chloro-5-(1,2,3,6-tetrahydropyridin-2-yl)pyridine dihydrochloride (100.48 mg, 373 umol, 11.7% yield, 99.4% purity) as a white solid; m/z=195.3 $(M+1)^+$; $^1H$ NMR (400 MHz, MeOD) 8.56-8.55 (d, J=2.8, 1H), 8.05-8.02 (m, 1H), 7.62-7.60 (d, J=8.4, 1H), 6.11-5.89 (m, 2H), 4.66-4.54 (m, 1H), 3.99-3.78 (m, 2H), 2.80-2.64 (m, 2H).

N-tert-Butyloxycarbonyl-2-chloro-5-(1,2,3,6-tetrahydropyridin-2-yl)pyridine. To a solution of 2-chloro-5-(1,2,3,6-tetrahydropyridin-2-yl)pyridine dihydrochloride (100 mg, 513 umol, 1.00 eq) and triethylamine (104 mg, 1.03 mmol, 143 uL, 2.00 eq) in dichloromethane (5 mL) was added di-tert-butyl dicarbonate (135 mg, 616 umol, 142 uL, 1.20 eq). The mixture was stirred at 25° C. for 10 hrs. The mixture was washed with water (20 mL), brine (20 mL). The organic layer was dried over anhydrous sodium sulfate, filtered and concentrated to give a residue. The residue was purified by column chromatography (silica gel, petroleum ether/ethyl acetate=10/1 to 5/1) to get the product (petroleum ether/ethyl acetate=5/1, Rf=0.6) as a yellow oil; m/z=295.3 $(M+1)^+$.

N-tert-Butyloxycarbonyl 2-phenyl-5-(1,2,3,6-tetrahydropyridin-2-yl)pyridine. To a solution of N-tert-butyloxycarbonyl-2-chloro-5-(1,2,3,6-tetrahydropyridin-2-yl)pyridine (160 mg, 543 umol, 1.00 eq), phenylboronic acid (80 mg, 656 umol, 1.21 eq) and $Na_2CO_3$ (2 M, 542 uL, 2.00 eq) in toluene (5 mL) and ethanol (1 mL) was added $Pd(PPh_3)_4$ (314 mg, 271 umol, 0.0500 eq). The mixture was stirred at 90° C. for 3 hrs under $N_2$. The mixture was filtered and the filtrate was poured into water (20 mL) and extracted with ethyl acetate (10 mL×2). The combined organic layers were washed with brine (10 mL), dried over anhydrous sodium sulfate, filtered and concentrated. The residue was purified by column chromatography (silica gel, petroleum ether/ethyl acetate=20/1 to 5/1) to get the product (petroleum ether/ethyl acetate=5/1, Rf=0.65), (170 mg, 505 umol, 93.1% yield) as a colorless oil; m/z=337.4 $(M+1)^+$.

2-Phenyl-5-(1,2,3,6-tetrahydropyridin-2-yl)pyridine. A mixture of N-tert-butyloxycarbonyl 2-phenyl-5-(1,2,3,6-tetrahydropyridin-2-yl)pyridine (170 mg, 505 umol, 1.00 eq), hydrogen chloride solution in ethyl acetate (4 M, 2 mL, 15.8 eq) in ethyl acetate (5 mL) was stirred at 25° C. for 1 hr. The mixture was filtered and the filter cake was washed with EtOAc (20 mL), collected and concentrated to get 2-phenyl-5-(1,2,3,6-tetrahydropyridin-2-yl)pyridine dihydrochloride (67.86 mg, 218 umol, 43.1% yield, 99.3% purity) as off-white solid; m/z= 237.2 $(M+1)^+$; $^1H$ NMR (400 MHz, MeOD) 9.01-9.00 (d, J=2.0, 1H), 8.67-8.65 (m, 1H), 8.43-8.41 (m, 1H), 8.03-8.07 (m, 2H), 7.72-7.67 (m, 3H), 6.15-5.94 (m, 2H), 4.05-3.86 (m, 2H), 2.92-2.73 (m, 2H).

Compound 8

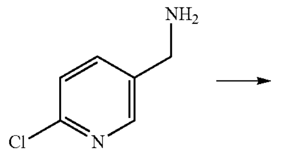

-continued

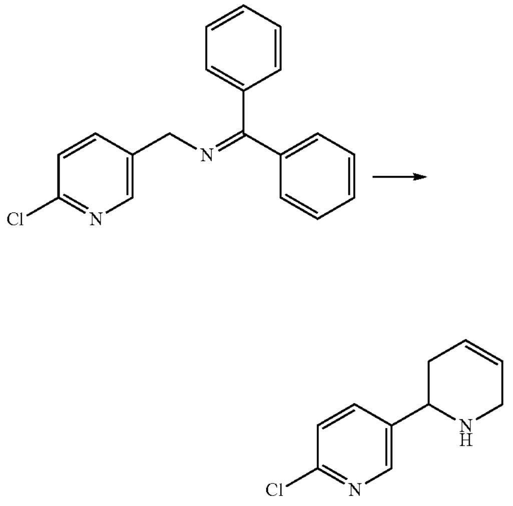

N-[(6-Chloro-3-pyridyl)methyl]-1,1-diphenyl-methanimine. To a solution of (6-chloro-3-pyridyl)methanamine (2.00 g, 11.0 mmol, 1.00 eq), benzophenone (1.57 g, 11.0 mmol, 1.00 eq) in toluene (20 mL) was added p-toluenesulfonic acid (418 mg, 2.20 mmol, 0.200 eq). The mixture was stirred at 110° C. for 10 hrs. The mixture was concentrated. The residue was purified by column chromatography (silica gel, petroleum ether/ethyl acetate=1/0 to 5/1) to get the spot (petroleum ether/ethyl acetate=5/1, Rf=0.5). N-[(6-Chloro-3-pyridyl)methyl]-1,1-diphenyl-methanimine (1.20 g, crude) was obtained as a colorless oil; m/z=307.0 $(M+1)^+$.

2-Chloro-5-(1,2,3,6-tetrahydropyridin-2-yl)pyridine. To a solution of N-[(6-chloro-3-pyridyl)methyl]-1,1-diphenyl-methanimine (982 mg, 3.20 mmol, 1.00 eq) in tetrahydrofuran (10 mL) was added lithium diisopropylamide (2 M, 3.20 mL, 2.00 eq) at −70° C. The mixture was stirred at −70° C. for 0.5 hr and then cis-1,4-dichloro-2-butene (0.400 g, 3.20 mmol, 336 uL, 1.00 eq) was added. The mixture was stirred at 25° C. for 3 hrs. The mixture was quenched with HCl (1 M) (50 mL) and stirred for 0.5 h. Then adjusted pH to 12 with NaOH solution (40%) and extracted with dichloromethane (20 mL×3). The combined organic layers were dried over sodium sulfate, filtered and concentrated. The residue was purified by reversed phase (HCl condition, ISCO®; 40 g SepaFlash® Silica Flash Column, eluent of 0~20% acetonitrile/water, flow rate 40 mL/min) to get 2-chloro-5-(1,2,3,6-tetrahydropyridin-2-yl)pyridine dihydrochloride (100.48 mg, 373 umol, 11.7% yield, 99.4% purity) as a white solid; m/z=195.3 $(M+1)^+$; $^1H$ NMR (400 MHz, MeOD) 8.56-8.55 (d, J=2.8, 1H), 8.05-8.02 (m, 1H), 7.62-7.60 (d, J=8.4, 1H), 6.11-5.89 (m, 2H), 4.66-4.54 (m, 1H), 3.99-3.78 (m, 2H), 2.80-2.64 (m, 2H).

Compound 9

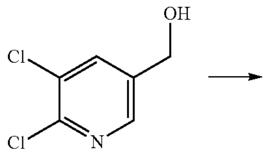

-continued

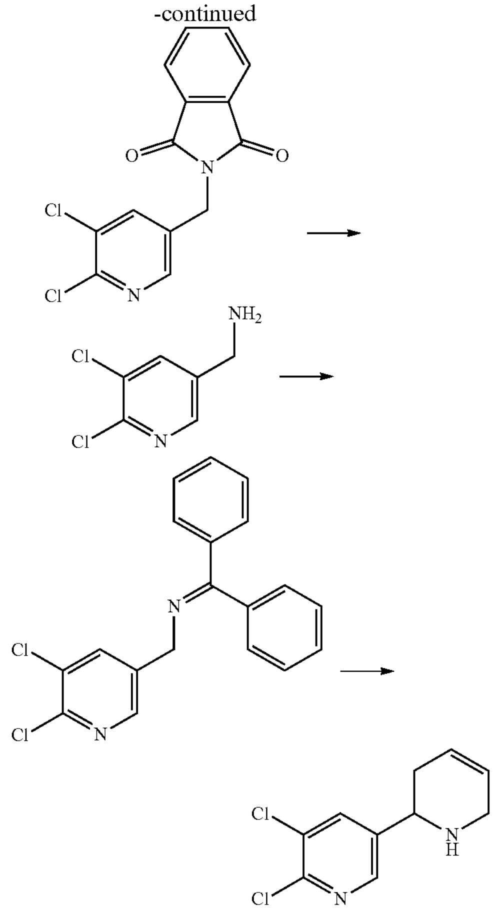

2-[(5,6-Dichloro-3-pyridyl)methyl]isoindoline-1,3-dione. To a solution of (5,6-dichloro-3-pyridyl)methanol (5.00 g, 28.1 mmol, 1.00 eq), phthalimide (4.13 g, 28.1 mmol, 1.00 eq) and $PPh_3$ (11.1 g, 42.1 mmol, 1.50 eq) in tetrahydrofuran (50 mL) was added diethyl azodicarboxylate (7.34 g, 42.1 mmol, 7.66 mL, 1.50 eq) at 0° C. The mixture was stirred at 25° C. for 10 hrs. The mixture was poured into water (200 mL) and then extracted with ethyl acetate (200 mL×3). The combined organic layers were washed with brine (500 mL), dried over anhydrous sodium sulfate, filtered and concentrated to give a residue. The residue was purified by column chromatography (silica gel, petroleum ether/ethyl acetate=50/1 to 5/1) to get 2-[(5,6-dichloro-3-pyridyl)methyl]isoindoline-1,3-dione (petroleum ether/ethyl acetate=3/1, Rf=0.6), (6.00 g, 17.6 mmol, 62.6% yield, 90% purity) as a yellow solid; m/z=307.0 $(M+1)^+$.

(5,6-Dichloro-3-pyridyl)methanamine. A solution of 2-[(5,6-dichloro-3-pyridyl)methyl]isoindoline-1,3-dione (6.00 g, 19.5 mmol, 1.00 eq) and hydrazine hydrate (4.89 g, 97.7 mmol, 4.75 mL, 5.00 eq) in ethanol (60 mL) was heated to 70° C. for 3 hrs. The mixture was concentrated under reduced pressure to give a residue. The crude product was used in the next step without purification. (5,6-Dichloro-3-pyridyl)methanamine (3.00 g, crude) was obtained as a light yellow solid; m/z=177.2 (M+1)+.

N-[(5,6-Dichloro-3-pyridyl)methyl]-1,1-diphenyl-methanimine. To a solution of (5,6-dichloro-3-pyridyl)methanamine (3.00 g, 16.5 mmol, 1.00 eq) and benzophenone (2.91 g, 16.5 mmol, 1.00 eq) in toluene (30 mL) was added p-toluenesulfonic acid (567 mg, 3.29 mmol, 0.200 eq). The mixture was stirred at 110° C. for 10 hrs. The mixture was concentrated under reduced pressure to give a residue. The residue was purified by column chromatography (Silica gel, petroleum ether/ethyl acetate=100/1 to 20/1) to get the product (petroleum ether/ethyl acetate=5/1, Rf=0.6) (1.50 g, crude) as yellow oil; m/z=341.4 $(M+1)^+$.

2,3-Dichloro-5-(1,2,3,6-tetrahydropyridin-2-yl)pyridine. A solution of N-[(5,6-dichloro-3-pyridyl)methyl]-1,1-diphenyl-methanimine (1.36 g, 4.00 mmol, 1.00 eq) in tetrahydrofuran (10 mL) was added lithium diisopropylamide (2 M, 4 mL, 2.00 eq) at −70° C. and stirred for 30 min. Then cis-1,4-dichloro-2-butene (500 mg, 4.00 mmol, 420 uL, 1.00 eq) was added to the mixture. The mixture was warmed to 25° C. and stirred for 8 hrs. The mixture was quenched with HCl (1 M) (50 mL) and stirred for 0.5 h. Then adjust pH to 12 with NaOH solution (40%) and extracted with dichloromethane (20 mL×3). The combined organic layers were dried over sodium sulfate, filtered and concentrated. The residue was purified by reversed phase (HCl condition, ISCO®; 40 g SepaFlash® Silica Flash Column, eluent of 0~20% acetonitrile/Water, flow rate 40 mL/min) to get 2,3-dichloro-5-(1,2,3,6-tetrahydropyridin-2-yl)pyridine dihydrochloride (108.21 mg, 357 umol, 8.93% yield, 99.7% purity) as a light yellow solid; m/z=229.1 $(M+1)^+$; 1H NMR (400 MHz, MeOD) 8.49-8.48 (d, J=2.4, 1H), 8.19-8.18 (d, J=2.0, 1H), 6.12-5.90 (m, 2H), 4.67-4.63 (m, 1H), 4.01-3.80 (m, 2H), 2.75-2.68 (m, 2H).

Compound 10

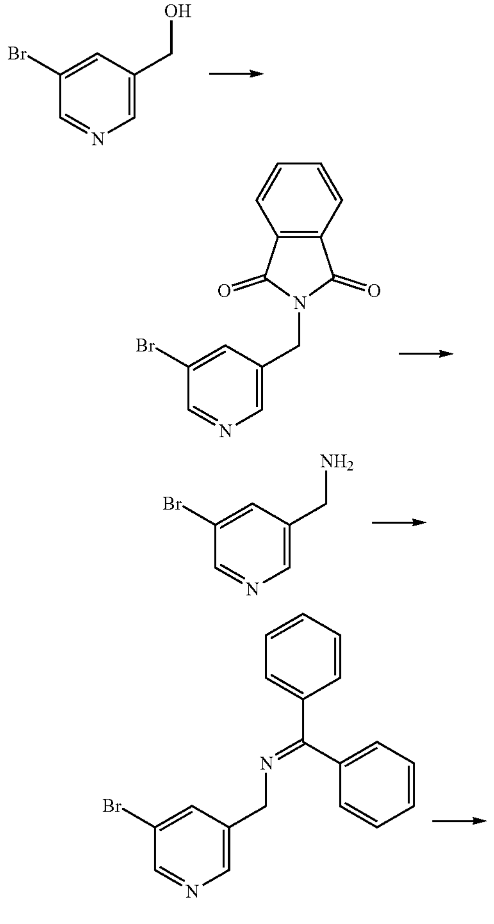

-continued

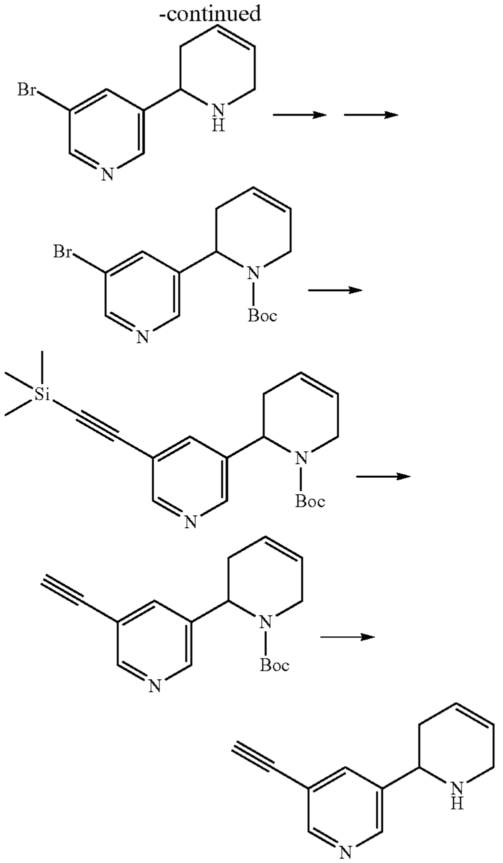

2-[(5-Bromo-3-pyridyl)methyl]isoindoline-1,3-dione. To a solution of (5-bromo-3-pyridyl)methanol (10.0 g, 53.2 mmol, 1.00 eq) and phthalimide (7.83 g, 53.2 mmol, 1.00 eq), PPh3 (20.9 g, 79.8 mmol, 1.50 eq) in tetrahydrofuran (100 mL) was added diethyl azodicarboxylate (13.9 g, 79.8 mmol, 14.5 mL, 1.50 eq) at 0° C. The mixture was stirred at 25° C. for 10 hrs. The mixture was poured into water (200 mL) and then extracted with ethyl acetate (200 mL×3). The combined organic layers were washed with brine (500 mL), dried over anhydrous sodium sulfate, filtered and concentrated to give a residue. The residue was purified by column chromatography (silica gel, petroleum ether/ethyl acetate=50/1 to 5/1) to get 2-[(5-bromo-3-pyridyl)methyl] isoindoline-1,3-dione (14.0 g, 43.7 mmol, 82.2% yield, 99% purity) as a yellow solid, m/z=317.0 $(M+1)^+$.

(5-Bromo-3-pyridyl)methanamine. A mixture of 2-[(5-bromo-3-pyridyl)methyl]isoindoline-1,3-dione (13.0 g, 40.9 mmol, 1.00 eq) and hydrazine hydrate (10.3 g, 205 mmol, 9.96 mL, 5.00 eq) in EtOH (100 mL) was heated at 70° C. for 3 hrs. The mixture was concentrated under reduced pressure to give a residue. The crude product was used in the next step without purification. (5-Bromo-3-pyridyl)methanamine (10.0 g, crude) was obtained as a yellow solid, m/z=189.2 $(M+1)^+$.

N-[(5-Bromo-3-pyridyl)methyl]-1,1-diphenyl-methanimine. To a solution of (5-bromo-3-pyridyl)methanamine (10.0 g, 54.9 mmol, 1.00 eq) and benzophenone (10.3 g, 54.9 mmol, 1.00 eq) in toluene (100 mL) was added p-toluenesulfonic acid (1.89 g, 11.0 mmol, 0.20 eq). The mixture was stirred at 110° C. for 10 hrs. The mixture was concentrated under reduced pressure to give a residue. The residue was purified by column chromatography (silica gel, Petroleum ether/Ethyl acetate=100/1 to 10/1) to get N-[(5-bromo-3-pyridyl)methyl]-1,1-diphenyl-methanimine (15.0 g, crude) as yellow oil.

3-Bromo-5-(1,2,3,6-tetrahydropyridin-2-yl)pyridine. A solution of N-[(5-bromo-3-pyridyl)methyl]-1,1-diphenyl-methanimine (14.1 g, 40.0 mmol, 1.00 eq) in tetrahydrofuran (50 mL) was added lithium diisopropylamide (2 M, 40 mL, 2.00 eq) at −70° C. and stirred for 30 mins. Then cis-1,4-dichloro-2-butene (5.00 g, 40.0 mmol, 4.2 mL, 1.00 eq) was added to the mixture. The mixture was warmed to 25° C. for 8 hrs. The mixture was quenched with HCl (1 M) (100 mL) and stirred for 0.5 h. Then adjust pH to 12 with NaOH solution (40%) and extracted with dichloromethane (50 mL×3). The combined organic layers were dried over sodium sulfate, filtered and concentrated. The residue was purified by reversed phase (basic condition, ISCO®; 40 g SepaFlash® Silica Flash Column, Eluent of 0~20% acetonitrile/water, flow rate 40 mL/min) to get 3-bromo-5-(1,2,3,6-tetrahydropyridin-2-yl)pyridine (1.10 g, 4.57 mmol, 11.4% yield, 99.4% purity) as yellow oil, m/z=239.2 $(M+1)^+$.

N-tert-Butyloxycarbonyl-3-bromo-5-(1,2,3,6-tetrahydropyridin-2-yl)pyridine. To a solution of 3-bromo-5-(1,2,3,6-tetrahydropyridin-2-yl)pyridine (1.10 g, 4.57 mmol, 1.00 eq) and 4-(dimethylamino)pyridine (56 mg, 457 umol, 0.100 eq) in dichloromethane (10 mL) was added triethylamine (1.39 g, 13.7 mmol, 1.91 mL, 3.00 eq) and di-tert-butyl dicarbonate (998 mg, 4.57 mmol, 1.05 mL, 1.00 eq). The mixture was stirred at 25° C. for 10 hrs. The mixture was washed with brine (30 mL), dried over $Na_2SO_4$, filtered and concentrated to give a residue. The residue was purified by column chromatography (silica gel, petroleum ether/ethyl acetate=20/1 to 10/1) to get the product (1.10 g, 3.15 mmol, 68.9% yield, 97.2% purity) as a light yellow oil, m/z=339.2 $(M+1)^+$.

tert-Butyl 2-[5-(2-trimethylsilylethynyl)-3-pyridyl]-3,6-dihydro-2H-pyridine-1-carboxylate. To a solution of N-tert-butyloxycarbonyl-3-bromo-5-(1,2,3,6-tetrahydropyridin-2-yl)pyridine (300 mg, 884 umol, 1.00 eq), CuI (17 mg, 88.4 umol, 0.100 eq), $Pd(PPh_3)_2Cl_2$ (62 mg, 88.4 umol, 0.10 eq) in N,N-dimethylformamide (10 mL) was added triethylamine (358 mg, 3.54 mmol, 492 uL, 4.00 eq). Then ethynyl (trimethyl)silane (104 mg, 1.06 mmol, 147 uL, 1.20 eq) was added to the mixture and the mixture was stirred at 25° C. for 3 hrs. The mixture was poured into water (30 mL) and extracted with ethyl acetate (15 mL). The organic layer was dried over anhydrous sodium sulfate, filtered and concentrated to get a residue. The residue was purified by column chromatography (silica gel, petroleum ether/ethyl acetate=20/1) to obtain tert-butyl 2-[5-(2-trimethylsilylethynyl)-3-pyridyl]-3,6-dihydro-2H-pyridine-1-carboxylate (300 mg, crude) as a brown oil, m/z=357.4 $(M+1)^+$.

tert-Butyl 2-(5-ethynyl-3-pyridyl)-3,6-dihydro-2H-pyridine-1-carboxylate. To a solution of tert-butyl 2-[5-(2-trimethylsilylethynyl)-3-pyridyl]-3,6-dihydro-2H-pyridine-1-carboxylate (300 mg, 841 umol, 1.00 eq) in methanol (3 mL) and dichloromethane (6 mL) was added $K_2CO_3$ (348 mg, 2.52 mmol, 2.99 eq). The mixture was stirred at 25° C. for 2 hrs. The reaction mixture was concentrated under reduced pressure to remove solvent. Then the residue was diluted with water (10 mL) and extracted with dichloromethane (10 mL×2). The combined organic layers were dried over anhydrous sodium sulfate, filtered and concentrated under reduced pressure to give a residue. The residue was purified by preparative TLC (SiO2, petroleum ether/ethyl acetate=2/1) to get the product (Rf=0.60) (140 mg, 492 umol, 58.5% yield) as a yellow oil; $^1H$ NMR (400 MHz, $CDCl_3$) 8.58-

8.51 (m, 2H), 7.68 (s, 1H), 5.92-5.89 (m, 2H), 5.71-5.54 (m, 1H), 4.26-4.22 (m, 1H), 3.36-3.32 (m, 1H), 3.21 (s, 1H), 2.77-2.47 (m, 2H), 1.49 (s, 9H).

2-(5-ethynyl-3-pyridyl)-3,6-dihydro-2H-pyridine. To a solution of tert-butyl 2-(5-ethynyl-3-pyridyl)-3,6-dihydro-2H-pyridine-1-carboxylate (140 mg, 492 umol, 1.00 eq) in ethyl acetate (5 mL) was added solution of hydrogen chloride in ethyl acetate (4 M, 3 mL, 24.4 eq). The mixture was stirred at 25° C. for 2 hrs. The mixture was concentrated under reduced pressure to give a residue. The residue was stirred in ethyl acetate (20 mL) for 0.5 hr, filtered and the solid was collected to get target 2-(5-ethynyl-3-pyridyl)-3,6-dihydro-2H-pyridine dihydrochloride (77.64 mg, 282 umol, 57.3% yield, 93.4% purity) as a brown solid; m/z=185.3 $(M+1)^+$; $^1H$ NMR (400 MHz, MeOD) 9.01-8.88 (m, 2H), 8.58 (s, 1H), 6.13-5.92 (m, 2H), 4.82-4.77 (m, 1H), 4.32 (s, 1H), 4.25-4.03 (m, 1H), 4.00-3.99 (m, 1H), 2.86-2.73 (m, 2H)

Compound 11

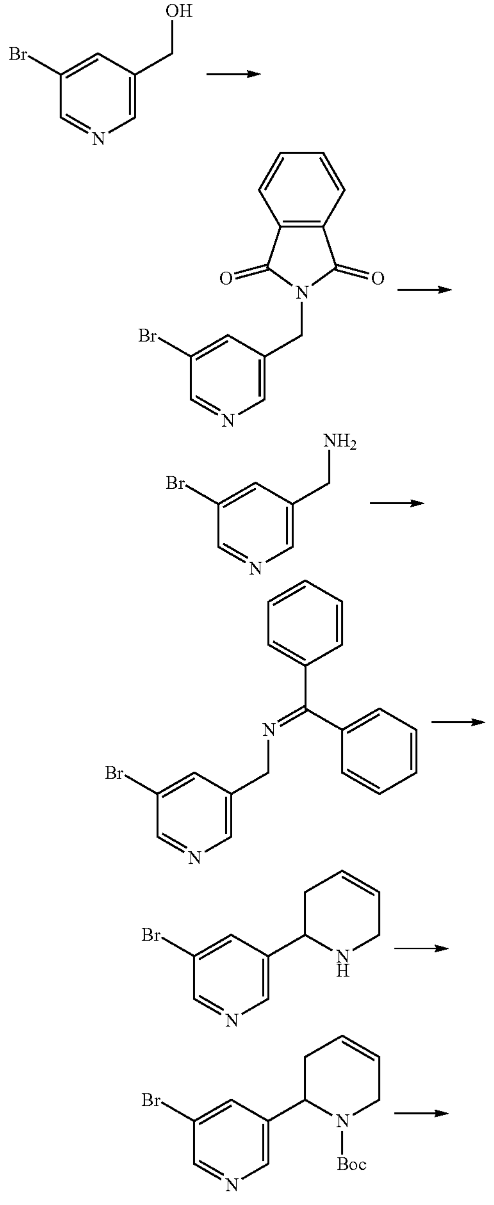

-continued

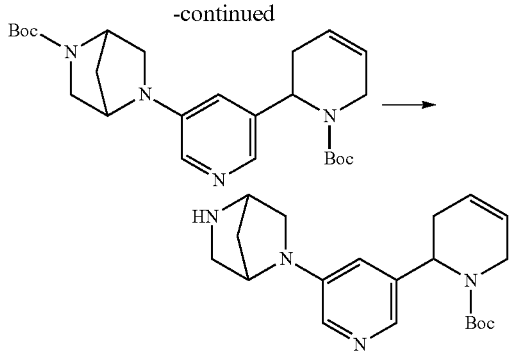

2-[(5-Bromo-3-pyridyl)methyl]isoindoline-1,3-dione. To a solution of (5-bromo-3-pyridyl)methanol (10.0 g, 53.2 mmol, 1.00 eq) and phthalimide (7.83 g, 53.2 mmol, 1.00 eq), PPh3 (20.9 g, 79.8 mmol, 1.50 eq) in tetrahydrofuran (100 mL) was added diethyl azodicarboxylate (13.9 g, 79.8 mmol, 14.5 mL, 1.50 eq) at 0° C. The mixture was stirred at 25° C. for 10 hrs. The mixture was poured into water (200 mL) and then extracted with ethyl acetate (200 mL×3). The combined organic layers were washed with brine (500 mL), dried over anhydrous sodium sulfate, filtered and concentrated to give a residue. The residue was purified by column chromatography (silica gel, petroleum ether/ethyl acetate=50/1 to 5/1) to get 2-[(5-bromo-3-pyridyl)methyl] isoindoline-1,3-dione (14.0 g, 43.7 mmol, 82.2% yield, 99% purity) as a yellow solid, m/z=317.0 $(M+1)^+$.

(5-Bromo-3-pyridyl)methanamine. A mixture of 2-[(5-bromo-3-pyridyl)methyl]isoindoline-1,3-dione (13.0 g, 40.9 mmol, 1.00 eq) and hydrazine hydrate (10.3 g, 205 mmol, 9.96 mL, 5.00 eq) in EtOH (100 mL) was heated at 70° C. for 3 hrs. The mixture was concentrated under reduced pressure to give a residue. The crude product was used in the next step without purification. (5-Bromo-3-pyridyl)methanamine (10.0 g, crude) was obtained as a yellow solid, m/z=189.2 $(M+1)^+$.

N-[(5-Bromo-3-pyridyl)methyl]-1,1-diphenyl-methanimine. To a solution of (5-bromo-3-pyridyl)methanamine (10.0 g, 54.9 mmol, 1.00 eq) and benzophenone (10.3 g, 54.9 mmol, 1.00 eq) in toluene (100 mL) was added p-toluenesulfonic acid (1.89 g, 11.0 mmol, 0.20 eq). The mixture was stirred at 110° C. for 10 hrs. The mixture was concentrated under reduced pressure to give a residue. The residue was purified by column chromatography (silica gel, Petroleum ether/Ethyl acetate=100/1 to 10/1) to get N-[(5-bromo-3-pyridyl)methyl]-1,1-diphenyl-methanimine (15.0 g, crude) as yellow oil.

3-Bromo-5-(1,2,3,6-tetrahydropyridin-2-yl)pyridine. A solution of N-[(5-bromo-3-pyridyl)methyl]-1,1-diphenyl-methanimine (14.1 g, 40.0 mmol, 1.00 eq) in tetrahydrofuran (50 mL) was added lithium diisopropylamide (2 M, 40 mL, 2.00 eq) at −70° C. and stirred for 30 mins. Then cis-1,4-dichloro-2-butene (5.00 g, 40.0 mmol, 4.2 mL, 1.00 eq) was added to the mixture. The mixture was warmed to 25° C. for 8 hrs. The mixture was quenched with HCl (1 M) (100 mL) and stirred for 0.5 h. Then adjust pH to 12 with NaOH solution (40%) and extracted with dichloromethane (50 mL×3). The combined organic layers were dried over sodium sulfate, filtered and concentrated. The residue was purified by reversed phase (basic condition, ISCO®; 40 g SepaFlash® Silica Flash Column, Eluent of 0~20% acetonitrile/water, flow rate 40 mL/min) to get 3-bromo-5-(1,2,3, 6-tetrahydropyridin-2-yl)pyridine (1.10 g, 4.57 mmol, 11.4% yield, 99.4% purity) as yellow oil, m/z=239.2 $(M+1)^+$.

N-tert-Butyloxycarbonyl-3-bromo-5-(1,2,3,6-tetrahydro-pyridin-2-yl)pyridine. To a solution of 3-bromo-5-(1,2,3,6-tetrahydropyridin-2-yl)pyridine (1.10 g, 4.57 mmol, 1.00 eq) and 4-(dimethylamino)pyridine (56 mg, 457 umol, 0.100 eq) in dichloromethane (10 mL) was added triethylamine (1.39 g, 13.7 mmol, 1.91 mL, 3.00 eq) and di-tert-butyl dicarbonate (998 mg, 4.57 mmol, 1.05 mL, 1.00 eq). The mixture was stirred at 25° C. for 10 hrs. The mixture was washed with brine (30 mL), dried over $Na_2SO_4$, filtered and concentrated to give a residue. The residue was purified by column chromatography (silica gel, petroleum ether/ethyl acetate=20/1 to 10/1) to get the product (1.10 g, 3.15 mmol, 68.9% yield, 97.2% purity) as a light yellow oil, m/z=339.2 $(M+1)^+$.

tert-Butyl 5-[5-(1-tert-butoxycarbonyl-3,6-dihydro-2H-pyridin-2-yl)-3-pyridyl]-2,5-diazabicyclo[2.2.1]heptane-2-carboxylate. To a solution of N-tert-butyloxycarbonyl-3-bromo-5-(1,2,3,6-tetrahydropyridin-2-yl)pyridine (200 mg, 589 umol, 1.00 eq) in toluene (10 mL) was added tert-butyl 2,5-diazabicyclo[2.2.1]heptane-2-carboxylate (117 mg, 590 umol, 1.0 eq), t-BuONa (85 mg, 884 umol, 1.50 eq), tris(dibenzylideneacetone)dipalladium(0) (54 mg, 58.9 umol, 0.100 eq) and Xantphos (34 mg, 58.9 umol, 0.1 eq). The mixture was stirred at 100° C. for 3 hrs under $N_2$. The mixture was poured into water (30 mL) and extracted with ethyl acetate (15 mL). The organic layer was dried over anhydrous sodium sulfate, filtered and concentrated to get a residue. The residue was purified by column chromatography (silica gel, petroleum ether/ethyl acetate=20/1 to 5/1) to get the product (petroleum ether/ethyl acetate=5/1, Rf=0.25), 120 mg, 244 umol, 41.5% yield, 93.0% as yellow oil; m/z=457.4 $(M+1)^+$.

2-[5-(1,2,3,6-Tetrahydropyridin-2-yl)-3-pyridyl]-2,5-diazabicyclo[2.2.1]heptane. To a solution of tert-butyl 5-[5-(1-tert-butoxycarbonyl-3,6-dihydro-2H-pyridin-2-yl)-3-pyridyl]-2,5-diazabicyclo[2.2.1]heptane-2-carboxylate (120 mg, 263 umol, 1.00 eq) in ethyl acetate (5 mL) was added solution of hydrogen chloride in ethyl acetate (4 M, 3.00 mL, 45.6 eq). The mixture was stirred at 25° C. for 1 hr. The mixture was concentrated under reduced pressure to give a residue. The residue was purified by preparative HPLC (HCl condition; column: Phenomenex Synergi C18 150*25*10 um; mobile phase: [water (0.05% HCl)-acetonitrile]; B %: 0%-10%, 5 min) to obtain 2-[5-(1,2,3,6-tetrahydropyridin-2-yl)-3-pyridyl]-2,5-diazabicyclo[2.2.1]heptane dihydrochloride (48.94 mg, 130 umol, 49.6% yield, 97.4% purity) as a yellow gum; m/z=257.0 $(M+1)^+$; $^1$H NMR (400 MHz, MeOD) 8.35-8.25 (m, 2H), 8.21-8.18 (m, 1H), 6.13-5.91 (m, 2H), 5.02 (s, 1H), 4.77-4.67 (m, 2H), 4.02-3.84 (m, 4H), 3.77-3.45 (m, 2H), 2.89-2.68 (m, 2H), 2.38-2.19 (m, 2H).

Compound 12

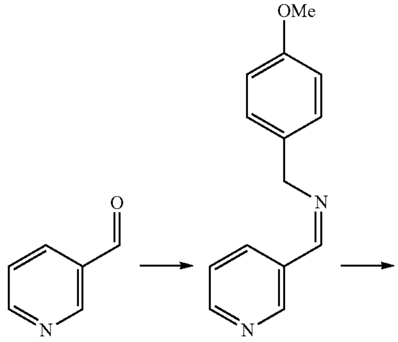

-continued

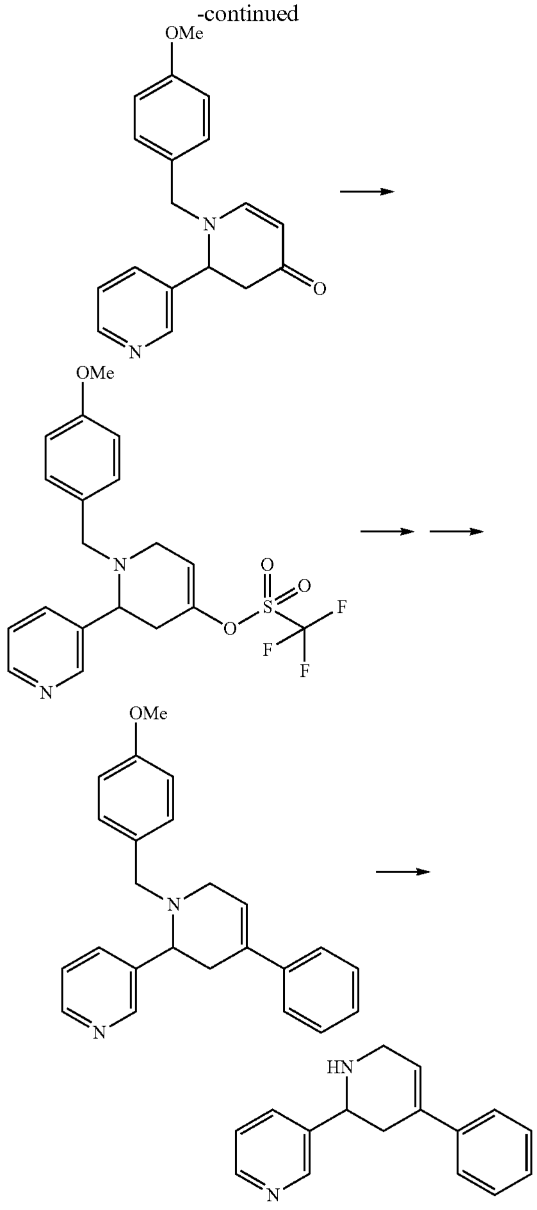

N-(p-Tolylmethyl)-1-(3-pyridyl)methanimine. To a solution of pyridine-3-carbaldehyde (13.7 g, 100 mmol, 12.9 mL, 1.00 eq) in 2-propanol (250 mL), p-methoxybenzylamine (16.1 g, 150 mmol, 14.1 mL, 1.50 eq) and acetic acid (1.50 g, 25.0 mmol, 1.43 mL, 0.25 eq) were added. The reaction mixture was stirred at 25° C. for 1.5 hrs. The reaction mixture was concentrated and then diluted with ethyl acetate (150 mL). The resulting solution was washed with saturated $NaHCO_3$ solution (50 mL×2) and brine (50 mL×2), dried over anhydrous $Na_2SO_4$, filtered and concentrated. N-(p-tolylmethyl)-1-(3-pyridyl)methanimine (28.1 g, crude) was obtained as a brown oil and used into the next step without further purification.

1-(p-Tolylmethyl)-2-(3-pyridyl)-2,3-dihydropyridin-4-one. To a solution of N-(p-tolylmethyl)-1-(3-pyridyl)methanimine (19.5 g, 86.2 mmol, 1.00 eq) in dry tetrahydrofuran (450 mL) was added a solution of $ZnCl_2$ (12.9 g, 94.8 mmol, 4.44 mL, 1.10 eq) in tetrahydrofuran (50 mL) and dichloromethane (50 mL) at −78° C. and stirred for 10 mins. Then 1-methoxy-3-[(trimethylsilyl)oxy]-1,3-butadiene (18.6 g, 108 mmol, 21.0 mL, 1.25 eq) was added to the mixture, and after stirring for 30 mins the mixture was allowed to warm up to −20° C. and stirred for 20 mins. Then the reaction mixture was allowed to warm to 25° C. and stirred for 12 hrs. The reaction mixture was quenched with saturated $NaHCO_3$ (400 mL) and extracted with ethyl acetate (150 mL×2). The combined organic phase was acidified with 1 M HCl (400 mL). The resulting aqueous phase was separated and further washed with ethyl acetate (400 mL). Then the aqueous phase was neutralized with saturated $NaHCO_3$ (400 mL) and extracted with ethyl acetate (150 mL×2). The combined organic phase was dried over anhydrous $Na_2SO_4$, filtered and concentrated. The residue was purified by flash silica gel chromatography (ISCO®; 330 g SepaFlash® Silica Flash Column, Eluent of 0~80% ethyl acetate/petroleum ether gradient, flow rate 100 mL/min) to obtain 1-(p-tolylmethyl)-2-(3-pyridyl)-2,3-dihydropyridin-4-one (13.4 g, 45.4 mmol, 52.6% yield) as a yellow oil; $^1H$ NMR (400 MHz, $CDCl_3$) 8.59-8.45 (m, 2H), 7.66-7.63 (m, 1H), 7.27-7.05 (m, 2H), 7.05-7.03 (m, 2H), 6.89-6.87 (m, 2H), 5.11-5.09 (m, 1H), 4.53-4.49 (m, 1H), 4.36-4.31 (m, 1H), 4.09-3.81 (m, 1H), 3.80 (s, 3H), 2.91-2.85 (m, 1H), 2.63-2.56 (m, 1H).

[1-(p-Tolylmethyl)-2-(3-pyridyl)-3,6-dihydro-2H-pyridin-4-yl]trifluoromethanesulfonate. To a solution of 1-(p-tolylmethyl)-2-(3-pyridyl)-2,3-dihydropyridin-4-one (11.0 g, 37.4 mmol, 1.00 eq) and N,N-bis(trifluoromethylsulfonyl) aniline (14.7 g, 41.1 mmol, 1.10 eq) in tetrahydrofuran (50 mL), L-selectride (1 M, 41.1 mL, 1.10 eq) was added dropwise at −78° C. After 1 h, the solution was allowed to warm up to 25° C. and stirred for another hour. The reaction mixture was quenched with saturated $NH_4Cl$ solution (500 mL) and extracted with ethyl acetate (300 mL×2). The combined organic phase was washed with brine (500 mL), dried over anhydrous $Na_2SO_4$, filtered and concentrated to obtain a brown residue. The residue was purified by column chromatography (silica gel, Petroleum ether/Ethyl acetate=30/1 to 3/1) to get [1-(p-tolylmethyl)-2-(3-pyridyl)-3,6-dihydro-2H-pyridin-4-yl]trifluoromethanesulfonate (Petroleum ether/Ethyl acetate=3/1, Rf=0.6) (5.20 g, 12.1 mmol, 32.5% yield) as a yellow oil; $^1H$ NMR (400 MHz, $CDCl_3$) 8.65-8.57 (m, 2H), 7.79-7.77 (m, 1H), 7.36-7.33 (m, 1H), 7.27-7.18 (m, 2H), 6.87-6.84 (m, 2H), 6.01-5.55 (m, 1H), 3.94-3.91 (m, 1H), 3.80 (s, 3H), 3.62-3.58 (m, 1H), 3.26-3.17 (m, 1H), 3.14-3.06 (m, 2H), 2.73-2.71 (m, 2H).

3-[4-Phenyl-1-(p-tolylmethyl)-3,6-dihydro-2H-pyridin-2-yl]pyridine. To a solution of [1-(p-tolylmethyl)-2-(3-pyridyl)-3,6-dihydro-2H-pyridin-4-yl]trifluoromethanesulfonate (500 mg, 1.17 mmol, 1.00 eq), phenylboronic acid (427 mg, 3.50 mmol, 3.00 eq) in dioxane (10 mL) and $H_2O$ (2 mL) was added $K_2CO_3$ (484 mg, 3.50 mmol, 700 uL, 3.00 eq) and bis(triphenylphosphine)palladium(II) dichloride (85 mg, 116 umol, 0.100 eq). The mixture was stirred at 80° C. for 2 hrs. The mixture was poured into water (30 mL) and then extracted with Ethyl acetate (15 mL×2). The combined organic layers were washed with brine (20 mL), dried over anhydrous sodium sulfate, filtered and concentrated to give a residue. The residue was purified by column chromatography (silica gel, Petroleum ether/Ethyl acetate=20/1 to 5/1) to yield 3-[4-phenyl-1-(p-tolylmethyl)-3,6-dihydro-2H-pyridin-2-yl]pyridine (Petroleum ether/Ethyl acetate=1/1, Rf=0.4) (0.400 g, crude) as a yellow solid; m/z=357.4 $(M+1)^+$.

3-(4-phenyl-1,2,3,6-tetrahydropyridin-2-yl)pyridine.

3-[4-Phenyl-1-(p-tolylmethyl)-3,6-dihydro-2H-pyridin-2-yl]pyridine (400 mg, 1.12 mmol, 1.00 eq) and trifluoroacetic acid (7.70 g, 67.5 mmol, 5 mL, 60.2 eq) were taken up into a microwave tube. The sealed tube was heated at 100° C. for 2 hrs under microwave. The mixture was concentrated under reduced pressure to give a residue. The residue was purified by reverse phase (0.1% HCl) to yield 3-(4-phenyl-1,2,3,6-tetrahydropyridin-2-yl)pyridine dihydrochloride (94.15 mg); m/z=237.1 $(M+1)^+$; $^1H$ NMR (400 MHz, MeOD) 9.24-9.16 (m, 1H), 9.03-9.01 (m, 1H), 8.97-8.95 (m, 1H), 8.29-8.26 (m, 1H), 7.60-7.54 (m, 2H), 7.43-7.38 (m, 3H), 6.31-6.29 (m, 1H), 5.72-5.71 (m, 0.4H), 5.09-5.05 (m, 0.6H), 4.19-4.11 (m, 1H), 3.62-3.61 (m, 1H), 3.28-2.99 (m, 2H).

Compound 13

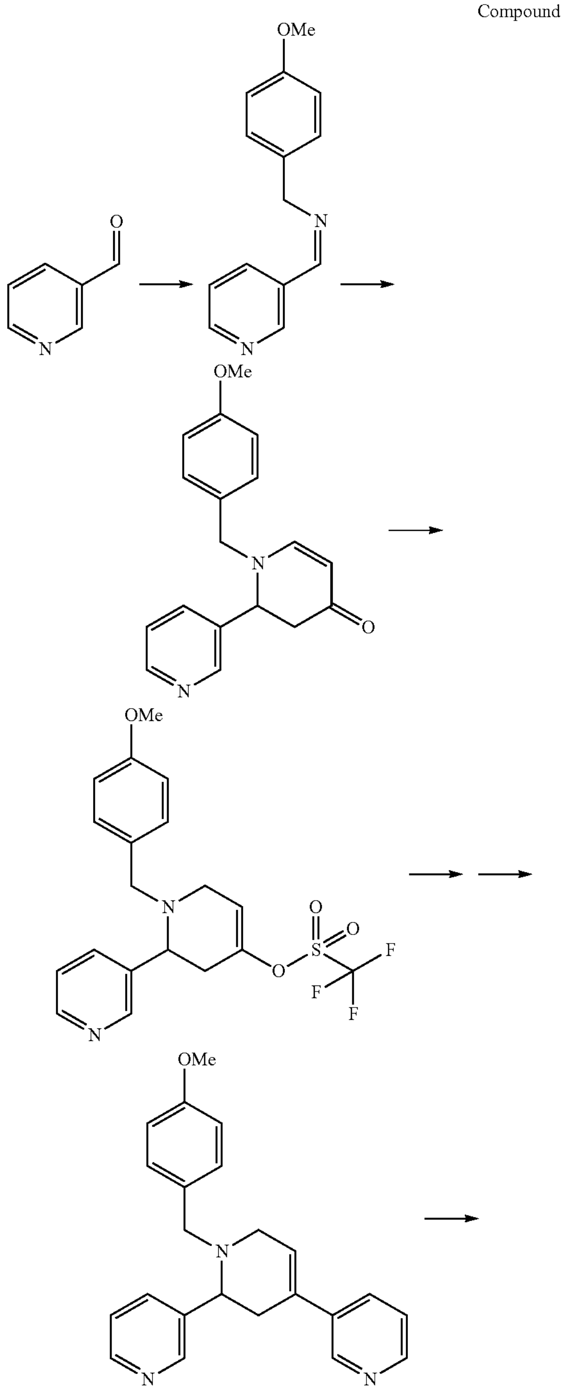

-continued

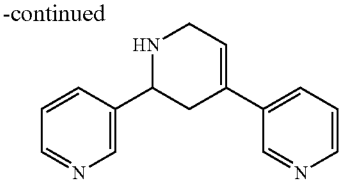

N-(p-Tolylmethyl)-1-(3-pyridyl)methanimine. To a solution of pyridine-3-carbaldehyde (13.7 g, 100 mmol, 12.9 mL, 1.00 eq) in 2-propanol (250 mL), p-methoxybenzylamine (16.1 g, 150 mmol, 14.1 mL, 1.50 eq) and acetic acid (1.50 g, 25.0 mmol, 1.43 mL, 0.25 eq) were added. The reaction mixture was stirred at 25° C. for 1.5 hs. The reaction mixture was concentrated and then diluted with ethyl acetate (150 mL). The resulting solution was washed with saturated $NaHCO_3$ solution (50 mL×2) and brine (50 mL×2), dried over anhydrous $Na_2SO_4$, filtered and concentrated. N-(p-tolylmethyl)-1-(3-pyridyl)methanimine (28.1 g, crude) was obtained as a brown oil and used into the next step without further purification.

1-(p-Tolylmethyl)-2-(3-pyridyl)-2,3-dihydropyridin-4-one. To a solution of N-(p-tolylmethyl)-1-(3-pyridyl)methanimine (19.5 g, 86.2 mmol, 1.00 eq) in dry tetrahydrofuran (450 mL) was added a solution of $ZnCl_2$ (12.9 g, 94.8 mmol, 4.44 mL, 1.10 eq) in tetrahydrofuran (50 mL) and dichloromethane (50 mL) at −78° C. and stirred for 10 mins. Then 1-methoxy-3-[(trimethylsilyl)oxy]-1,3-butadiene (18.6 g, 108 mmol, 21.0 mL, 1.25 eq) was added to the mixture, and after stirring for 30 mins the mixture was allowed to warm up to −20° C. and stirred for 20 mins. Then the reaction mixture was allowed to warm to 25° C. and stirred for 12 hrs. The reaction mixture was quenched with saturated $NaHCO_3$ (400 mL) and extracted with ethyl acetate (150 mL×2). The combined organic phase was acidified with 1 M HCl (400 mL). The resulting aqueous phase was separated and further washed with ethyl acetate (400 mL). Then the aqueous phase was neutralized with saturated $NaHCO_3$ (400 mL) and extracted with ethyl acetate (150 mL×2). The combined organic phase was dried over anhydrous $Na_2SO_4$, filtered and concentrated. The residue was purified by flash silica gel chromatography (ISCO®; 330 g SepaFlash® Silica Flash Column, Eluent of 0~80% ethyl acetate/petroleum ether gradient, flow rate 100 mL/min) to obtain 1-(p-tolylmethyl)-2-(3-pyridyl)-2,3-dihydropyridin-4-one (13.4 g, 45.4 mmol, 52.6% yield) as a yellow oil; $^1$H NMR (400 MHz, $CDCl_3$) 8.59-8.45 (m, 2H), 7.66-7.63 (m, 1H), 7.27-7.05 (m, 2H), 7.05-7.03 (m, 2H), 6.89-6.87 (m, 2H), 5.11-5.09 (m, 1H), 4.53-4.49 (m, 1H), 4.36-4.31 (m, 1H), 4.09-3.81 (m, 1H), 3.80 (s, 3H), 2.91-2.85 (m, 1H), 2.63-2.56 (m, 1H).

[1-(p-Tolylmethyl)-2-(3-pyridyl)-3,6-dihydro-2H-pyridin-4-yl]trifluoromethanesulfonate. To a solution of 1-(p-tolylmethyl)-2-(3-pyridyl)-2,3-dihydropyridin-4-one (11.0 g, 37.4 mmol, 1.00 eq) and N,N-bis(trifluoromethylsulfonyl) aniline (14.7 g, 41.1 mmol, 1.10 eq) in tetrahydrofuran (50 mL), L-selectride (1 M, 41.1 mL, 1.10 eq) was added dropwise at −78° C. After 1 h, the solution was allowed to warm up to 25° C. and stirred for another hour. The reaction mixture was quenched with saturated $NH_4Cl$ solution (500 mL) and extracted with ethyl acetate (300 mL×2). The combined organic phase was washed with brine (500 mL), dried over anhydrous $Na_2SO_4$, filtered and concentrated to obtain a brown residue. The residue was purified by column chromatography (silica gel, Petroleum ether/Ethyl acetate=30/1 to 3/1) to get [1-(p-tolylmethyl)-2-(3-pyridyl)-3,6-dihydro-2H-pyridin-4-yl]trifluoromethanesulfonate (Petroleum ether/Ethyl acetate=3/1, Rf=0.6) (5.20 g, 12.1 mmol, 32.5% yield) as a yellow oil; $^1$H NMR (400 MHz, $CDCl_3$) 8.65-8.57 (m, 2H), 7.79-7.77 (m, 1H), 7.36-7.33 (m, 1H), 7.27-7.18 (m, 2H), 6.87-6.84 (m, 2H), 6.01-5.55 (m, 1H), 3.94-3.91 (m, 1H), 3.80 (s, 3H), 3.62-3.58 (m, 1H), 3.26-3.17 (m, 1H), 3.14-3.06 (m, 2H), 2.73-2.71 (m, 2H).

3-[1-(p-Tolylmethyl)-2-(3-pyridyl)-3,6-dihydro-2H-pyridin-4-yl]pyridine. To a solution of [1-(p-tolylmethyl)-2-(3-pyridyl)-3,6-dihydro-2H-pyridin-4-yl]trifluoromethanesulfonate (500 mg, 1.17 mmol, 1.00 eq) and 3-pyridinylboronic acid (430 mg, 3.50 mmol, 3.00 eq) in water (2 mL) and dioxane (8 mL) was added $K_2CO_3$ (2 M, 1.75 mL, 3.00 eq) and bis(triphenylphosphine)palladium(II) dichloride (85 mg, 117 umol, 0.100 eq). The mixture was stirred at 80° C. for 2 hrs. The mixture was poured into water (30 mL) and then extracted with ethyl acetate (15 mL×2). The combined organic layers were washed with brine (20 mL), dried over anhydrous sodium sulfate, filtered and concentrated to give a residue. The residue was purified by column chromatography (SiO2, Petroleum ether/Ethyl acetate=10/1 to 2/1) to yield 3-[1-(p-tolylmethyl)-2-(3-pyridyl)-3,6-dihydro-2H-pyridin-4-yl]pyridine (TLC: Petroleum ether/Ethyl acetate=0/1, Rf=0.3) (0.330 g, crude) as a yellow oil; m/z=358.3 $(M+1)^+$.

3-[2-(3-Pyridyl)-1,2,3,6-tetrahydropyridin-4-yl]pyridine. 3-[1-(p-tolylmethyl)-2-(3-pyridyl)-3,6-dihydro-2H-pyridin-4-yl]pyridine (0.330 g, 923 umol, 1.00 eq) and trifluoroacetic acid (7.70 g, 67.5 mmol, 5 mL, 73.2 eq) were taken up into a microwave tube. The sealed tube was heated at 100° C. for 2 hrs under microwave. The mixture was concentrated under reduced pressure to give a residue. The residue was purified by reverse phase (0.1% HCl) to yield 3-[2-(3-pyridyl)-1,2,3,6-tetrahydropyridin-4-yl]pyridine dihydrochloride (177 mg, 555 umol, 60.1% yield, 97.2% purity) as a light yellow solid; m/z=238.2 $(M+1)^+$; $^1$H NMR (400 MHz, DMSO-$d_6$) 11.03 (s, 1H), 10.49 (s, 1H), 9.17-9.06 (m, 1H), 9.06-8.91 (m, 1H), 8.90-8.84 (m, 1H), 8.82-8.76 (m, 1H), 8.76-8.65 (m, 1H), 8.65-8.50 (m, 1H), 8.03-7.99 (m, 2H), 6.75 (s, 1H), 4.86 (s, 1H), 4.10-3.97 (m, 2H), 3.30-3.23 (m, 1H), 3.14-3.09 (m, 1H).

Compound 14

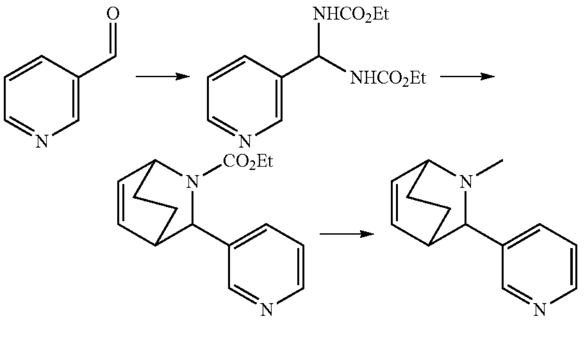

Diethyl(pyridin-3-ylmethylene)dicarbamate. To a solution of nicotinaldehyde (10.0 g 93.4 mmol, 8.77 mL, 1.00 eq) and ethyl carbamate (18.3 g, 205 mmol, 2.20 eq) in toluene (20.0 mL) was added p-toluenesulfonic acid (804 mg, 4.67 mmol, 0.05 eq). The mixture was stirred at 120° C. for 12 hrs. The reaction mixture was cooled to 0° C. The residue was filtered and washed with toluene (100 mL×3) to yield diethyl(pyridin-3-ylmethylene)dicarbamate (10.0 g, 37.4 mmol, 40.1% yield) as a white solid; $^1$H NMR (400

MHz, $CDCl_3$) δ 8.67-8.66 (m, 1H), 8.54-8.52 (m, 1H), 7.76-7.73 (m, 1H), 7.30-7.28 (m, 1H), 6.21 (s, 3H), 4.17-4.11 (m, 4H), 1.27-1.23 (m, 6H).

Ethyl 3-(pyridin-3-yl)-2-azabicyclo[2.2.2]oct-5-ene-2-carboxylate. To a solution of diethyl(pyridin-3-ylmethylene) dicarbamate (8.00 g, 29.9 mmol, 1.00 eq) in chloroform (40.0 mL) was added boron trifluoride diethyl etherate (21.2 g, 149 mmol, 18.5 mL, 5.00 eq) and cyclohexa-1,3-diene (4.80 g, 59.9 mmol, 5.70 mL, 2.00 eq). The mixture was stirred at 70° C. for 3 hrs. The reaction mixture was quenched by addition saturated solution of $NaHCO_3$ (100 mL) at 25° C., and then diluted with water (100 mL) and extracted with dichloromethane (100 mL×3). The combined organic layers were washed with water (100 mL×2) and brine (100 mL), dried over $Na_2SO_4$, filtered and concentrated under reduced pressure to give ethyl 3-(pyridin-3-yl)-2-azabicyclo[2.2.2]oct-5-ene-2-carboxylate (10.0 g, crude) as a yellow oil; m/z=259 $(M+1)^+$. 2-Methyl-3-(pyridin-3-yl)-2-azabicyclo[2.2.2]oct-5-ene. To a solution of lithium aluminum hydride (2.35 g, 61.9 mmol, 8.00 eq) in dry tetrahydrofuran (25.0 mL) at 0° C., ethyl 3-(pyridin-3-yl)-2-azabicyclo[2.2.2]oct-5-ene-2-carboxylate (2.00 g, 7.74 mmol, 1.00 eq) in tetrahydrofuran (25.0 mL) was added. The mixture was stirred at 25° C. for 10 hrs. The reaction mixture was quenched with water (2.00 mL), 15% NaOH (aq, 2.00 mL) and water (6.00 mL). Then the reaction mixture was dried over $Na_2SO_4$, filtered and the filtrate was concentrated under reduced pressure to give a residue. The residue was purified by preparative HPLC (neutral condition; column: Phenomenex Gemini 150*25 mm*10 um; mobile phase: [water (0.04% $NH_4OH$+10 mM $NH_4HCO_3$)—acetonitrile]; B %: 40%-67%, 10 min) to yield 2-methyl-3-(pyridin-3-yl)-2-azabicyclo[2.2.2]oct-5-ene (12.9 mg, 63.4 μmol, 0.819% yield, 97.9% purity) as a yellow oil; m/z=201 $(M+1)^+$; $^1H$ NMR (400 MHz, MeOD) δ 8.65 (m, 1H), 8.40 (m, 1H), 8.02-7.93 (m, 1H), 7.47-7.35 (m, 1H), 6.62-6.57 (m, 1H), 6.43-6.32 (m, 1H), 3.49-3.41 (m, 1H), 3.12-3.05 (m, 1H), 2.53-2.44 (m, 1H), 2.17 (s, 3H), 2.06-1.94 (m, 1H), 1.39-1.19 (m, 2H), 0.95-0.86 (m, 1H).

Compound 15

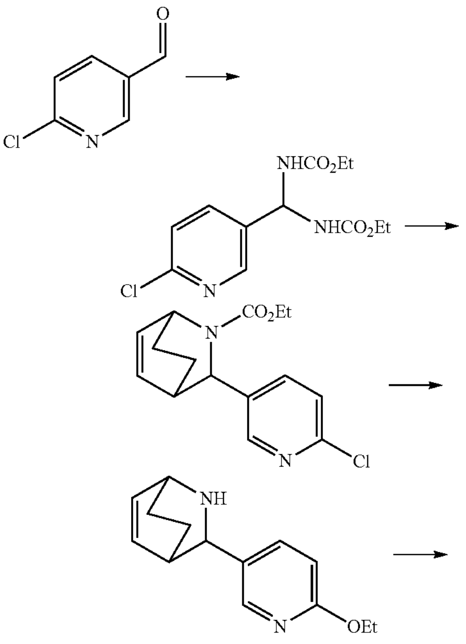

-continued

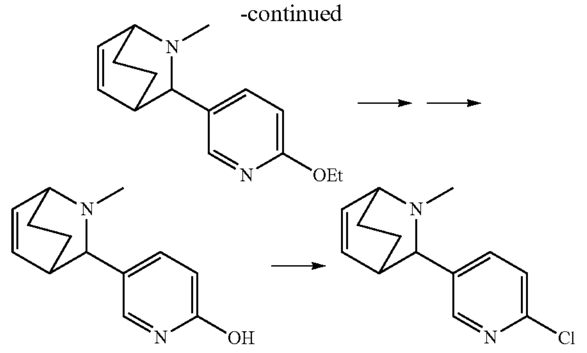

Diethyl(6-chloropyridin-3-ylmethylene)dicarbamate. To a solution of 6-chloropyridine-3-carbaldehyde (10.0 g, 70.7 mmol, 1.00 eq) and ethyl carbamate (14.0 g, 157 mmol, 2.22 eq) in toluene (50.0 mL) was added p-toluenesulfonic acid (608 mg, 3.53 mmol, 0.05 eq). The mixture was stirred at 120° C. for 24 hrs. The reaction mixture was cooled to 0° C. The residue was filtered and the solid was collected. Diethyl (6-chloropyridin-3-ylmethylene)dicarbamate (20.0 g, crude) was white solid; m/z=302 $(M+1)^+$; $^1H$ NMR (400 MHz, $CDCl_3$) δ 8.45-8.44 (m, 1H), 7.73-7.70 (m, 1H), 7.33-7.31 (m, 1H), 6.18-6.14 (m, 1H), 6.05-6.04 (m, 1H), 4.19-4.12 (m, 4H), 1.28-1.24 (m, 6H).

Ethyl 3-(6-chloropyridin-3-yl)-2-azabicyclo[2.2.2]oct-5-ene-2-carboxylate. To a solution of diethyl (6-chloropyridin-3-ylmethylene)dicarbamate (10.0 g, 33.1 mmol, 1.00 eq) in chloroform (50.0 mL) was added boron trifluoride diethyl etherate (23.5 g, 165 mmol, 20.5 mL, 5.00 eq) and cyclohexa-1,3-diene (5.31 g, 66.3 mmol, 6.31 mL, 2.00 eq). The mixture was stirred at 70° C. for 12 hrs. The reaction mixture was quenched by addition saturated solution of $NaHCO_3$ (100 ml) at 25° C., and then diluted with water (100 mL) and extracted with dichloromethane (100 mL×3). The combined organic layers were washed with brine (100 mL), dried over $Na_2SO_4$, filtered and concentrated under reduced pressure to yield ethyl 3-(6-chloropyridin-3-yl)-2-azabicyclo[2.2.2]oct-5-ene-2-carboxylate (9.00 g, crude) as a yellow oil; m/z=293 $(M+1)^+$.

3-(6-Ethoxypyridin-3-yl)-2-azabicyclo[2.2.2]oct-5-ene. To a solution of ethyl 3-(6-chloropyridin-3-yl)-2-azabicyclo [2.2.2]oct-5-ene-2-carboxylate (7.00 g, 23.9 mmol, 1.00 eq) in ethanol (60.0 mL) was added NaOH (12.0 g, 300 mmol, 12.6 eq). The reaction mixture was stirred at 90° C. for 12 hrs. The reaction mixture was concentrated under reduced pressure. Then the residue was adjusted to pH=1 (1 M HCl), then the mixture was extracted with ethyl acetate (50.0 mL×2). The combined aqueous layers were adjusted to pH=10 (NaOH), then the mixture was extracted with ethyl acetate (50.0 mL×2), dried over sodium sulfate, filtered and concentrated under reduced pressure to give a residue. 3-(6-Ethoxypyridin-3-yl)-2-azabicyclo[2.2.2]oct-5-ene (2.00 g, 8.68 mmol, 36.3% yield) was obtained as a yellow oil; m/z=231 $(M+1)^+$.

2-Methyl-3-(6-ethoxypyridin-3-yl)-2-azabicyclo[2.2.2] oct-5-ene. To a solution of 3-(6-ethoxypyridin-3-yl)-2-azabicyclo[2.2.2]oct-5-ene (2.00 g, 8.68 mmol, 1.00 eq) in formic acid (10.0 mL) was added formaldehyde (6.54 g, 80.6 mmol, 6.00 mL, 37.0% purity, 9.28 eq). The mixture was stirred at 100° C. for 2 hrs. The mixture was quenched with a 40 percent (w/v) solution of NaOH (pH=9) and extracted with dichloromethane (20.0 mL×2). The combined organic layers were dried over $Na_2SO_4$, filtered and concentrated under reduced pressure to give a residue. The crude product was purified by reversed-phase HPLC (0.10% $NH_4OH$ mobile phase). 2-Methyl-3-(6-ethoxypyridin-3-yl)-2-azabicyclo[2.2.2]oct-5-ene (500 mg, 2.05 mmol, 23.5% yield) was obtained as a yellow oil; m/z=245 $(M+1)^+$; $^1H$ NMR (400 MHz, $CDCl_3$) δ 8.16-8.13 (m, 1H), 7.74-7.68 (m, 1H), 6.74-6.68 (m, 1H), 6.59-6.53 (m, 1H), 6.32-6.26 (m, 1H), 4.26-4.21 (m, 2H), 3.41-3.39 (m, 1H), 2.39-2.34 (m, 1H), 2.13 (s, 3H), 1.99-1.90 (m, 1H), 1.36-1.28 (m, 5H), 0.93-0.81 (m, 1H).

2-Methyl-3-(6-hydroxypyridin-3-yl)-2-azabicyclo[2.2.2]oct-5-ene. Solution of 2-methyl-3-(6-ethoxypyridin-3-yl)-2-azabicyclo[2.2.2]oct-5-ene 8 (260 mg, 1.06 mmol, 1.00 eq) in hydrochloric acid (3 M, 5.00 mL, 14.1 eq) was stirred at 100° C. for 12 hrs. The reaction mixture was concentrated under reduced pressure to give a residue. The crude product was purified by reversed-phase HPLC (0.10% HCl condition). 2-Methyl-3-(6-hydroxypyridin-3-yl)-2-azabicyclo[2.2.2]oct-5-ene (100 mg, 462 μmol, 43.5% yield) was obtained as a yellow oil; m/z=217 $(M+1)^+$.

2-Methyl-3-(6-chloroxypyridin-3-yl)-2-azabicyclo[2.2.2]oct-5-ene. Solution of 2-methyl-3-(6-hydroxypyridin-3-yl)-2-azabicyclo[2.2.2]oct-5-ene 9 (100 mg, 462 umol, 1.00 eq) in $POCl_3$ (8.27 g, 53.9 mmol, 5.01 mL, 116 eq) was stirred at 70° C. for 12 hrs. The reaction mixture was poured into the water (10.0 mL), then the mixture was adjusted to pH=10 and extracted with dichloromethane (20.0 mL×2). The combined organic layers were dried over sodium sulfate, filtered and concentrated under reduced pressure to give a residue. The residue was purified by preparative HPLC (basic condition; column: Waters Xbridge 150*25 5 u; mobile phase: [water (0.05% ammonia hydroxide v/v)—ACN]; B %: 48%-78%, 10 min). 2-Methyl-3-(6-chloroxypyridin-3-yl)-2-azabicyclo[2.2.2]oct-5-ene (17.6 mg, 73.7 umol, 15.9% yield, 98.2% purity) was obtained as a yellow solid; m/z=235 $(M+1)^+$; $^1H$ NMR (400 MHz, $CDCl_3$) δ 8.46-8.53 (m, 1H), 7.83-7.79 (m, 1H), 7.31-7.27 (m, 1H), 6.59-6.53 (m, 1H), 6.37-6.32 (m, 1H), 3.44-3.38 (m, 1H), 3.02-2.98 (m, 1H), 2.46-2.41 (m, 1H), 2.16 (s, 3H), 2.01-1.92 (m, 1H), 1.36-1.21 (m, 2H), 0.96-0.86 (m, 2H).

Compound 16

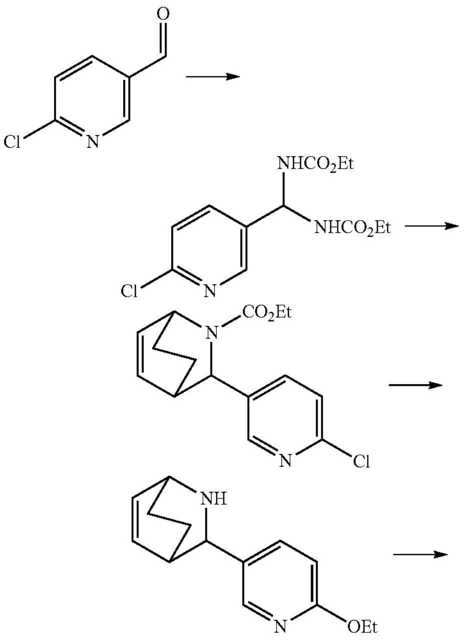

-continued

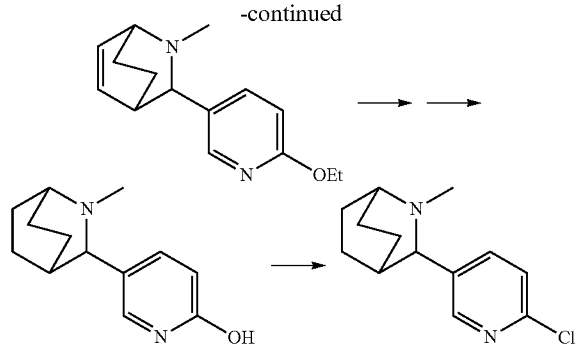

Diethyl (6-chloropyridin-3-ylmethylene)dicarbamate. To a solution of 6-chloropyridine-3-carbaldehyde (10.0 g, 70.7 mmol, 1.00 eq) and ethyl carbamate (14.0 g, 157 mmol, 2.22 eq) in toluene (50.0 mL) was added p-toluenesulfonic acid (608 mg, 3.53 mmol, 0.05 eq). The mixture was stirred at 120° C. for 24 hrs. The reaction mixture was cooled to 0° C. The residue was filtered and the solid was collected. Diethyl (6-chloropyridin-3-ylmethylene)dicarbamate (20.0 g, crude) was white solid; m/z=302 $(M+1)^+$; $^1H$ NMR (400 MHz, $CDCl_3$) δ 8.45-8.44 (m, 1H), 7.73-7.70 (m, 1H), 7.33-7.31 (m, 1H), 6.18-6.14 (m, 1H), 6.05-6.04 (m, 1H), 4.19-4.12 (m, 4H), 1.28-1.24 (m, 6H).

Ethyl 3-(6-chloropyridin-3-yl)-2-azabicyclo[2.2.2]oct-5-ene-2-carboxylate. To a solution of diethyl (6-chloropyridin-3-ylmethylene)dicarbamate (10.0 g, 33.1 mmol, 1.00 eq) in chloroform (50.0 mL) was added boron trifluoride diethyl etherate (23.5 g, 165 mmol, 20.5 mL, 5.00 eq) and cyclohexa-1,3-diene (5.31 g, 66.3 mmol, 6.31 mL, 2.00 eq). The mixture was stirred at 70° C. for 12 hrs. The reaction mixture was quenched by addition saturated solution of $NaHCO_3$ (100 ml) at 25° C., and then diluted with water (100 mL) and extracted with dichloromethane (100 mL×3). The combined organic layers were washed with brine (100 mL), dried over $Na_2SO_4$, filtered and concentrated under reduced pressure to yield ethyl 3-(6-chloropyridin-3-yl)-2-azabicyclo[2.2.2]oct-5-ene-2-carboxylate (9.00 g, crude) as a yellow oil; m/z=293 $(M+1)^+$.

3-(6-Ethoxypyridin-3-yl)-2-azabicyclo[2.2.2]oct-5-ene. To a solution of ethyl 3-(6-chloropyridin-3-yl)-2-azabicyclo[2.2.2]oct-5-ene-2-carboxylate (7.00 g, 23.9 mmol, 1.00 eq) in ethanol (60.0 mL) was added NaOH (12.0 g, 300 mmol, 12.6 eq). The reaction mixture was stirred at 90° C. for 12 hrs. The reaction mixture was concentrated under reduced pressure.

Then the residue was adjusted to pH=1 (1 M HCl), then the mixture was extracted with ethyl acetate (50.0 mL×2). The combined aqueous layers were adjusted to pH=10 (NaOH), then the mixture was extracted with ethyl acetate (50.0 mL×2), dried over sodium sulfate, filtered and concentrated under reduced pressure to give a residue. 3-(6-Ethoxypyridin-3-yl)-2-azabicyclo[2.2.2]oct-5-ene (2.00 g, 8.68 mmol, 36.3% yield) was obtained as a yellow oil; m/z=231 $(M+1)^+$.

2-Methyl-3-(6-ethoxypyridin-3-yl)-2-azabicyclo[2.2.2]oct-5-ene. To a solution of 3-(6-ethoxypyridin-3-yl)-2-azabicyclo[2.2.2]oct-5-ene (2.00 g, 8.68 mmol, 1.00 eq) in formic acid (10.0 mL) was added formaldehyde (6.54 g, 80.6 mmol, 6.00 mL, 37.0% purity, 9.28 eq). The mixture was stirred at 100° C. for 2 hrs. The mixture was quenched with a 40 percent (w/v) solution of NaOH (pH=9) and extracted with dichloromethane (20.0 mL×2). The combined organic layers were dried over $Na_2SO_4$, filtered and concentrated under reduced pressure to give a residue. The crude product was purified by reversed-phase HPLC (0.10% $NH_4OH$ mobile phase). 2-Methyl-3-(6-ethoxypyridin-3-yl)-2-azabicyclo[2.2.2]oct-5-ene (500 mg, 2.05 mmol, 23.5% yield) was obtained as a yellow oil; m/z=245 $(M+1)^+$; $^1H$ NMR (400 MHz, $CDCl_3$) δ 8.16-8.13 (m, 1H), 7.74-7.68 (m, 1H), 6.74-6.68 (m, 1H), 6.59-6.53 (m, 1H), 6.32-6.26 (m, 1H), 4.26-4.21 (m, 2H), 3.41-3.39 (m, 1H), 2.39-2.34 (m, 1H), 2.13 (s, 3H), 1.99-1.90 (m, 1H), 1.36-1.28 (m, 5H), 0.93-0.81 (m, 1H).

3-(6-Ethoxy-3-pyridyl)-2-methyl-2-azabicyclo[2.2.2]octane. To a solution of 2-methyl-3-(6-ethoxypyridin-3-yl)-2-azabicyclo[2.2.2]oct-5-ene (250 mg, 1.02 mmol, 1.00 eq) in ethanol (5.00 mL) was added Pd/C (100 mg, 1.02 mmol, 10.0%, 1.00 eq) under $N_2$. The suspension was degassed under vacuum and purged with $H_2$ several times. The mixture was stirred under $H_2$ (15 psi) at 25° C. for 10 hrs. The mixture was filtered and concentrated under reduced pressure to give a residue. 3-(6-Ethoxy-3-pyridyl)-2-methyl-2-azabicyclo[2.2.2]octane (150 mg, 608 umol, 59.5% yield) was obtained as colorless oil; m/z=247 $(M+1)^+$.

3-(6-Hydroxy-3-pyridyl)-2-methyl-2-azabicyclo[2.2.2]octane. Solution of 3-(6-ethoxy-3-pyridyl)-2-methyl-2-azabicyclo[2.2.2]octane (250 mg, 1.01 mmol, 1.00 eq) in hydrochloric acid (3 M, 25.0 mL, 73.9 eq) was stirred at 100° C. for 24 hrs. The reaction mixture was concentrated under reduced pressure to give a residue. The crude product was purified by reversed-phase HPLC (0.10% HCl condition). 3-(6-Hydroxy-3-pyridyl)-2-methyl-2-azabicyclo[2.2.2]octane hydrochloride (230 mg, 902 umol, 88.9% yield) was obtained as a white solid; m/z=219 $(M+1)^+$.

3-(6-Chloro-3-pyridyl)-2-methyl-2-azabicyclo[2.2.2]octane. Solution of 3-(6-hydroxy-3-pyridyl)-2-methyl-2-azabicyclo[2.2.2]octane hydrochloride (230 mg, 1.05 mmol, 1.00 eq) in $POCl_3$ (8.10 g, 52.8 mmol, 4.91 mL, 50.1 eq) was stirred at 70° C. for 12 hrs. The reaction mixture was poured into the water (10.0 mL), then pH of the solution was adjusted to 10 ($NaHCO_3$, aq) and extracted with dichloromethane (20.0 mL×2). The combined organic layers were dried over sodium sulfate, filtered and concentrated under reduced pressure to give a residue. The residue was purified by preparative HPLC (basic condition; column: Xtimate C18 150*25 mm*5 um; mobile phase: [water (0.05% ammonium hydroxide v/v)—acetonitrile]; B %: 60%-90%, 10 min) to 3-(6-chloro-3-pyridyl)-2-methyl-2-azabicyclo[2.2.2]octane (87.9 mg, 369 umol, 35.1% yield, 99.4% purity) was obtained as an off-white solid; m/z=237 $(M+1)^+$; $^1H$ NMR (400 MHz, $CDCl_3$) δ 8.41-8.38 (m, 1H), 7.54-7.51 (m, 1H), 7.26-7.23 (m, 1H), 3.38-3.35 (m, 1H), 2.63-2.59 (m, 1H), 2.44 (s, 3H), 2.09-1.99 (m, 1H), 1.94-1.75 (m, 2H), 1.69-1.61 (m, 1H), 1.56-1.31 (m, 4H), 1.24-1.19 (m, 1H).

Compound 17

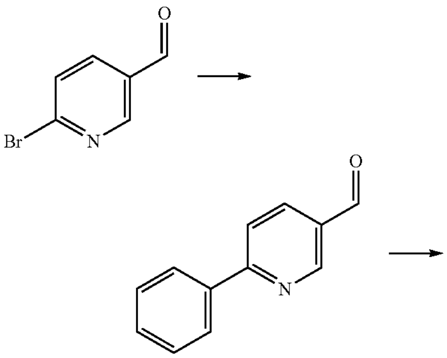

-continued

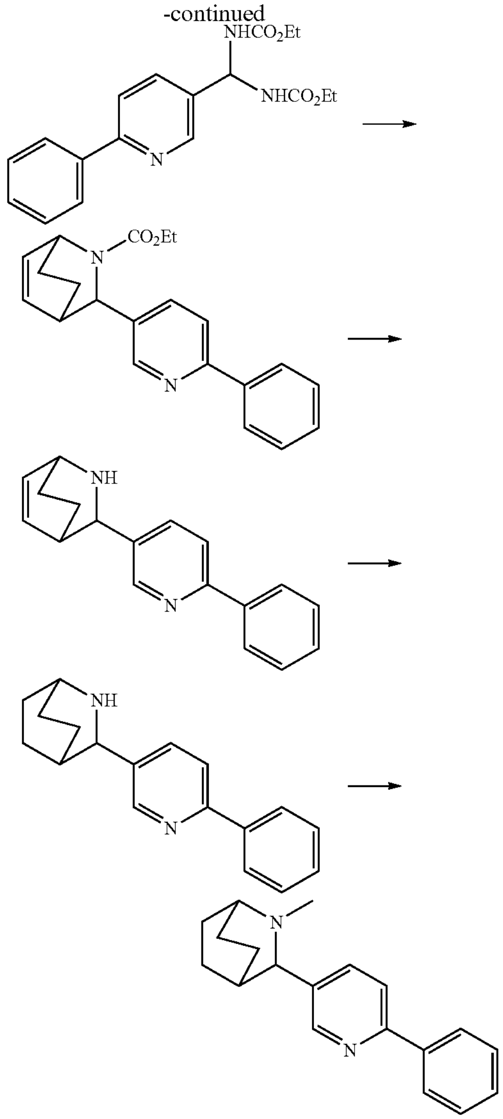

6-Phenylpyridine-3-carbaldehyde. To a solution of 6-bromopyridine-3-carbaldehyde (24.5 g, 132 mmol, 1.00 eq), phenylboronic acid (24.1 g, 198 mmol, 1.50 eq) in toluene (70.0 mL) and ethanol (70.0 mL) was added solution of $Na_2CO_3$ (2 M, 35.0 mL, 5.31e-1.00 eq), then $Pd(PPh_3)_4$ (15.2 g, 13.1 mmol, 0.10 eq) was added under $N_2$. The mixture was stirred at 80° C. for 3 hrs. The reaction mixture was quenched by addition of water (200 mL), and extracted with ethyl acetate (150 mL×3). The combined organic layers were washed with aqueous NaCl (100 mL×2), dried over $Na_2SO_4$, filtered and concentrated under reduced pressure to give a residue. The residue was purified by column chromatography (SiO2, Petroleum ether/Ethyl acetate=1:0 to 5:1). TLC (Petroleum ether/Ethyl acetate=5/1, Rf of P1 was 0.50). 6-Phenylpyridine-3-carbaldehyde (18.0 g, 94.4 mmol, 71.7% yield, 96.1% purity) was obtained as a light yellow solid; m/z=184 $(M+1)^+$.

Diethyl (6-phenylpyridin-3-ylmethylene)dicarbamate. To a solution of 6-phenylpyridine-3-carbaldehyde (18.0 g, 98.3 mmol, 1.00 eq) in toluene (200 mL) was added p-toluenesulfonic acid (845 mg, 4.91 mmol, 0.05 eq) and ethyl carbamate (21.9 g, 245 mmol, 2.50 eq). The mixture was stirred at 120° C. for 12 hrs. The reaction mixture was cooled to 0° C. and filtered. The crude product was triturated with toluene (50.0 mL) at 25° C. for 30 min. Diethyl (6-phenylpyridin-3-ylmethylene)dicarbamate (25.0 g, 72.8 mmol, 74.1% yield) was obtained as a white solid; $^1$H NMR (400 MHz, $CDCl_3$) δ 8.81-8.74 (m, 1H), 8.03-7.93 (m, 2H), 7.86-7.78 (m, 1H), 7.71-7.62 (m, 1H), 7.52-7.38 (m, 3H), 6.32-6.16 (m, 1H), 6.11-5.76 (m, 2H), 4.22-4.09 (m, 4H), 1.35-1.20 (m, 6H).

3-(6-Phenylpyridin-3-yl)-2-azabicyclo[2.2.2]oct-5-ene-2-carboxylate. To a solution of diethyl (6-phenylpyridin-3-ylmethylene)dicarbamate (5.00 g, 14.5 mmol, 1.00 eq) in chloroform (50.0 mL) was added cyclohexa-1,3-diene (2.33 g, 29.1 mmol, 2.77 mL, 2.00 eq) and trifluoride diethyl etherate (10.3 g, 72.8 mmol, 8.99 mL, 5.00 eq). The mixture was stirred at 70° C. for 10 hrs. The mixture was quenched with saturated solution of $NaHCO_3$ (100 mL) and extracted with dichloromethane (50.0 mL×2). The combined organic layers were dried over anhydrous sodium sulfate, filtered and concentrated to get the residue. 3-(6-Phenylpyridin-3-yl)-2-azabicyclo[2.2.2]oct-5-ene-2-carboxylate (4.00 g, crude) was obtained as a yellow oil; m/z=335 $(M+1)^+$.

3-(6-Phenylpyridin-3-yl)-2-azabicyclo[2.2.2]oct-5-ene. 3-(6-Phenylpyridin-3-yl)-2-azabicyclo[2.2.2]oct-5-ene-2-carboxylate (1.00 g, 2.99 mmol, 1.00 eq) was dissolved in a 20 percent (w/v) solution of NaOH (10.0 g, 250 mmol, 83.6 eq) in absolute ethanol (50.0 mL) and the mixture was stirred at 100° C. for 12 hrs. The reaction mixture was concentrated under reduced pressure. Then the residue was washed with water (50.0 mL) and extracted with ethyl acetate (50.0 mL×2). The combined organic layers were adjusted to pH=2 (1 M HCl), then the mixture was extracted with ethyl acetate (50.0 mL×2). The combined aqueous layers were adjusted to pH=10 ($NaHCO_3$), then the mixture was extracted with ethyl acetate (50.0 mL×2), dried over sodium sulfate, filtered and concentrated under reduced pressure to give a residue. The residue was purified by preparative HPLC (neutral condition; column: Waters Xbridge 150*25 5 u; mobile phase: [water (10 mM $NH_4HCO_3$)—ACN]; B %: 35%-65%, 10 min) to yield 3-(6-phenylpyridin-3-yl)-2-azabicyclo[2.2.2]oct-5-ene (51.4 mg, 191 umol, 6.41% yield, 97.8% purity) as an off-white solid; m/z=263 $(M+1)^+$; $^1$H NMR (400 MHz, $CDCl_3$) δ 8.81-8.76 (m, 1H), 8.05-7.95 (m, 3H), 7.76-7.69 (m, 1H), 7.51-7.48 (m, 3H), 6.64-6.57 (m, 1H), 6.51-6.44 (m, 1H), 3.97-3.87 (m, 1H), 3.74-3.64 (m, 1H), 2.66-2.55 (m, 1H), 2.07-1.93 (m, 1H), 1.44-1.24 (m, 3H), 1.04-0.93 (m, 1H).

3-(6-Phenyl-3-pyridyl)-2-azabicyclo[2.2.2]octane. To a solution of 3-(6-phenylpyridin-3-yl)-2-azabicyclo[2.2.2]oct-5-ene (300 mg, 1.14 mmol, 1.00 eq) in ethanol (10.0 mL) was added Pd/C (100 mg, 1.14 mmol, 10.0%, 1.00 eq) under $N_2$. The suspension was degassed under vacuum and purged with $H_2$ several times. The mixture was stirred under $H_2$ (15 psi) at 25° C. for 10 hrs. The mixture was filtered and then the filtrate was concentrated under reduced pressure to give a residue. The residue was purified by preparative HPLC (basic condition, column: Xtimate C18 150*25 mm*5 um; mobile phase: [water (0.05% ammonium hydroxide v/v)—acetonitrile]; B %: 47%-77%). 3-(6-Phenyl-3-pyridyl)-2-azabicyclo[2.2.2]octane (250 mg, 945 μmol, 82.7% yield, 100% purity) was obtained as an off-white solid; m/z=265 $(M+1)^+$; 1H NMR (400 MHz, $CDCl_3$) δ 8.76-8.71 (m, 1H), 8.04-7.47 (m, 3H), 7.76-7.63 (m, 1H), 7.51-7.39 (m, 3H), 4.41-4.32 (m, 1H), 3.07-2.96 (m, 1H), 2.07-1.72 (m, 7H), 1.54-1.23 (m, 3H).

2-Methyl-3-(6-phenyl-3-pyridyl)-2-azabicyclo[2.2.2]octane. To a solution of 3-(6-phenyl-3-pyridyl)-2-azabicyclo[2.2.2]octane (170 mg, 643 μmol, 1.00 eq) in formic acid (5.00 mL) was added formaldehyde (545 mg, 6.72 mmol, 0.50 mL, 37.0% purity, 10.4 eq). The mixture was stirred at 100° C. for 10 hrs. The mixture was quenched with a 40 percent (w/v) solution of NaOH (pH=9) and extracted with dichloromethane (20.0 mL×2). The combined organic layers were dried over $Na_2SO_4$, filtered and concentrated under reduced pressure to give a residue. The residue was purified by preparative HPLC (HCl condition, column: Phenomenex Synergi C18 150*25*10 um; mobile phase: [water (0.05% HCl)—acetonitrile]; B %: 8%-28%, 9 min). 2-Methyl-3-(6-phenyl-3-pyridyl)-2-azabicyclo[2.2.2]octane (87.5 mg, 276 μmol, 42.9% yield, 99.3% purity, HCl) was obtained as an off-white solid; m/z=279 $(M+1)^+$; 1H NMR (400 MHz, MeOD) δ 9.26-9.18 (m, 1H), 9.03-8.92 (m, 1H), 8.54-8.49 (m, 1H), 8.06-7.97 (m, 2H), 7.79-7.66 (m, 3H), 3.66-3.62 (m, 1H), 3.04 (s, 3H), 2.66-2.52 (m, 1H), 2.46-2.34 (m, 1H), 2.24-1.81 (m, 8H).

Compound 18

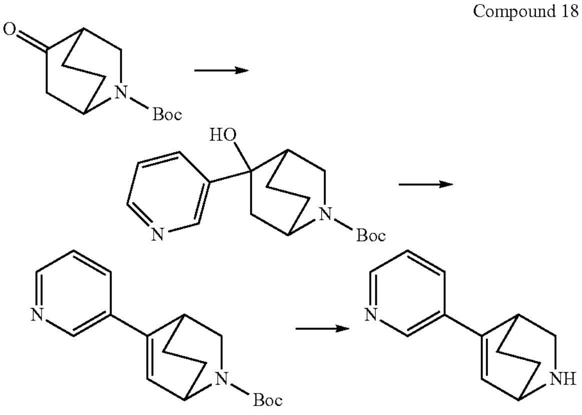

tert-Butyl 5-hydroxy-5-(3-pyridyl)-2-azabicyclo[2.2.2]octane-2-carboxylate. To a solution of 3-iodopyridine (682 mg, 3.33 mmol, 1.50 eq) in tetrahydrofuran (5 mL) was added n-BuLi (2.50 M, 1.33 mL, 1.50 eq) at −78° C. The mixture was stirred at −78° C. for 0.5 hr. Then tert-butyl 5-oxo-2-azabicyclo[2.2.2]octane-2-carboxylate (0.500 g, 2.22 mmol, 1.00 eq) in tetrahydrofuran (5 mL) was added. The mixture was stirred at −78° C. for 2 hrs. The reaction mixture was quenched by addition of saturated aqueous solution of $NH_4Cl$ (3 mL) at −78° C., and concentrated under reduced pressure to give a residue. The residue was purified by column chromatography (SiO2, Petroleum ether/Ethyl acetate=10/1 to 1/1). tert-Butyl 5-hydroxy-5-(3-pyridyl)-2-azabicyclo[2.2.2]octane-2-carboxylate (0.224 g, 736 umol, 33.2% yield) was obtained as an yellow oil; m/z=305 $(M+1)^+$.

tert-Butyl 5-(3-pyridyl)-2-azabicyclo[2.2.2]oct-5-ene-2-carboxylate. To a solution of tert-butyl 5-hydroxy-5-(3-pyridyl)-2-azabicyclo[2.2.2]octane-2-carboxylate (224 mg, 736 umol, 1.00 eq) in dichloromethane (10 mL) was added triethylamine (744 mg, 7.36 mmol, 1.02 mL, 10.0 eq) and methanesulfonyl chloride (421 mg, 3.68 mmol, 284 μL, 5.00 eq) at 0° C. The mixture was stirred at 25° C. for 2 hrs. The reaction mixture was quenched by addition water 2 mL at 0° C. and then concentrated under reduced pressure to give a residue. The crude product was purified by reversed-phase HPLC (0.1% $NH_4OH$). tert-Butyl 5-(3-pyridyl)-2-azabicyclo[2.2.2]oct-5-ene-2-carboxylate (0.150 g, 523 umol, 71.2% yield) was obtained as an yellow oil; m/z=287 $(M+1)^+$.

5-(3-Pyridyl)-2-azabicyclo[2.2.2]oct-5-ene. To a solution of tert-butyl 5-(3-pyridyl)-2-azabicyclo[2.2.2]oct-5-ene-2-carboxylate (0.150 g, 523 umol, 1.00 eq) in dioxane (5 mL) was added HCl/dioxane (4 M, 131 uL, 1 eq). The mixture was stirred at 25° C. for 0.5 hr. The reaction mixture was concentrated under reduced pressure to give a residue. The residue was purified by prep-TLC (SiO2, DCM/MeOH=10/1). TLC (Dichloromethane/Methanol= 10/1) showed one major spot (Rf=0.35) was detected. 5-(3-Pyridyl)-2-azabicyclo[2.2.2]oct-5-ene (11.7 mg, 62.6 umol, 11.9% yield, 99.7% purity) was obtained as an yellow solid; m/z=205 $(M+19)^+$; $^1H$ NMR (400 MHz, MeOD) δ 8.72 (s, 1H), 8.48 (m, 1H), 8.00 (m, 1H), 7.46 (m, 1H), 6.85 (m, 1H), 4.15 (m, 1H), 3.41 (s, 1H), 3.22-3.18 (m, 1H), 2.80-2.70 (m, 1H), 2.19-2.13 (m, 1H), 1.94-1.89 (m, 1H), 1.60-1.49 (m, 2H).

Compound 19

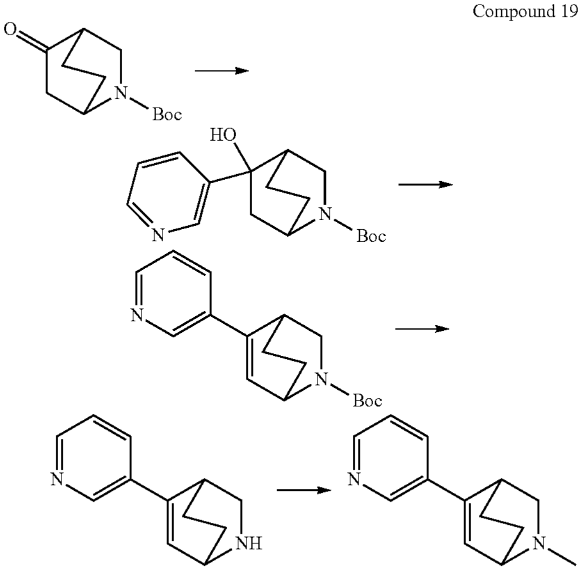

tert-Butyl 5-hydroxy-5-(3-pyridyl)-2-azabicyclo[2.2.2]octane-2-carboxylate. To a solution of 3-iodopyridine (682 mg, 3.33 mmol, 1.50 eq) in tetrahydrofuran (5 mL) was added n-BuLi (2.50 M, 1.33 mL, 1.50 eq) at −78° C. The mixture was stirred at −78° C. for 0.5 hr. Then tert-butyl 5-oxo-2-azabicyclo[2.2.2]octane-2-carboxylate (0.500 g, 2.22 mmol, 1.00 eq) in tetrahydrofuran (5 mL) was added. The mixture was stirred at −78° C. for 2 hrs. The reaction mixture was quenched by addition of saturated aqueous solution of $NH_4Cl$ (3 mL) at −78° C., and concentrated under reduced pressure to give a residue. The residue was purified by column chromatography (SiO2, Petroleum ether/Ethyl acetate=10/1 to 1/1). tert-Butyl 5-hydroxy-5-(3-pyridyl)-2-azabicyclo[2.2.2]octane-2-carboxylate (0.224 g, 736 umol, 33.2% yield) was obtained as an yellow oil; m/z=305 $(M+1)^+$.

tert-Butyl 5-(3-pyridyl)-2-azabicyclo[2.2.2]oct-5-ene-2-carboxylate. To a solution of tert-butyl 5-hydroxy-5-(3-pyridyl)-2-azabicyclo[2.2.2]octane-2-carboxylate (224 mg, 736 umol, 1.00 eq) in dichloromethane (10 mL) was added triethylamine (744 mg, 7.36 mmol, 1.02 mL, 10.0 eq) and methanesulfonyl chloride (421 mg, 3.68 mmol, 284 μL, 5.00 eq) at 0° C. The mixture was stirred at 25° C. for 2 hrs. The reaction mixture was quenched by addition water 2 mL at 0° C. and then concentrated under reduced pressure to give a residue. The crude product was purified by reversed-phase HPLC (0.1% $NH_4OH$). tert-Butyl 5-(3-pyridyl)-2-azabicyclo[2.2.2]oct-5-ene-2-carboxylate (0.150 g, 523 umol, 71.2% yield) was obtained as an yellow oil; m/z=287 $(M+1)^+$.

5-(3-Pyridyl)-2-azabicyclo[2.2.2]oct-5-ene. To a solution of tert-butyl 5-(3-pyridyl)-2-azabicyclo[2.2.2]oct-5-ene-2-carboxylate (0.150 g, 523 umol, 1.00 eq) in dioxane (5 mL) was added HCl/dioxane (4 M, 131 uL, 1 eq). The mixture was stirred at 25° C. for 0.5 hr. The reaction mixture was concentrated under reduced pressure to give a residue. The residue was purified by prep-TLC (SiO2, DCM/MeOH=10/1). TLC (Dichloromethane/Methanol= 10/1) showed one major spot (Rf=0.35) was detected. 5-(3-Pyridyl)-2-azabicyclo[2.2.2]oct-5-ene (11.7 mg, 62.6 umol, 11.9% yield, 99.7% purity) was obtained as an yellow solid; m/z=205 $(M+19)^+$; $^1H$ NMR (400 MHz, MeOD) δ 8.72 (s, 1H), 8.48 (m, 1H), 8.00 (m, 1H), 7.46 (m, 1H), 6.85 (m, 1H), 4.15 (m, 1H), 3.41 (s, 1H), 3.22-3.18 (m, 1H), 2.80-2.70 (m, 1H), 2.19-2.13 (m, 1H), 1.94-1.89 (m, 1H), 1.60-1.49 (m, 2H).

2-Methyl-5-(3-pyridyl)-2-azabicyclo[2.2.2]ocit-5-ene. To a solution of 5-(3-pyridyl)-2-azabicyclo[2.2.2]oct-5-ene in formic acid (5 mL) was added formaldehyde (545 mg, 6.72 mmol, 0.5 mL, 37.0% purity, 17.8 eq). The mixture was stirred at 100° C. for 2 hrs. The mixture was quenched with a 40 percent (w/v) solution of NaOH (pH=9) and extracted with dichloromethane (20 mL×2). The combined organic layers were dried over $Na_2SO_4$, filtered and concentrated under reduced pressure to give a residue. The residue was purified by prep-TLC (SiO2, DCM/MeOH=10/1). TLC (DCM/MeOH=10/1) showed one major spot (Rf=0.25) was detected. 2-Methyl-5-(3-pyridyl)-2-azabicyclo[2.2.2]oct-5-ene (24.0 mg, 118 μmol, 31.5% yield, 98.7% purity) was obtained as a brown gum; m/z=201 $(M+1)^+$; $^1H$ NMR (400 MHz, $CDCl_3$) δ 8.73 (m, 1H), 8.57 (m, 1H), 7.78-7.73 (m, 1H), 7.35-7.32 (m, 1H), 6.73-6.67 (m, 1H), 4.28 (m, 1H), 4.07-3.99 (m, 1H), 3.67 (m, 1H), 3.31 (m, 1H), 2.58 (s, 3H), 2.36-2.32 (m, 1H), 1.95-1.91 (m, 1H), 1.54-1.42 (m, 2H).

Compound 20

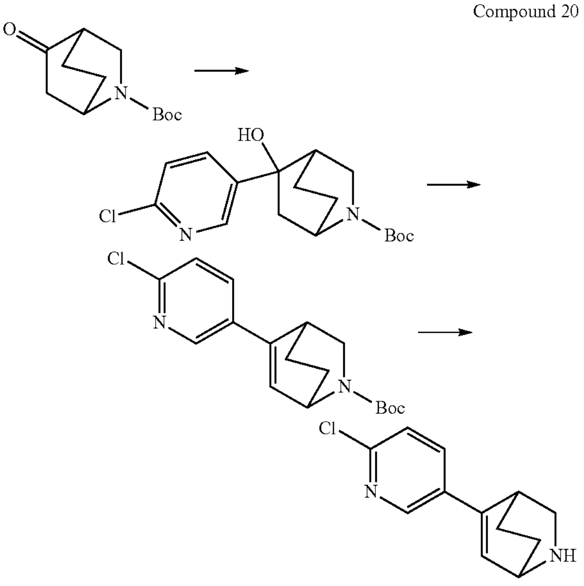

tert-Butyl 5-hydroxy-5-(2-chloro-5-pyridyl)-2-azabicyclo[2.2.2]octane-2-carboxylate. To the solution of 2-chloro-5-iodopyridine (1.28 g, 5.33 mmol, 1.20 eq) in tetrahydrofuran (15.0 mL) was added n-BuLi (2.50 M, 2.2 mL, 1.24 eq) drop-wise at −60° C. The mixture was stirred at −60° C. for 0.5 hr. Then the solution of tert-butyl 5-oxo-2-azabicyclo[2.2.2]octane-2-carboxylate (1.00 g, 4.44 mmol, 1.00 eq) in tetrahydrofuran (15.0 mL) was added drop-wise. The resulting mixture was stirred at −60° C. for 1.5 hr. The reaction mixture was quenched by saturated solution of $NH_4Cl$ (30 mL), diluted with water (50 mL) and extracted with ethyl acetate (30 mL×3). The combined organic phases were washed with brine (60 mL), dried over $Na_2SO_4$, filtered and concentrated under vacuum. The residue was purified by column chromatography ($SiO_2$, Petroleum ether/Ethyl acetate=5:1 to 2:1) to obtain tert-butyl 5-hydroxy-5-(2-chloro-5-pyridyl)-2-azabicyclo[2.2.2]octane-2-carboxylate (750 mg, 2.05 mmol, 46.3% yield, 92.8% purity) as a yellow oil; m/z=339.1 $(M+H)^+$; $^1H$ NMR (400 MHz, $CDCl_3$) δ 8.57-8.46 (m, 1H), 7.88-7.67 (m, 1H), 7.37-7.29 (m, 1H), 4.37-4.17 (m, 1H), 3.31-3.11 (m, 1H), 3.01-2.92 (m, 1H), 2.79-2.61 (m, 1H), 2.50-2.30 (m, 2H), 2.27-2.20 (m, 1H), 2.18-2.06 (m, 1H), 1.92-1.82 (m, 2H), 1.63-1.57 (m, 1H).

tert-Butyl 5-(2-chloro-5-pyridyl)-2-azabicyclo[2.2.2]oct-5-ene-2-carboxylate. To the solution of tert-butyl 5-hydroxy-5-(2-chloro-5-pyridyl)-2-azabicyclo[2.2.2]octane-2-carboxylate (500 mg, 1.48 mmol, 1.00 eq) and triethylamine (900 mg, 8.89 mmol, 1.24 mL, 6.03 eq) in dichloromethane (10.0 mL) was added methanesulfonyl chloride (845 mg, 7.38 mmol, 570 μL, 5.00 eq) at 0° C. Then the mixture was stirred at 30° C. for 2 hr. The reaction mixture was diluted with water (30 mL), extracted with dichloromethane (15 mL×2). The combined organic phases were washed with brine (30 mL), dried over $Na_2SO_4$, filtered and concentrated under vacuum. The residue was purified by column chromatography (SiO2, Petroleum ether/Ethyl acetate=10/1 to 5/1), the spot (Rf=0.8) to obtain tert-butyl 5-(2-chloro-5-pyridyl)-2-azabicyclo[2.2.2]oct-5-ene-2-carboxylate (363 mg, 1.06 mmol, 71.6% yield, 93.4% purity) as a colorless oil; m/z=321.1 $(M+H)^+$.

5-(2-chloro-5-pyridyl)-2-azabicyclo[2.2.2]oct-5-ene-2. To the solution of tert-butyl 5-(2-chloro-5-pyridyl)-2-azabicyclo[2.2.2]oct-5-ene-2-carboxylate (363 mg, 1.13 mmol, 1.00 eq) in ethyl acetate (8.00 mL) was added HCl/ethyl acetate (4.00 M, 6.13 mL, 21.7 eq). Then the mixture was stirred at 30° C. for 1 hr. The reaction mixture was concentrated under vacuum to yield 5-(2-chloro-5-pyridyl)-2-azabicyclo[2.2.2]oct-5-ene-2 hydrochloride (310 mg, crude) as a light yellow oil; m/z=192.1 $(M-28)^+$; $^1H$ NMR (400 MHz, METHANOL-d4) δ 8.57 (d, J=2.4 Hz, 1H), 8.60-8.54 (m, 1H), 8.04-7.98 (m, 1H), 7.53-7.48 (m, 1H), 6.83 (dd, J=2.0, 6.0 Hz, 1H), 4.50-4.39 (m, 1H), 3.53 (br d, J=2.4 Hz, 1H), 3.34 (s, 1H), 2.91 (br d, J=11.6 Hz, 1H), 2.24-2.14 (m, 1H), 2.01-1.91 (m, 1H), 1.70-1.53 (m, 2H).

Compound 21

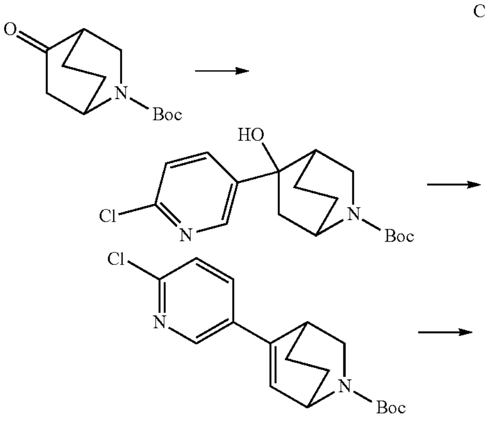

-continued

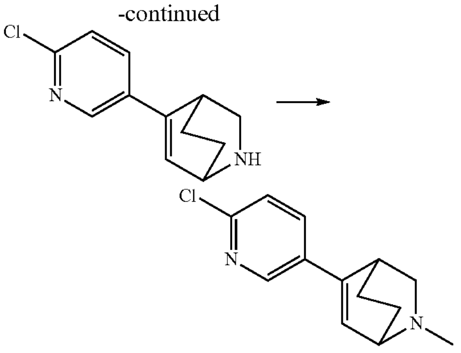

tert-Butyl 5-hydroxy-5-(2-chloro-5-pyridyl)-2-azabicyclo[2.2.2]octane-2-carboxylate. To the solution of 2-chloro-5-iodopyridine (1.28 g, 5.33 mmol, 1.20 eq) in tetrahydrofuran (15.0 mL) was added n-BuLi (2.50 M, 2.2 mL, 1.24 eq) drop-wise at −60° C. The mixture was stirred at −60° C. for 0.5 hr. Then the solution of tert-butyl 5-oxo-2-azabicyclo[2.2.2]octane-2-carboxylate (1.00 g, 4.44 mmol, 1.00 eq) in tetrahydrofuran (15.0 mL) was added drop-wise. The resulting mixture was stirred at −60° C. for 1.5 hr. The reaction mixture was quenched by saturated solution of $NH_4Cl$ (30 mL), diluted with water (50 mL) and extracted with ethyl acetate (30 mL×3). The combined organic phases were washed with brine (60 mL), dried over $Na_2SO_4$, filtered and concentrated under vacuum. The residue was purified by column chromatography ($SiO_2$, Petroleum ether/Ethyl acetate=5:1 to 2:1) to obtain tert-butyl 5-hydroxy-5-(2-chloro-5-pyridyl)-2-azabicyclo[2.2.2]octane-2-carboxylate (750 mg, 2.05 mmol, 46.3% yield, 92.8% purity) as a yellow oil; m/z=339.1 $(M+H)^+$; $^1H$ NMR (400 MHz, $CDCl_3$) δ 8.57-8.46 (m, 1H), 7.88-7.67 (m, 1H), 7.37-7.29 (m, 1H), 4.37-4.17 (m, 1H), 3.31-3.11 (m, 1H), 3.01-2.92 (m, 1H), 2.79-2.61 (m, 1H), 2.50-2.30 (m, 2H), 2.27-2.20 (m, 1H), 2.18-2.06 (m, 1H), 1.92-1.82 (m, 2H), 1.63-1.57 (m, 1H).

tert-Butyl 5-(2-chloro-5-pyridyl)-2-azabicyclo[2.2.2]oct-5-ene-2-carboxylate. To the solution of tert-butyl 5-hydroxy-5-(2-chloro-5-pyridyl)-2-azabicyclo[2.2.2]octane-2-carboxylate (500 mg, 1.48 mmol, 1.00 eq) and triethylamine (900 mg, 8.89 mmol, 1.24 mL, 6.03 eq) in dichloromethane (10.0 mL) was added methanesulfonyl chloride (845 mg, 7.38 mmol, 570 μL, 5.00 eq) at 0° C. Then the mixture was stirred at 30° C. for 2 hr. The reaction mixture was diluted with water (30 mL), extracted with dichloromethane (15 mL×2). The combined organic phases were washed with brine (30 mL), dried over $Na_2SO_4$, filtered and concentrated under vacuum. The residue was purified by column chromatography (SiO2, Petroleum ether/Ethyl acetate=10/1 to 5/1), the spot (Rf=0.8) to obtain tert-butyl 5-(2-chloro-5-pyridyl)-2-azabicyclo[2.2.2]oct-5-ene-2-carboxylate (363 mg, 1.06 mmol, 71.6% yield, 93.4% purity) as a colorless oil; m/z=321.1 $(M+H)^+$.

5-(2-Chloro-5-pyridyl)-2-azabicyclo[2.2.2]oct-5-ene-2. To the solution of tert-butyl 5-(2-chloro-5-pyridyl)-2-azabicyclo[2.2.2]oct-5-ene-2-carboxylate (363 mg, 1.13 mmol, 1.00 eq) in ethyl acetate (8.00 mL) was added HCl/ethyl acetate (4.00 M, 6.13 mL, 21.7 eq). Then the mixture was stirred at 30° C. for 1 hr. The reaction mixture was concentrated under vacuum to yield 5-(2-chloro-5-pyridyl)-2-azabicyclo[2.2.2]oct-5-ene-2 hydrochloride (310 mg, crude) as a light yellow oil; m/z=192.1 $(M-28)^+$; $^1H$ NMR (400 MHz, METHANOL-d4) δ 8.57 (d, J=2.4 Hz, 1H), 8.60-8.54 (m, 1H), 8.04-7.98 (m, 1H), 7.53-7.48 (m, 1H), 6.83 (dd, J=2.0, 6.0 Hz, 1H), 4.50-4.39 (m, 1H), 3.53 (br d, J=2.4 Hz, 1H), 3.34 (s, 1H), 2.91 (br d, J=11.6 Hz, 1H), 2.24-2.14 (m, 1H), 2.01-1.91 (m, 1H), 1.70-1.53 (m, 2H).

2-Methyl-5-(2-chloro-5-pyridyl)-2-azabicyclo[2.2.2]oct-5-ene-2. The solution of 5-(2-chloro-5-pyridyl)-2-azabicyclo[2.2.2]oct-5-ene-2 hydrochloride (210 mg, 951.53 umol, 1 eq) and formaldehyde (1.64 g, 20.1 mmol, 1.50 mL, 21.2 eq) in formic acid (4.00 mL) was stirred at 95-100° C. for 10 hr. The reaction mixture was diluted with water (10 mL), adjusted pH to 8 with sat. $NaHCO_3$, extracted with ethyl acetate (20 mL×4). The combined organic phases were dried over $MgSO_4$, filtered and concentrated under vacuum to obtain 2-methyl-5-(2-chloro-5-pyridyl)-2-azabicyclo[2.2.2]oct-5-ene-2 (20 mg, 72.43 umol, 7.61% yield, 85% purity) as a light yellow oil; m/z=235.1 $(M+H)^+$; 1H NMR (400 MHz, METHANOL-d4) δ 8.58 (d, J=2.0 Hz, 1H), 8.01 (dd, J=2.4, 8.4 Hz, 1H), 7.50 (d, J=8.8 Hz, 1H), 6.83 (d, J=6.0 Hz, 1H), 4.56 (s, 2H), 3.51-3.37 (m, 2H), 2.72 (s, 3H), 2.22 (br d, J=7.2 Hz, 1H), 1.93-1.84 (m, 1H), 1.70-1.53 (m, 2H).

Compound 22

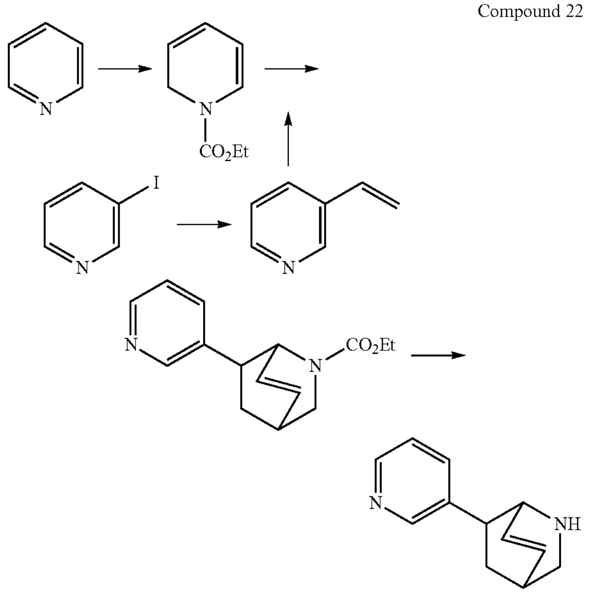

3-Vinylpyridine. A mixture of 3-iodopyridine (16.0 g, 78.1 mmol, 1.00 eq), potassium trifluoro(vinyl)borate (14.6 g, 109 mmol, 1.40 eq), triethylamine (23.7 g, 234 mmol, 32.6 mL, 3.00 eq), bis(triphenylphosphine)palladium(II) dichloride (2.86 g, 3.90 mmol, 0.05 eq) and water (50.0 g, 2.77 mol, 50 mL, 35.5 eq) in 2-propanol (160 mL) was degassed and purged with $N_2$ for 3 times, and then the mixture was stirred at 80° C. for 3 hrs under $N_2$ atmosphere. The reaction mixture was diluted with water (100 mL) and extracted with ethyl acetate (50 mL×3). The organic layer was washed with brine (50 mL×2), dried over $Na_2SO_4$, filtered and concentrated to give the residue. The product was purified by chromatography on a silica gel eluted with petroleum ether:ethyl acetate (from 100:1 to 2:1, petroleum ether/ethyl acetate=5/1, product Rf=0.4) to give a yellow liquid. 3-Vinylpyridine (3.91 g, 36.8 mmol, 47.2% yield, 99.1% purity) was obtained as a yellow liquid; $^1H$ NMR (400 MHz, CDCl3) δ 8.62 (d, 1H), 8.48 (dd, 1H), 7.73 (dt, 1H), 7.23-7.27 (m, 1H), 6.71 (dd, 1H), 5.83 (d, 1H), 5.38 (d, 1H).

Ethyl 2H-pyridine-1-carboxylate. To a solution of pyridine (10.0 g, 126 mmol, 10.2 mL, 1.00 eq) in methanol (200 mL) was added NaBH4 (6.00 g, 158 mmol, 1.25 eq) at −78° C. Then ethyl chloroformate (13.0 g, 120 mmol, 11.4 mL, 0.952 eq) was added dropwise at −78° C. The mixture was stirred at −78° C. for 1 hr. The reaction mixture was quenched by addition of water (100 mL) at 0° C., and then diluted with water (100 mL) and extracted with ethyl acetate (200 mL×3). The combined organic layers were washed with brine (150 mL×2), dried over $Na_2SO_4$, filtered and concentrated under reduced pressure to give a residue. The residue was purified by flash silica gel chromatography (ISCO®; 330 g SepaFlash® Silica Flash Column, Eluent of 0~20% Ethyl acetate/Petroleum ether gradient @ 100 mL/min). Ethyl 2H-pyridine-1-carboxylate (10.0 g, 65.3 mmol, 511.6% yield) was obtained as an yellow oil; $^1H$ NMR (400 MHz, $CDCl_3$) δ 6.84-6.67 (m, 1H), 5.86-5.82 (m, 1H), 5.53-5.52 (m, 1H), 5.13-5.11 (m, 1H), 4.38-4.36 (m, 2H), 4.24-4.20 (m, 2H), 1.32-1.30 (m, 3H).

Ethyl 7-(3-pyridyl)-2-azabicyclo[2.2.2]oct-5-ene-2-carboxylate. To a solution of ethyl 2H-pyridine-1-carboxylate (0.800 g, 5.22 mmol, 2.00 eq) in decalin (5 mL) was added 3-vinylpyridine (274 mg, 2.61 mmol, 1.00 eq). The mixture was stirred at 250° C. for 1 hr under microwave irradiation. The reaction mixture was concentrated under reduced pressure to give a residue. The crude product was purified by reversed-phase HPLC (0.1% $NH_4OH$). Ethyl 7-(3-pyridyl)-2-azabicyclo[2.2.2]oct-5-ene-2-carboxylate (100 mg, 387 μmol, 7.41% yield) was obtained as a yellow oil; $^1H$ NMR (400 MHz, $CDCl_3$) δ 8.65-8.43 (m, 2H), 7.57-7.42 (m, 1H), 7.22-7.15 (m, 1H), 6.63-6.57 (m, 1H), 6.32-6.26 (m, 1H), 4.82-4.79 (m, 1H), 4.26-4.11 (m, 2H), 3.47-3.43 (m, 2H), 3.38-3.35 (m, 1H), 2.92 (s, 1H), 2.22-2.16 (m, 2H), 1.30-1.24 (m, 3H).

7-(3-Pyridyl)-2-azabicyclo[2.2.2]oct-5-ene. To a solution of ethyl 7-(3-pyridyl)-2-azabicyclo[2.2.2]oct-5-ene-2-carboxylate (0.100 g, 387 umol, 1.00 eq) in ethanol (10 mL) was added NaOH (774 mg, 19.3 mmol, 50.0 eq). The mixture was stirred at 100° C. for 3 hrs. NaOH (619.35 mg, 15.48 mmol, 40.0 eq) was added, the mixture was stirred at 100° C. for 12 hrs. The reaction mixture was filtered and concentrated under reduced pressure to give a residue. The crude product was purified by reversed-phase HPLC (0.1% $NH_4OH$). 7-(3-Pyridyl)-2-azabicyclo[2.2.2]oct-5-ene (39.0 mg, 182 umol, 47.1% yield, 87.0% purity) was obtained as a yellow solid; m/z=187 $(M+1)^+$; $^1H$ NMR (400 MHz, $CDCl_3$) δ 8.48-8.45 (m, 1H), 8.43-8.41 (m, 1H), 7.47-7.44 (m, 1H), 7.18-7.15 (m, 1H), 6.56 (t, J=7.4 Hz, 1H), 6.37-6.34 (m, 1H), 3.53-3.52 (m, 1H), 3.52-3.51 (m, 1H), 3.02-2.99 (m, 1H), 2.79-2.77 (m, 1H), 2.51-2.49 (m, 1H), 2.21-2.12 (m, 1H), 1.51-1.44 (m, 2H).

Compound 23

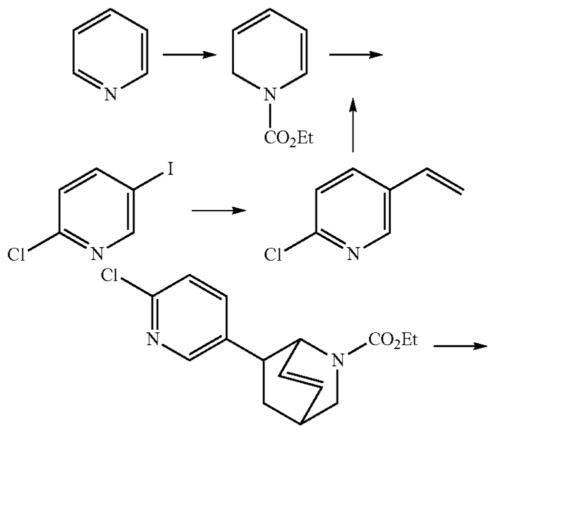

-continued

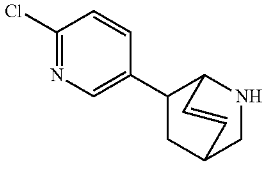

7-(2-Chloro-5-pyridyl)-2-azabicyclo[2.2.2]oct-5-ene was obtained from 2-chloro-5-iodopyridine and ethyl 2H-pyridine-1-carboxylate according to procedures described for Compound 22; m/z=221 $(M+1)^+$; $^1H$ NMR (400 MHz, $CDCl_3$) δ 8.33-8.32 (m, 1H), 7.81-7.80 (m, 1H), 7.31-7.29 (m, 1H), 6.62-6.59 (m, 1H), 6.44-6.41 (m, 1H), 3.32-3.30 (m, 1H), 3.06-3.03 (m, 1H), 2.77-2.73 (m, 2H), 2.59-2.56 (m, 1H), 1.86-1.79 (m, 1H), 1.29-1.27 (m, 1H).

Compound 24

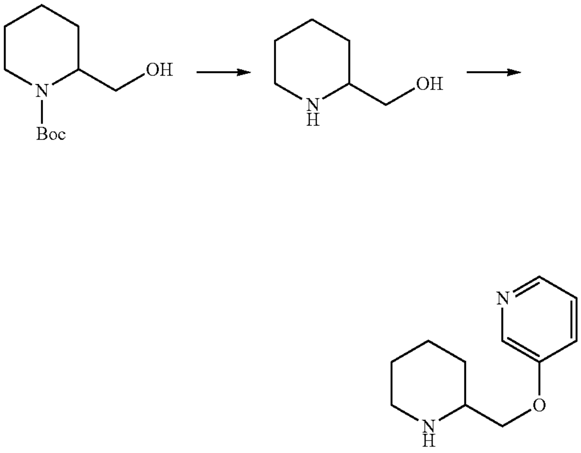

2-Piperidylmethanol. To a solution of N-tert-butoxycarbonyl-2-piperidylmethanol (500 mg, 27.9 mmol, 1.00 eq) in dichloromethane (20 mL) was added solution of hydrogen chloride in dioxane (4 M, 13.9 mL, 2.00 eq), the mixture was stirred at 25° C. for 0.5 hr. The reaction was concentrated to give 2-piperidylmethanol hydrochloride (350 mg, 27.9 mmol, 100% yield) as a white solid.

3-(2-Piperidylmethoxy)pyridine. To a solution of 2-piperidylmethanol hydrochloride (350 mg, 27.9 mmol, 1.00 eq, HCl) in dimethylsulfoxide (10 mL) was added t-BuOK (1.71 g, 139 mmol, 5.00 eq) and 3-fluoropyridine (443 mg, 41.8 mmol, 390 uL, 1.50 eq), the mixture was stirred at 100° C. for 8 hrs. The reaction was diluted with water (100 mL), $K_3PO_4$ (3.00 g) was added, extracted with ethyl acetate (100 mL×2), combined organic phase was dried over $Na_2SO_4$, concentrated to give a residue. The residue was purified by column chromatography (SiO2, MeOH/Ethyl acetate=0/1 to 1/1; TLC:MeOH/Ethyl acetate=1/0 P1: Rf=0.27) to give 3-(2-piperidylmethoxy)pyridine (200.53 mg, 20.8 mmol, 74.6% yield) as a yellow gum; m/z=193.2 $(M+1)^+$; $^1H$ NMR (400 MHz, DMSO-$d_6$) 8.29-8.27 (m, 1H), 8.17-8.15 (m, 1H), 7.39-7.37 (m, 1H), 7.33-7.30 (m, 1H), 3.95-3.91 (m, 1H), 3.85-3.81 (m, 1H), 2.96-2.94 (m, 1H), 2.84-2.80 (m, 1H), 2.43-2.16 (m, 1H), 1.76-1.74 (m, 1H), 1.66-1.63 (m, 1H), 1.53-1.51 (m, 1H), 1.34-1.31 (m, 2H), 1.29-1.21 (m, 1H).

Compound 25

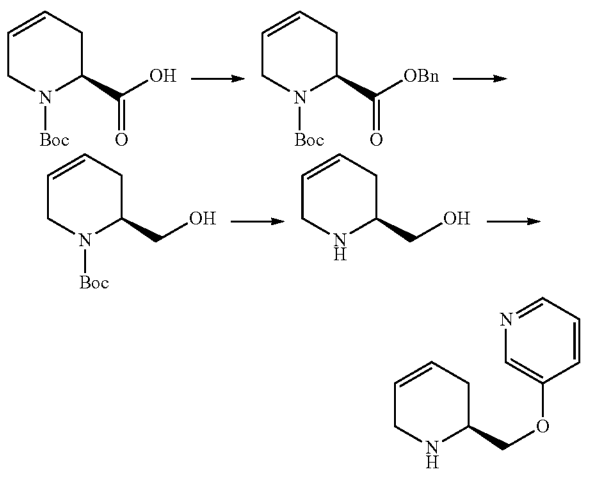

Benzyl (2S)-1-tert-butoxycarbonyl-3,6-dihydro-2H-pyridine-2-carboxylate. To a solution of (2S)-1-tert-butoxycarbonyl-3,6-dihydro-2H-pyridine-2-carboxylic acid (500 mg, 2.20 mmol, 1.00 eq) in DMF (5 mL) was added $NaHCO_3$ (400 mg, 4.76 mmol, 185 uL, 2.16 eq) and benzyl bromide (576 mg, 3.37 mmol, 400 uL, 1.53 eq). The mixture was stirred at 25° C. for 12 hrs. The reaction mixture was partitioned between water (100 mL) and ethyl acetate 80 (mL).

The organic phase was separated, washed with water 80 mL (40 mL×2), dried over $Na_2SO_4$, filtered and concentrated under reduced pressure to give a residue. The residue was purified by flash silica gel chromatography (ISCO®; 12 g SepaFlash® Silica Flash Column, eluent of 0~20% ethyl acetate/petroleum ether gradient, flow rate 60 mL/min), to obtain benzyl (2S)-1-tert-butoxycarbonyl-3,6-dihydro-2H-pyridine-2-carboxylate (600 mg, 1.89 mmol, 85.9% yield) as a colorless oil; $^1H$ NMR (400 MHz, $CDCl_3$) 7.37-7.32 (m, 5H), 5.75-5.65 (m, 2H), 5.17-5.11 (m, 3H), 4.08-4.03 (m, 1H), 3.82-3.74 (m, 1H), 2.73-2.65 (m, 1H), 2.53-2.48 (m, 1H), 1.47-1.41 (m, 9H).

[(2S)-1-tert-butoxycarbonyl-1,2,3,6-tetrahydropyridin-2-yl]methanol. To a solution of benzyl (2S)-1-tert-butoxycarbonyl-3,6-dihydro-2H-pyridine-2-carboxylate (600 mg, 1.89 mmol, 1.00 eq) in THE (5 mL) was added $LiBH_4$ (250 mg, 11.5 mmol, 6.07 eq). The mixture was stirred at 25° C. for 2 hrs. The reaction mixture was quenched by addition of $NH_4Cl$ (20 mL) at 25° C., and then diluted with water (20 mL) and extracted with ethyl acetate (20 mL×3). The combined organic layers were washed with brine 930 mL0, dried over $Na_2SO_4$, filtered and concentrated under reduced pressure to give a residue. The residue was purified by flash silica gel chromatography (ISCO®; 12 g SepaFlash® Silica Flash Column, eluent of 0~30% ethyl acetate/petroleum ether gradient, flow rate 60 mL/min), (360 mg, 1.69 mmol, 89.3% yield) to obtain [(2S)-1-tert-butoxycarbonyl-1,2,3,6-tetrahydropyridin-2-yl]methanol as a colorless oil; $^1H$ NMR (400 MHz, $CDCl_3$) 5.74-5.72 (m, 1H), 5.71-5.68 (m, 1H), 4.48 (s, 1H), 4.19 (s, 1H), 3.66-3.49 (m, 3H), 2.43-2.37 (m, 1H), 2.05-1.99 (m, 1H), 1.49 (s, 9H).

[(2S)-1,2,3,6-tetrahydropyridin-2-yl]methanol. To a solution of [(2S)-1-tert-butoxycarbonyl-1,2,3,6-tetrahydropyridin-2-yl]methanol (300 mg, 1.41 mmol, 1.00 eq) in dichloromethane (10 mL) was added solution of hydrogen chloride in dioxane (4 M, 2 mL, 5.69 eq). The mixture was stirred at 25° C. for 0.5 hr. The mixture was concentrated to give [(2S)-1,2,3,6-tetrahydropyridin-2-yl]methanol hydrochloride (210 mg, 1.41 mmol, 100.00% yield) as a white solid that was used into the next step without further purification.

3-[[(2S)-1,2,3,6-Tetrahydropyridin-2-yl]methoxy]pyridine. To a solution of [(2S)-1,2,3,6-tetrahydropyridin-2-yl]methanol hydrochloride (210 mg, 1.41 mmol, 1.00 eq) in dimethylsulfoxide (5 mL) was added t-BuOK (789 mg, 7.03 mmol, 5.00 eq) and 3-fluoropyridine (205 mg, 2.11 mmol, 180 uL, 1.50 eq). The mixture was stirred at 100° C. for 8 hrs. The mixture was purified by preparative HPLC (basic condition) to give 3-[[(2S)-1,2,3,6-tetrahydropyridin-2-yl]methoxy]pyridine (114.58 mg, 586 umol, 41.7% yield, 97.3% purity) as a yellow oil; m/z=191.2 $(M+1)^+$; $^1H$ NMR) 400 MHz, DMSO-$d_6$) 8.30-8.17 (m, 1H), 8.16-8.15 (m, 1H), 7.41-7.39 (m, 1H), 7.33-7.31 (m, 1H), 5.72 (s, 2H), 4.03-3.99 (m, 1H), 3.94-3.89 (m, 1H), 3.29-3.21 (m, 2H), 3.05-3.04 (m, 1H), 2.04-2.01 (m, 1H), 1.89-1.85 (m, 1H).

Compound 26

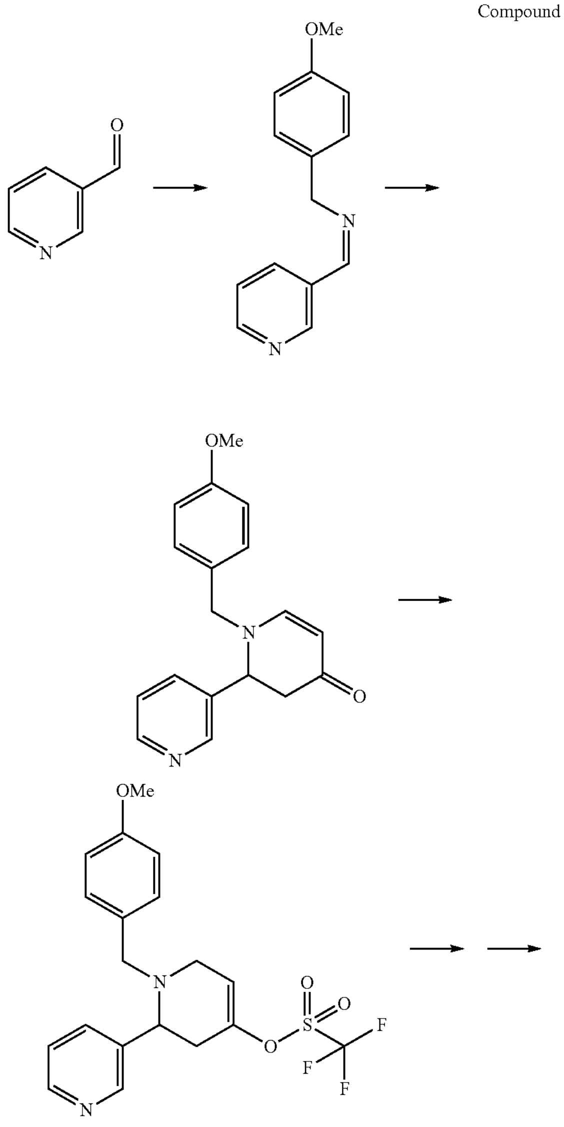

-continued

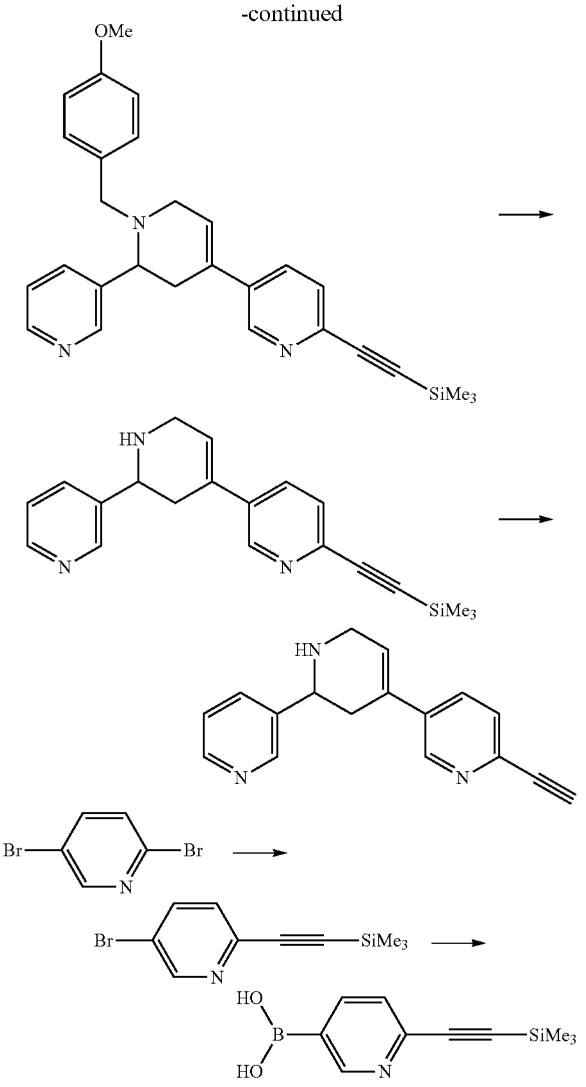

2-(5-Bromo-2-pyridyl)ethynyl-trimethyl-silane. A mixture of 2,5-dibromopyridine (5.00 g, 21.1 mmol, 1.00 eq), triethylamine (8.54 g, 84.4 mmol, 11.7 mL, 4.00 eq), CuI (200 mg, 1.06 mmol, 0.0500 eq), $Pd(PPh_3)_2Cl_2$ (740 mg, 1.06 mmol, 0.0500 eq) and dimethylformamide (25 mL) was stirred. Ethynyl(trimethyl)silane (2.49 g, 25.3 mmol, 3.51 mL, 1.20 eq) was added and the mixture was stirred at 25° C. for 2 hrs. The mixture was filtered and was added water (100 mL), extracted with ethyl acetate (50 mL×3), washed with brine (100 mL), dried by $Na_2SO_4$, filtered and concentrated on vacuum. The residue was purified by column chromatography (SiO2, Petroleum ether/Ethyl acetate=1/0 to 10/1). TLC (Petroleum ether/Ethyl acetate=10/1, Rf of P1 was 0.5). 2-(5-Bromo-2-pyridyl)ethynyl-trimethyl-silane (3.00 g, 10.8 mmol, 51.5% yield, 92.1% purity) was obtained as a light yellow oil; m/z=254 $(M+1)^+$.

[6-(2-Trimethylsilylethynyl)-3-pyridyl]boronic acid. A mixture of 2-(5-bromo-2-pyridyl)ethynyl-trimethyl-silane (3.00 g, 11.8 mmol, 1.00 eq), bis(pinacolato)diboron (3.60 g, 14.1 mmol, 1.20 eq), KOAc (3.47 g, 35.4 mmol, 3.00 eq), $Pd(PPh_3)_2Cl_2$ (431 mg, 590 umol, 0.0500 eq) and dioxane (30 mL) was degassed and stirred at 85° C. for 2 hrs. To the mixture was added water (100 mL), extracted with ethyl acetate (50 mL×3), washed with brine (100 mL), dried by $Na_2SO_4$, filtered and concentrated on vacuum. The residue was purified by preparative HPLC (HCl). [6-(2-Trimethylsilylethynyl)-3-pyridyl]boronic acid (1.40 g, 4.89 mmol, 41.4% yield, 76.6% purity) was obtained as a dark brown oil; m/z=220 $(M+1)^+$.

N-(p-Tolylmethyl)-1-(3-pyridyl)methanimine. To a solution of pyridine-3-carbaldehyde (13.7 g, 100 mmol, 12.9 mL, 1.00 eq) in 2-propanol (250 mL), p-methoxybenzylamine (16.1 g, 150 mmol, 14.1 mL, 1.50 eq) and acetic acid (1.50 g, 25.0 mmol, 1.43 mL, 0.25 eq) were added. The reaction mixture was stirred at 25° C. for 1.5 hs. The reaction mixture was concentrated and then diluted with ethyl acetate (150 mL). The resulting solution was washed with saturated $NaHCO_3$ solution (50 mL×2) and brine (50 mL×2), dried over anhydrous $Na_2SO_4$, filtered and concentrated. N-(p-tolylmethyl)-1-(3-pyridyl)methanimine (28.1 g, crude) was obtained as a brown oil and used into the next step without further purification.

1-(p-Tolylmethyl)-2-(3-pyridyl)-2,3-dihydropyridin-4-one. To a solution of N-(p-tolylmethyl)-1-(3-pyridyl)methanimine (19.5 g, 86.2 mmol, 1.00 eq) in dry tetrahydrofuran (450 mL) was added a solution of $ZnCl_2$ (12.9 g, 94.8 mmol, 4.44 mL, 1.10 eq) in tetrahydrofuran (50 mL) and dichloromethane (50 mL) at −78° C. and stirred for 10 mins. Then 1-methoxy-3-[(trimethylsilyl)oxy]-1,3-butadiene (18.6 g, 108 mmol, 21.0 mL, 1.25 eq) was added to the mixture, and after stirring for 30 mins the mixture was allowed to warm up to −20° C. and stirred for 20 mins. Then the reaction mixture was allowed to warm to 25° C. and stirred for 12 hrs. The reaction mixture was quenched with saturated $NaHCO_3$ (400 mL) and extracted with ethyl acetate (150 mL×2). The combined organic phase was acidified with 1 M HCl (400 mL). The resulting aqueous phase was separated and further washed with ethyl acetate (400 mL). Then the aqueous phase was neutralized with saturated $NaHCO_3$ (400 mL) and extracted with ethyl acetate (150 mL×2). The combined organic phase was dried over anhydrous $Na_2SO_4$, filtered and concentrated. The residue was purified by flash silica gel chromatography (ISCO®; 330 g SepaFlash® Silica Flash Column, Eluent of 0~80% ethyl acetate/petroleum ether gradient, flow rate 100 mL/min) to obtain 1-(p-tolylmethyl)-2-(3-pyridyl)-2,3-dihydropyridin-4-one (13.4 g, 45.4 mmol, 52.6% yield) as a yellow oil; $^1$H NMR (400 MHz, $CDCl_3$) 8.59-8.45 (m, 2H), 7.66-7.63 (m, 1H), 7.27-7.05 (m, 2H), 7.05-7.03 (m, 2H), 6.89-6.87 (m, 2H), 5.11-5.09 (m, 1H), 4.53-4.49 (m, 1H), 4.36-4.31 (m, 1H), 4.09-3.81 (m, 1H), 3.80 (s, 3H), 2.91-2.85 (m, 1H), 2.63-2.56 (m, 1H).

[1-(p-Tolylmethyl)-2-(3-pyridyl)-3,6-dihydro-2H-pyridin-4-yl]trifluoromethanesulfonate. To a solution of 1-(p-tolylmethyl)-2-(3-pyridyl)-2,3-dihydropyridin-4-one (11.0 g, 37.4 mmol, 1.00 eq) and N,N-bis(trifluoromethylsulfonyl) aniline (14.7 g, 41.1 mmol, 1.10 eq) in tetrahydrofuran (50 mL), L-selectride (1 M, 41.1 mL, 1.10 eq) was added dropwise at −78° C. After 1 h, the solution was allowed to warm up to 25° C. and stirred for another hour. The reaction mixture was quenched with saturated $NH_4Cl$ solution (500 mL) and extracted with ethyl acetate (300 mL×2). The combined organic phase was washed with brine (500 mL), dried over anhydrous $Na_2SO_4$, filtered and concentrated to obtain a brown residue. The residue was purified by column chromatography (silica gel, Petroleum ether/Ethyl acetate=30/1 to 3/1) to get [1-(p-tolylmethyl)-2-(3-pyridyl)-3,6-dihydro-2H-pyridin-4-yl]trifluoromethanesulfonate (Petroleum ether/Ethyl acetate=3/1, Rf=0.6) (5.20 g, 12.1 mmol, 32.5% yield) as a yellow oil; $^1$H NMR (400 MHz, $CDCl_3$) 8.65-8.57 (m, 2H), 7.79-7.77 (m, 1H), 7.36-7.33 (m, 1H), 7.27-7.18 (m, 2H), 6.87-6.84 (m, 2H), 6.01-5.55 (m, 1H), 3.94-3.91 (m, 1H), 3.80 (s, 3H), 3.62-3.58 (m, 1H), 3.26-3.17 (m, 1H), 3.14-3.06 (m, 2H), 2.73-2.71 (m, 2H).

Trimethyl-[2-[5-[1-(p-tolylmethyl)-2-(3-pyridyl)-3,6-dihydro-2H-pyridin-4-yl]-2-pyridyl]ethynyl]silane. A mixture of [1-(p-tolylmethyl)-2-(3-pyridyl)-3,6-dihydro-2H-pyridin-4-yl]trifluoromethanesulfonate (500 mg, 1.17 mmol, 1.00 eq), [6-(2-trimethylsilylethynyl)-3-pyridyl]boronic acid (400 mg, 1.40 mmol, 1.20 eq), LiCl (49 mg, 1.17 mmol, 23.9 uL, 1.00 eq), $Pd(PPh_3)_2Cl_2$ (170 mg, 233 umol, 0.200 eq), $K_3PO_4$ (2 M, 1.75 mL, 3.00 eq) and dioxane (10 mL) was degassed and stirred at 80° C. for 2 hrs. The mixture was filtered and to the solution was added water (10 mL), extracted with ethyl acetate (5 mL×3), washed with brine (10 mL), dried by $Na_2SO_4$, filtered and concentrated on vacuum. The residue was purified by preparative HPLC (HCl). Trimethyl-[2-[5-[1-(p-tolylmethyl)-2-(3-pyridyl)-3,6-dihydro-2H-pyridin-4-yl]-2-pyridyl]ethynyl]silane (0.300 g, 552 umol, 47.3% yield, 83.5% purity) was obtained as a dark brown oil; m/z=454 $(M+1)^+$.

Trimethyl-[2-[5-[2-(3-pyridyl)-1,2,3,6-tetrahydropyridin-4-yl]-2-pyridyl]ethynyl]silane. Trimethyl-[2-[5-[1-(p-tolylmethyl)-2-(3-pyridyl)-3,6-dihydro-2H-pyridin-4-yl]-2-pyridyl]ethynyl]silane (0.250 g, 551 umol, 1.00 eq) and trifluoroacetic acid (2 mL) were taken up into a microwave tube. The sealed tube was heated at 100° C. for 2 hrs under microwave. The reaction mixture was concentrated under reduced pressure to give a residue. The crude product was purified by reversed-phase HPLC (0.1% TFA condition). Trimethyl-[2-[5-[2-(3-pyridyl)-1,2,3,6-tetrahydropyridin-4-yl]-2-pyridyl]ethynyl]silane (0.120 g, 359 umol, 65.3% yield) was obtained as a dark brown oil; m/z=334 $(M+1)^+$.

2-Ethynyl-5-[2-(3-pyridyl)-1,2,3,6-tetrahydropyridin-4-yl]pyridine. To a solution of trimethyl-[2-[5-[2-(3-pyridyl)-1,2,3,6-tetrahydropyridin-4-yl]-2-pyridyl]ethynyl]silane (0.100 g, 299 umol, 1.00 eq) in methanol (1 mL) and dichloromethane (3 mL) was added $K_2CO_3$ (124 mg, 899 umol, 3.00 eq). The mixture was stirred at 25° C. for 1 h. The reaction mixture was filtered and concentrated under reduced pressure to give a residue. The residue was purified by preparative HPLC (basic condition; column: Xtimate C18 150*25 mm*5 um; mobile phase: [water (0.05% ammonia hydroxide v/v)-ACN]; B %: 12%-42%, 10 min). 2-Ethynyl-5-[2-(3-pyridyl)-1,2,3,6-tetrahydropyridin-4-yl] pyridine (15.8 mg, 58.5 umol, 19.5% yield, 96.7% purity) was obtained as a yellow solid; m/z=262 $(M+1)^+$; $^1$H NMR (400 MHz, $CDCl_3$) 8.69-8.65 (m, 2H), 8.58-8.56 (m, 1H), 7.79-7.78 (m, 1H), 7.65-7.63 (m, 1H), 7.45-7.43 (m, 1H), 7.44-7.33 (m, 1H), 6.35-6.33 (m, 1H), 4.06-4.02 (m, 1H), 3.82-3.74 (m, 2H), 3.18 (s, 1H), 2.64-2.67 (m, 2H).

Compound 27

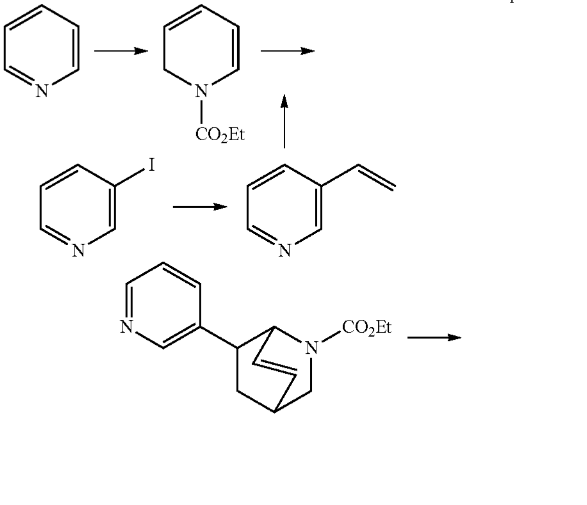

-continued

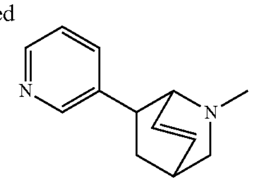

3-Vinylpyridine. A mixture of 3-iodopyridine (16.0 g, 78.1 mmol, 1.00 eq), potassium trifluoro(vinyl)borate (14.6 g, 109 mmol, 1.40 eq), triethylamine (23.7 g, 234 mmol, 32.6 mL, 3.00 eq), bis(triphenylphosphine)palladium(II) dichloride (2.86 g, 3.90 mmol, 0.05 eq) and water (50.0 g, 2.77 mol, 50 mL, 35.5 eq) in 2-propanol (160 mL) was degassed and purged with $N_2$ for 3 times, and then the mixture was stirred at 80° C. for 3 hrs under $N_2$ atmosphere. The reaction mixture was diluted with water (100 mL) and extracted with ethyl acetate (50 mLx3). The organic layer was washed with brine (50 mLx2), dried over $Na_2SO_4$, filtered and concentrated to give the residue. The product was purified by chromatography on a silica gel eluted with petroleum ether:ethyl acetate (from 100:1 to 2:1, petroleum ether/ethyl acetate=5/1, product Rf=0.4) to give a yellow liquid. 3-Vinylpyridine (3.91 g, 36.8 mmol, 47.2% yield, 99.1% purity) was obtained as a yellow liquid; $^1H$ NMR (400 MHz, CDC13) δ 8.62 (d, 1H), 8.48 (dd, 1H), 7.73 (dt, 1H), 7.23-7.27 (m, 1H), 6.71 (dd, 1H), 5.83 (d, 1H), 5.38 (d, 1H).

Ethyl 2H-pyridine-1-carboxylate. To a solution of pyridine (10.0 g, 126 mmol, 10.2 mL, 1.00 eq) in methanol (200 mL) was added NaBH4 (6.00 g, 158 mmol, 1.25 eq) at −78° C. Then ethyl chloroformate (13.0 g, 120 mmol, 11.4 mL, 0.952 eq) was added dropwise at −78° C. The mixture was stirred at −78° C. for 1 hr. The reaction mixture was quenched by addition of water (100 mL) at 0° C., and then diluted with water (100 mL) and extracted with ethyl acetate (200 mLx3). The combined organic layers were washed with brine (150 mLx2), dried over $Na_2SO_4$, filtered and concentrated under reduced pressure to give a residue. The residue was purified by flash silica gel chromatography (ISCO®; 330 g SepaFlash® Silica Flash Column, Eluent of 0~20% Ethyl acetate/Petroleum ether gradient @ 100 mL/min). Ethyl 2H-pyridine-1-carboxylate (10.0 g, 65.3 mmol, 51.6% yield) was obtained as an yellow oil; $^1H$ NMR (400 MHz, $CDCl_3$) δ 6.84-6.67 (m, 1H), 5.86-5.82 (m, 1H), 5.53-5.52 (m, 1H), 5.13-5.11 (m, 1H), 4.38-4.36 (m, 2H), 4.24-4.20 (m, 2H), 1.32-1.30 (m, 3H).

Ethyl 7-(3-pyridyl)-2-azabicyclo[2.2.2]oct-5-ene-2-carboxylate. To a solution of ethyl 2H-pyridine-1-carboxylate (0.800 g, 5.22 mmol, 2.00 eq) in decalin (5 mL) was added 3-vinylpyridine (274 mg, 2.61 mmol, 1.00 eq). The mixture was stirred at 250° C. for 1 hr under microwave irradiation. The reaction mixture was concentrated under reduced pressure to give a residue. The crude product was purified by reversed-phase HPLC (0.1% $NH_4OH$). Ethyl 7-(3-pyridyl)-2-azabicyclo[2.2.2]oct-5-ene-2-carboxylate (100 mg, 387 μmol, 7.41% yield) was obtained as a yellow oil; $^1H$ NMR (400 MHz, $CDCl_3$) δ 8.65-8.43 (m, 2H), 7.57-7.42 (m, 1H), 7.22-7.15 (m, 1H), 6.63-6.57 (m, 1H), 6.32-6.26 (m, 1H), 4.82-4.79 (m, 1H), 4.26-4.11 (m, 2H), 3.47-3.43 (m, 2H), 3.38-3.35 (m, 1H), 2.92 (s, 1H), 2.22-2.16 (m, 2H), 1.30-1.24 (m, 3H).

2-Methyl-7-(3-pyridyl)-2-azabicyclo[2.2.2]ocit-5-ene. To a solution of ethyl 7-(3-pyridyl)-2-azabicyclo[2.2.2]oct-5-ene-2-carboxylate (0.100 g, 387 umol, 1.00 eq) in tetrahydrofuran (5 mL) was added lithium aluminum hydride (117 mg, 3.10 mmol, 8.00 eq) at 0° C. The mixture was stirred at 25° C. for 2 hrs. The reaction mixture was quenched by addition water 5 mL at 0° C. and then filtered and concentrated under reduced pressure to give a residue. The residue was purified by prep-TLC (SiO2, DCM/MeOH=10/1). TLC (DCM/MeOH=10/1) showed one major spot (Rf=0.3) was detected. 2-Methyl-7-(3-pyridyl)-2-azabicyclo[2.2.2]oct-5-ene (15.9 mg, 78.7 μmol, 20.3% yield, 98.7% purity) was obtained as a white solid; m/z=201 $(M+1)^+$; $^1H$ NMR: (400 MHz, MeOD) δ 8.45-8.42 (m, 2H), 7.71-7.68 (m, 1H), 7.41-7.38 (m, 1H), 6.93-6.89 (m, 1H), 6.30-6.27 (m, 1H), 4.00 (m, 1H), 3.69-3.65 (m, 1H), 3.42-3.39 (m, 1H), 3.04 (m, 1H), 2.67 (s, 3H), 2.53-2.50 (m, 1H), 2.30-2.27 (m, 1H), 1.68-1.64 (m, 1H).

Compound 28

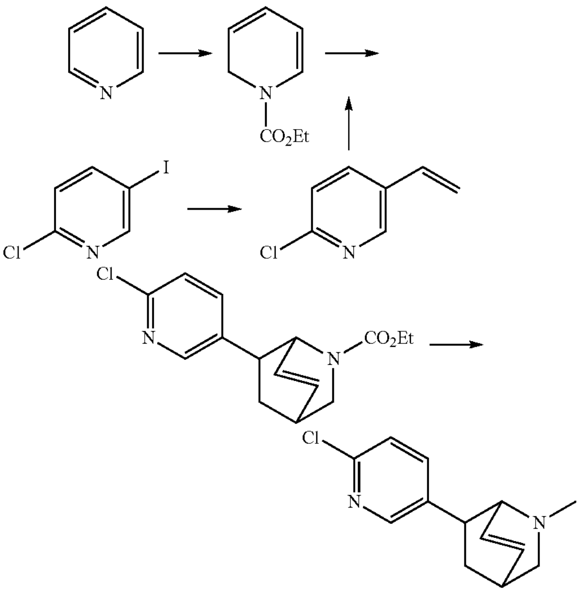

2-Methyl-7-(2-chloro-5-pyridyl)-2-azabicyclo[2.2.2]oct-5-ene. To a solution of 7-(2-chloro-5-pyridyl)-2-azabicyclo[2.2.2]oct-5-ene (0.100 g, 453 umol, 1.00 eq) in formic acid (3 mL) was added formaldehyde (327 mg, 4.03 mmol, 0.3 mL, 37.0% purity, 8.89 eq). The mixture was stirred at 100° C. for 1 hr. The reaction mixture was concentrated under reduced pressure to give a residue. The residue was purified by preparative HPLC (basic condition; column: Xtimate C18 150*25 mm*5 um; mobile phase: [water (0.05% ammonia hydroxide v/v)-acetonitrile]; B %: 32%-62%, 10 min). 2-Methyl-7-(2-chloro-5-pyridyl)-2-azabicyclo[2.2.2]oct-5-ene (10.0 mg, 40.3 umol, 8.9% yield, 94.5% purity) was obtained as an yellow oil; m/z=235 $(M+1)^+$; $^1H$ NMR (400 MHz, $CDCl_3$) δ 8.20 (s, 1H), 7.45-7.43 (m, 1H), 7.20-7.18 (m, 1H), 6.68-6.65 (m, 1H), 6.17-6.13 (m, 1H), 3.55-3.53 (m, 1H), 3.41 (d, J=2.6 Hz, 1H), 3.23-3.20 (m, 1H), 2.76-2.74 (m, 1H), 2.33-2.13 (m, 3H), 2.13-2.01 (m, 1H), 1.99-1.97 (m, 1H), 1.47-1.43 (m, 1H).

Compound 29 was isolated as a side product during synthesis of Compound 28, m/z=245 $(M+1)^+$; $^1H$ NMR (400 MHz, $CDCl_3$) δ 7.95 (s, 1H), 7.43-7.36 (m, 1H), 6.68-6.64 (m, 1H), 6.61-6.59 (m, 1H), 6.19-6.14 (m, 1H), 4.33-4.28 (m, 2H), 3.58-3.56 (m, 1H), 3.45-3.44 (m, 1H), 3.29-3.27 (m, 1H), 2.76-2.75 (m, 1H), 2.37 (s, 3H), 2.16-2.12 (m, 1H), 2.03-1.99 (m, 1H), 1.47-1.43 (m, 1H), 1.39-1.35 (m, 3H).

The invention claimed is:

1. A compound, which is:

2-phenyl-5-(1,2,3,6-tetrahydropyridin-2-yl)pyridine;

2-chloro-5-(1,2,3,6-tetrahydropyridin-2-yl)pyridine;

2,3-dichloro-5-(1,2,3,6-tetrahydropyridin-2-yl)pyridine;

3-ethynyl-5-(1,2,3,6-tetrahydropyridin-2-yl)pyridine;

2-[5-(1,2,3,6-tetrahydropyridin-2-yl)-3-pyridyl]-2,5-diazabicyclo[2.2.1]heptane;

3-[(2S)-4-phenyl-1,2,3,6-tetrahydropyridin-2-yl]pyridine;

3-[(2S)-2-(3-pyridyl)-1,2,3,6-tetrahydropyridin-4-yl]pyridine;

2-methyl-3-(2-phenyl-5-pyridyl)-2-azabicyclo[2.2.2]octane;

5-(2-chloro-5-pyridyl)-2-azabicyclo[2.2.2]oct-5-ene;

5-(2-chloro-5-pyridyl)-2-methyl-2-azabicyclo[2.2.2]oct-5-ene;

7-(3-pyridyl)-2-azabicyclo[2.2.2]oct-5-ene;

7-(2-chloro-5-pyridyl)-2-azabicyclo[2.2.2]oct-5-ene;

3-[[(2S)-1,2,3,6-tetrahydropyridin-2-yl]methoxy]pyridine;

2-ethynyl-5-[2-(3-pyridyl)-1,2,3,6-tetrahydropyridin-4-yl]pyridine;

2-methyl-7-(3-pyridyl)-2-azabicyclo[2.2.2]oct-5-ene;

7-(2-chloro-5-pyridyl)-2-methyl-2-azabicyclo[2.2.2]oct-5-ene; or 7-(2-ethoxypyridin-5-yl)-2-methyl-2-azabicyclo[2.2.2]oct-5-ene, wherein the compound is optionally in salt or solvate form.

2. A method of reducing or treating an infestation with one or more ectoparasites, wherein the one or more ectoparasites comprises a mosquito, a flea or a tick, the method comprising:

exposing the one or more ectoparasites to a compound of formula (I), optionally as a salt or crystal:

(I)

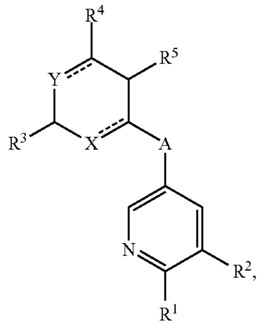

wherein

X is (i) C—$R^7$, if the ===== attached to X is a double bond, or (ii) $C(R^7)_2$ or N—$R^7$, if the ===== attached to X is a single bond, Y is (i) C—$R^8$, if one of the ===== attached to Y is a double bond, or (ii) $C(R^8)_2$ or N—$R^8$, if none of the ===== attached to Y is a double bond, $R^1$ and $R^2$ are each independently H, halogen, alkyl, heteroalkyl, alkenyl, alkynyl, optionally substituted aryl, or optionally substituted heteroaryl, $R^3$, $R^4$, and $R^5$ are each independently H, alkyl, alkenyl, alkynyl, optionally substituted aryl, or optionally substituted heteroaryl, or wherein $R^3$ and $R^5$, are optionally taken together to form group Z, which is —$CH_2$—$CH_2$—, —$CH_2$—$NR^9$, or —$NR^9$—$CH_2$—, each $R^9$ being independently H, or alkyl, =====, in each case, independently indicates a single bond or a double bond, A is a bond or -L1-L2-L3-L4-, L1 being connected to the ring comprising X and Y, wherein L1 is a methylene group, L2 is —O—, L3 is a bond, L4 is a bond, $R^7$ and $R^8$ are each independently H, or alkyl, and wherein an optional substituent of the optionally substituted aryl, and optionally substituted heteroaryl is/are each independently halogen, alkyl, haloalkyl, and/or heteroalkyl, wherein compounds of the following formula are excluded:

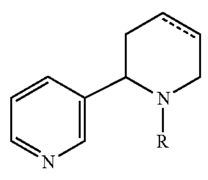

wherein

R represents hydrogen or $C_1$-$C_5$ alkyl, and

===== represents a single or double bond.

3. The method of claim 2, wherein the ring comprising X and Y comprises only two double bonds.

4. The method of claim 2, wherein the ring comprising X and Y comprises only one double bond.

5. The method of claim 2, wherein the compound of formula (I) has formula (Ig):

(Ig)

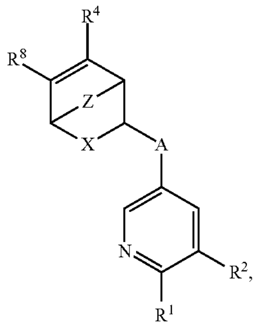

wherein $R^1$, $R^2$, $R^4$, $R^8$, A, X, and Z are as defined for the compound of formula (I).

6. The method of claim 2, wherein the compound of formula (I) has formula (II):

(II)

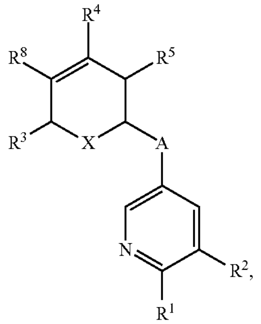

wherein $R^1$, $R^2$, $R^3$, $R^4$, $R^3$, $R^8$, A, and X are as defined for the compound of formula (I).

7. The method of claim 2, wherein $R^1$ is H, halogen, alkyl, heteroalkyl, alkynyl, or aryl.

8. The method of claim 2, wherein $R^2$ is H, halogen, alkyl, heteroalkyl, alkynyl, or aryl.

9. The method of claim 2, wherein the exposing comprises employing the compound of formula (I) as a repellent, and/or wherein the exposing comprises applying the compound of formula (I) to a mammal.

10. The method of claim 2, wherein the exposing comprises applying the compound of formula (I) as a topical formulation, a shampoo composition, a cleansing composition or a treatment composition.

11. The method of claim 2, wherein the one or more ectoparasites comprise a mosquito or a tick.

12. The method of claim 2, wherein $R^1$ is H, halogen, heteroalkyl, or aryl.

13. The method of claim 2, wherein $R^1$ is H, halogen, —O-alkyl, or phenyl.

* * * * *